US010328141B2

(12) United States Patent
Seeberger et al.

(10) Patent No.: US 10,328,141 B2
(45) Date of Patent: Jun. 25, 2019

(54) SYNTHETIC VACCINES AGAINST STREPTOCOCCUS PNEUMONIAE TYPE 1

(71) Applicant: MAX-PLANCK-GESELLSCHAFT ZUR FÖRDERUNG DER WISSENSCHAFTEN E.V., Munich (DE)

(72) Inventors: Peter H. Seeberger, Kleinmachnow (DE); Claney Lebev Pereira, Berlin (DE); Chakkumkal Anish, The Hague (NL); Benjamin Schumann, Berlin (DE)

(73) Assignee: Max-Planck-Gesellschaft zur Förderung der Wissenschaften E.V., Munich (DE)

(*) Notice: Subject to any disclaimer, the term of this patent is extended or adjusted under 35 U.S.C. 154(b) by 164 days.

(21) Appl. No.: 14/903,118

(22) PCT Filed: Jul. 7, 2014

(86) PCT No.: PCT/EP2014/064407
§ 371 (c)(1),
(2) Date: Jan. 6, 2016

(87) PCT Pub. No.: WO2015/004041
PCT Pub. Date: Jan. 15, 2015

(65) Prior Publication Data
US 2016/0346374 A1 Dec. 1, 2016

(30) Foreign Application Priority Data

Jul. 7, 2013 (EP) .................... 13175447
Sep. 10, 2013 (EP) .................... 13183826
Dec. 10, 2013 (EP) .................... 13196568

(51) Int. Cl.
A61K 31/7028 (2006.01)
A61K 39/09 (2006.01)
C07H 15/04 (2006.01)
G01N 33/569 (2006.01)
A61K 47/64 (2017.01)
A61K 39/00 (2006.01)

(52) U.S. Cl.
CPC ........ *A61K 39/092* (2013.01); *A61K 31/7028* (2013.01); *A61K 47/646* (2017.08); *C07H 15/04* (2013.01); *G01N 33/56944* (2013.01); *A61K 2039/6037* (2013.01); *A61K 2039/627* (2013.01); *G01N 2333/3156* (2013.01); *G01N 2469/20* (2013.01)

(58) Field of Classification Search
None
See application file for complete search history.

(56) References Cited

FOREIGN PATENT DOCUMENTS

| WO | WO 2005/093422 | 10/2005 | |
|---|---|---|---|
| WO | WO 2011/133227 | 10/2011 | |
| WO | WO2011/137181 | * 11/2011 | ......... A61K 31/7056 |

OTHER PUBLICATIONS

Kalka-Moll et al., "Zwitterionic Polysaccharides Stimulate T Cells by MHC Class II-Dependent Interactions" The Journal of Immunology (2002) vol. 169 pp. 6149-6153.*
Perera et al., "Hydrophobic Thiolation of Pectin with 4-Aminothiophenol: Synthesis and In Vitro Characterization" AAPS PharmaSciTech (2010) vol. 11 No. 1 pp. 174-180 (Year: 2010).*
Eisel et al., "Tetanus toxin: primary structure, expression in E. coli, and homology with botulinum toxins" The EMBO Journal (1986) vol. 5 No. 10 pp. 2495-2502 (Year: 1986).*
Christina et al., "Galacturonic Acid Lactones in the Synthesis of All Trisaccharide Repeating Units of the Zwitterionic Polysaccharide Sp1" Journal of Organic Chemistry (2011) vol. 26 pp. 1692-1706 (Year: 2011).*
Manea et al., "Multivalent, Saccharide-Functionalized Gold Nanoparticles as Fully Synthetic Analogs of Type A Neisseria meningitidis Antigens" Advanced Materials (2008) vol. 20 pp. 4348-4352 (Year: 2008).*
Safari et al., "Gold nanoparticles as carriers for a synthetic *Streptococcus pneumoniae* type 14 conjugate vaccine" Nanomedicine (2012) vol. 7 No. 5 pp. 651-662 (Year: 2012).*
Matsuoka et al., "Introduction of monosaccharides having functional groups onto a carbosilane dendrimer: A broadly applicable one-pot reaction in liquid ammonia involving Birch reduction and subsequent SN2 reaction" Carbohydrate Research vol. 329 pp. 765-772 (Year: 2000).*
Buskas et al., "The Immunogenicity of the Tumor-Associated Antigen Lewisy May Be Suppressed by a Bifunctional Cross-Linker Required for Coupling to a Carrier Protein" *Chem. Eur. J.* (2004) 10(14):3517-3524.
Christina et al., "Galacturonic Acids Lactones in the Synthesis of All Rrisaccaraide Repeating Units of the Zwitterionic Polysaccharaide Sp1" *J. Org. Chem.* (2011) 76(6):1692-1706 (with supporting information).
Kawano et al., "Natural killer-like nonspecific tumor cell lysis mediated by specific ligand-activated Vα14 NKT cells" *PNAS* 95(10):5690-5693.
Marinier et al., "Novel mimics of sialyl Lewis X: Design, Synthesis and Biological Activity of a Series of 2- and 3-Malonate Substituted Galactoconjugates" *Bioorg. Med. Chem.* (2001) 9(6):1395-1427.

(Continued)

Primary Examiner — Eric Olson
(74) Attorney, Agent, or Firm — Knobbe Martens Olson & Bear LLP

(57) ABSTRACT

The present invention relates to the total synthesis of saccharide structures contained in the capsular polysaccharide of Streptococcus pneumoniae type 1, to glycoconjugates containing said saccharide structures obtained by total synthesis and to use of such glycoconjugates and pharmaceutical compositions thereof in the immunization against diseases associated with bacteria containing said saccharide structures in their capsular polysaccharide, and more specifically associated with Streptococcus pneumoniae.

7 Claims, 6 Drawing Sheets

(56) References Cited

OTHER PUBLICATIONS

Nagorny et al., "On the Emerging Role of Chemistry in the Fashioning of Biologics: Synthesis of a Bidomainal Fucosyl GM1-Based Vaccine for the Treatment of Small Cell Lung Cancer" *J. Org. Chem.* (2009) 74(15):5157-5162 (with supporting information).
Pragani et al., "De Novo Synthesis of a 2-Acetamido-4-amino-2,4,6-trideoxy-D-galactose (AAT) Building Block for the Preparation of a *Bacteroides fragilis* A1 Polysaccharide Fragment" *Org. Lett.* (2010) 12(7):1624-1627 (with supporting information).
Ragupathi et al., "On the power of chemical synthesis: Immunological evaluation of models for multiantigenic carbohydrate-based cancer vaccines" *PNAS* (2002) 99(21):13699-13704.
Semeraro et al., "Self-Assembly of Calix[6]arene-Diazapyrenium Pseudorotaxanes: Interplay of Molecular Recognition and Ion-Pairing Effects" *Chem. Eur. J.* (2010) 16(11):3467-3475.
Van Den Bos et al., "Uronic Acids in Olgosaccharide Synthesis" *Eur. J. Org. Chem.* (2007) 2007(24):3963-3976.
Wojcik et al., "Synthesis of Carbohydrate-Functionalised Sequence-Defined Oligo(amidoamine)s by Photochemical Thiol-Ene Coupling in a Continuous Flow Reactor" *Chem. Eur. J.* (2013) 19(9):3090-3098.
Wu et al., "Synthesis of Monomeric and Dimeric Repeating Units of the Zwitterioninc Type; 1 Capsular Polysaccaride from *Streptococcus phenumoniae*" *Chem. Eur. J.* (2010) 16(11):3476-3488.
International Search Report and Written Opinion dated Aug. 26, 2014 for PCT Application No. PCT/EP2014/065507, filed Jul. 7, 2014.
Sahabuddin, et al., "Synthesis of N-modified sTn analogs and evaluation of their immunogenicities by microarray-based immunoassay," Tetrahedron (2010) 66(38):7510-7519.
Japanese Office Action dated Apr. 3, 2018 for Japanese Patent Application No. 2016-524767, filed Jul. 7, 2014.

\* cited by examiner

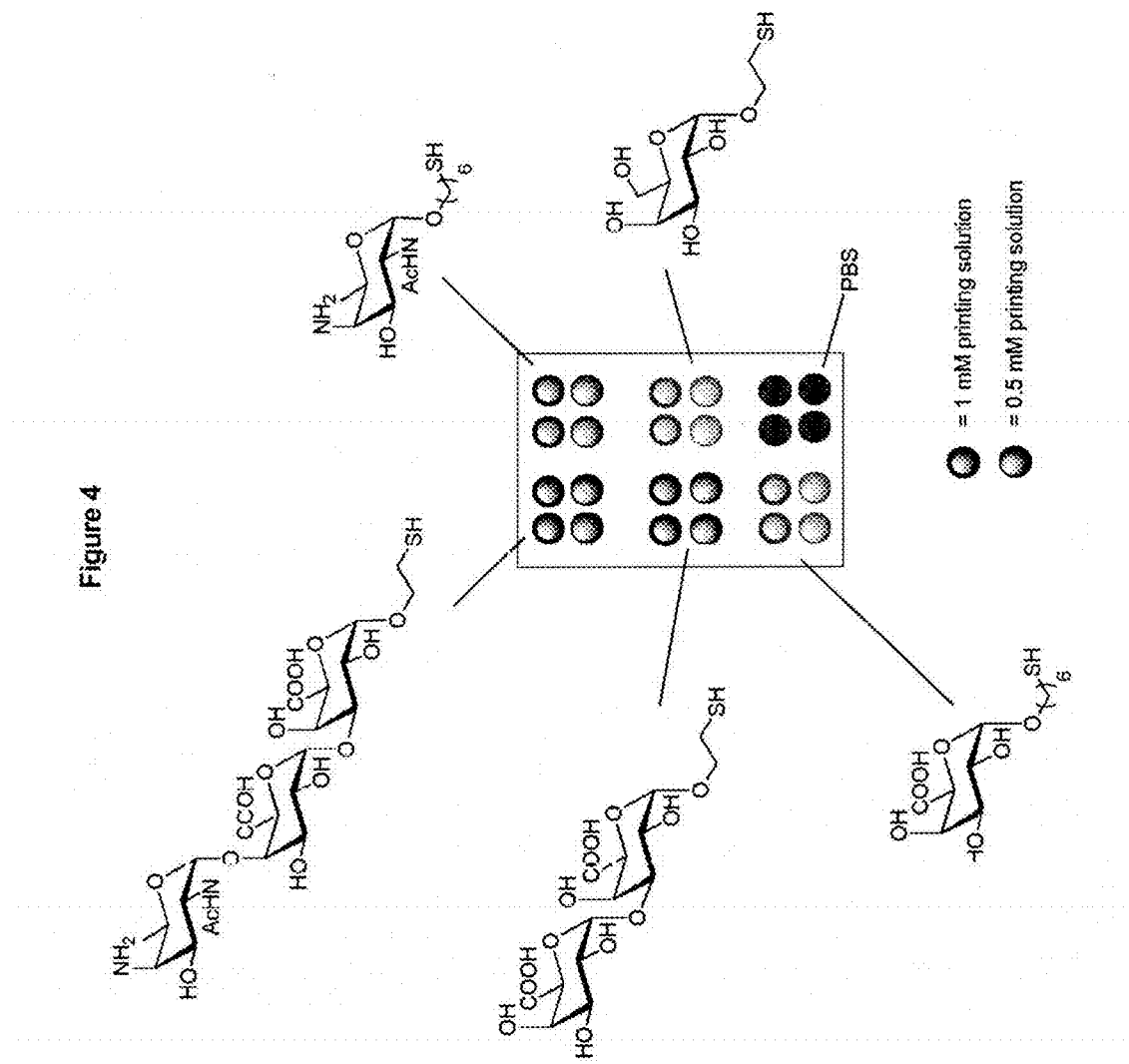

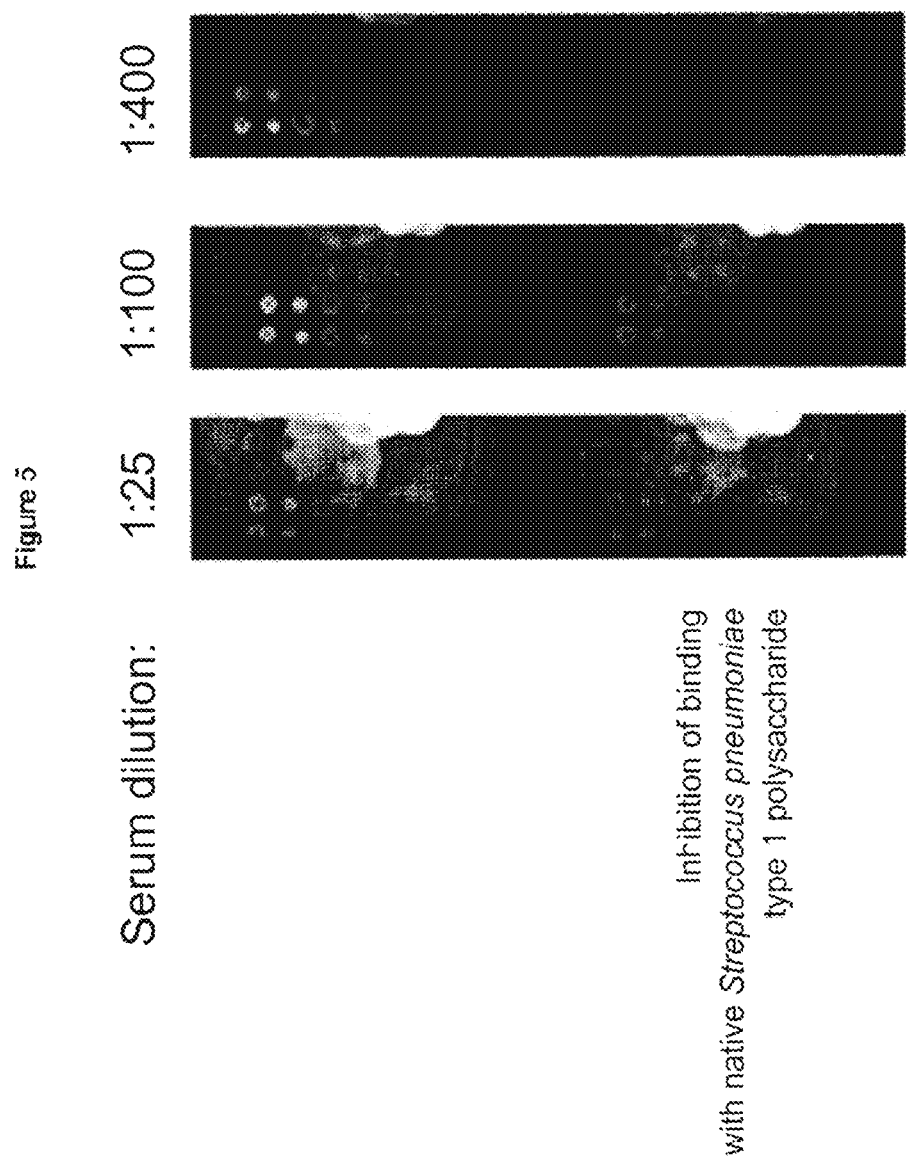

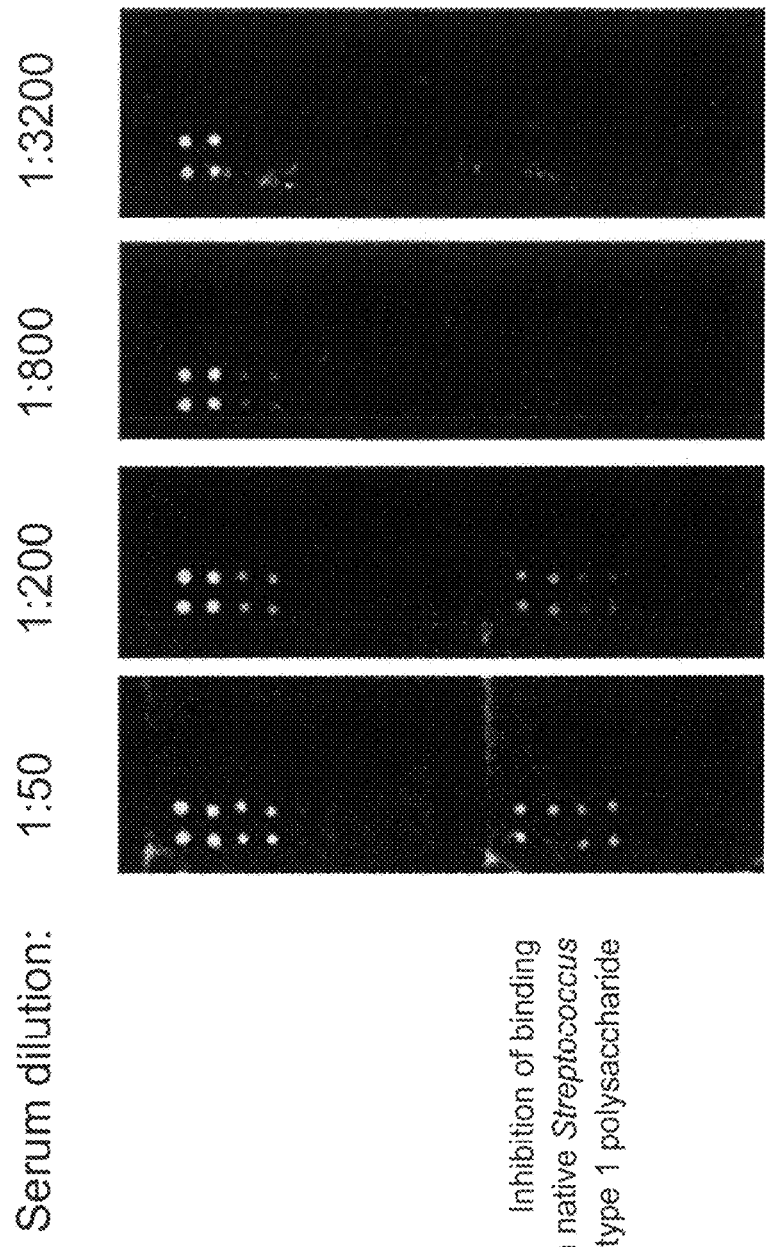

SYNTHETIC VACCINES AGAINST STREPTOCOCCUS PNEUMONIAE TYPE 1

FIELD OF THE INVENTION

The present invention relates to the total synthesis of saccharide structures contained in the capsular polysaccharide of *Streptococcus pneumoniae* type 1, to glycoconjugates containing said saccharide structures obtained by total synthesis and to the use of such glycoconjugates and pharmaceutical compositions thereof in the immunization against diseases associated with bacteria, and more specifically against diseases associated with *Streptococcus pneumoniae*.

BACKGROUND OF THE INVENTION

Gram-positive encapsulated bacterium *Streptococcus pneumoniae* (pneumococcus) is a major cause of morbidity and mortality worldwide. They colonize the upper respiratory tract and cause invasive pneumococcal diseases such as meningitis, bacteremia and bactermic pneumonia, and non-invasive pneumococcal diseases including acute otis media and pneumonia. These diseases are prevalent in young children, the elderly and immunocompromised individuals of all ages. In developing countries *Streptococcus pneumoniae* related diseases cause an estimated 1.2 million deaths annually of young children.

Structurally, three distinguished layers can be seen on the bacterial surface: plasma membrane, cell wall and capsule. The cell wall consists of a peptidoglycan backbone anchoring the cell wall polysaccharide (C-polysaccharide) and the capsular polysaccharide (CPS). The C-polysaccharide is a structure common to all the pneumococcal serotypes, whereas CPS is specific to each of the 90 know serotypes and is the main virulence factor.

Out of the 90 serotypes the most common and prevalent serotypes found in the world are shown in FIG. 1. This distribution varies also based on geography and age difference. Thus, a vaccine comprising glycoconjugates containing an immunogenic carrier and saccharide structures derived from the capsular polysaccharide of the most common and prevalent *Streptococcus pneumoniae* serotypes would provide immunization against a high percentage of the diseases caused by this class of Gram-positive bacteria.

Several poly-valent pneumococcal vaccines were manufactured up to present. The commercially available 23-valent pneumococcal polysaccharide vaccine (PPV), contains purified capsular polysaccharide (CPS) antigens of 23 serotypes. However, this vaccine is not effective in the case of infants and young children. The currently marketed pneumococcal conjugate vaccine (PCV), PCV-7 (Prevnar™) contains saccharides of capsular antigens of serotype 4, 6B, 9V, 14, 18C, 19F and 23F individually conjugated to diphtheria $CRM_{197}$ and is effective in infants.

The currently marketed vaccines are effective in North America and Europe for individuals of a particular age. The manufacturing process for these vaccines is complex and results in a higher price. Therefore, the vaccine is unaffordable in most developing countries. It is the object of the present invention to provide affordable synthetic saccharide vaccines that contain most of the prevalent serotypes of the developing world.

*Streptococcus pneumoniae* type 1 (SP1) is one of the most prevalent *S. pneumoniae* serotypes. *Streptococcus pneumoniae* type 1 capsular polysaccharide is a linear polymer having as a repeating unit: [→3)-α-2,4,6-trideoxy-4-amino-D-GalNAc-(1→4)-α-D-GalAp-(1→3)-α-D-GalAp-(1→].

Synthetic saccharide structures derived from [→3)-α-2,4,6-trideoxy-4-amino-D-GalNAc-(14)-α-D-GalAp-(1→3)-α-D-GalAp-(1→] trisaccharide repeating unit of *Streptococcus pneumoniae* type 1 capsular polysaccharide were already reported. However, the method developed by Bundle (*Chem. Eur. J.* 2010, 16, 3476.) provides α-methoxy saccharides, which are not suitable for conjugation to an immunogenic carrier.

It is the objective of the present invention to provide an improved synthetic route to access saccharide structures functionalized with a linker, said saccharide structures being derived from [→3)-α-2,4,6-trideoxy-4-amino-D-GalNAc-(1→4)-α-D-GalAp-(1→3)-α-D-GalAp-(1→] trisaccharide repeating unit of *Streptococcus pneumoniae* type 1 capsular polysaccharide. Said saccharide structures have the advantage of being functionalized with a linker thus, being suitable to be conjugated to an immunogenic carrier. Therefore, it is an objective of the present invention to provide glycoconjugates and pharmaceutical compositions containing said glycoconjugates for immunization against diseases associated with bacteria containing in their capsular polysaccharide one of the following structures: α-2,4,6-trideoxy-4-amino-D-GalNAc-(1→4)-α-D-GalAp-(1→3)-α-D-GalAp; α-2,4,6-trideoxy-4-amino-D-GalNAc-(1→4)-α-D-GalAp; α-D-GalAp-(1→3)-α-D-GalAp; α-D-GalAp; α-2,4,6-trideoxy-4-amino-D-GalNAc; α-D-GalAp-(1→3)-α-D-GalAp-(1→3)-α-2,4,6-trideoxy-4-amino-D-GalNAc; α-D-GalAp-(1→3)-α-2,4,6-trideoxy-4-amino-D-GalNAc; α-D-GalAp-(1→3)-α-2,4,6-trideoxy-4-amino-D-GalNAc-(1→4)-α-D-GalAp. The pharmaceutical compositions comprising the saccharides of general formula (I) and/or the intermediates of general formula (II) and/or the glycoconjugates according to the present invention are for use in immunization against diseases associated with bacteria, and especially associated with *Streptococcus pneumoniae*, said diseases including pneumonia, meningitis, otitis media, bacteremia and acute exacerbation of chronic bronchitis, sinusitis, arthritis and conjunctivitis The objective of the present invention is solved by the teaching of the independent claims. Further advantageous features, aspects and details of the invention are evident from the dependent claims, the description, the figures, and the examples of the present application.

DESCRIPTION OF THE INVENTION

Definitions

The term "linker" as used herein encompasses molecular fragments capable of connecting the reducing-end monosaccharide of a saccharide with an immunogenic carrier or a solid support, optionally by binding to at least one interconnecting molecule. Thus, the function of the linker per se or together with the interconnecting molecule is to establish, keep and/or bridge a special distance between the reducing-end monosaccharide and an immunogenic carrier or a solid support. More specifically, one extremity of the linker is connected to the exocyclic oxygen atom at the anomeric center of the reducing-end monosaccharide and the other extremity is connected via the sulfur atom with the interconnecting molecule, or directly with the immunogenic carrier or the solid support.

As used herein, the term "interconnecting molecule" refers to a bifunctional molecule containing functional group X and functional group Y, wherein functional group X is capable of reacting with the terminal thiol group on the linker A and the functional group Y is capable of binding to an immunogenic carrier or to a solid support. FIG. 2 displays examples of commercially available interconnecting molecules, but does not restrict the interconnecting molecules that can be used according to the present invention to the examples displayed herein.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the person skilled in the art, classically recognized examples of adjuvants include:

mineral-containing compositions, including calcium salts and aluminum salts (or mixtures thereof). Calcium salts include calcium phosphate. Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt. The adjuvants known as aluminum hydroxide and aluminum phosphate may be also used. The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i. e. aluminium hydroxyphosphate sulfate). They may be obtained by precipitation, and the reaction conditions and concentrations during precipitation influence the degree of substitution of phosphate for hydroxyl in the salt. Mixtures of both an aluminium hydroxide and an aluminium phosphate can be employed in the formulation according to the present invention;

saponins, which are a heterologous group of sterol glycosides and triterpenoid glycosides that are found in the bark, leaves, stems, roots and even flowers of a wide range of plant species. Saponin from the bark of the *Quillaia saponaria*, Molina tree have been widely studied as adjuvants. Saponin can also be commercially obtained from *Smilax ornata* (sarsaprilla), *Gypsophilla paniculata* (brides veil), and *Saponaria oficianalis* (soap root). Saponin adjuvant formulations include purified formulations, such as QS21, as well as lipid formulations, such as ISCOMs. Saponin compositions have been purified using HPLC and RP-HPLC. Specific purified fractions using these techniques have been identified, including QS7, QS 17, QS 18, QS2 1, QH-A, QH-B and QH-C. Saponin formulations may also comprise a sterol, such as cholesterol. Combinations of saponins and cholesterols can be used to form unique particles called immunostimulating complexes (ISCOMs). ISCOMs generally include a phospholipid such as phosphatidylethanolamine or phosphatidylcholine. Any known saponin can be used in ISCOMs. Preferably, the ISCOM includes one or more of QuilA, QHA & QHC;

microparticles (i.e. a particle of 100 nm to 150 pm in diameter, more preferably 200 nm to 30 pm in diameter, or 500 nm to 10 pm in diameter) formed from materials that are biodegradable and non-toxic. Such non-toxic and biodegradable materials include, but are not restricted to poly($\alpha$-hydroxy acid), polyhydroxybutyric acid, polyorthoester, polyanhydride, polycaprolactone;

CD1d ligands, such as an $\alpha$-glycosylceramide, phytosphingosine-containing $\alpha$-glycosylceramides, OCH, KRN7000 [(2S,3S,4R)-1-O-($\alpha$-D-galactopyranosyl)-2-(N-hexacosanoylamino)-1,3,4-octadecanetriol], CRONY-101, 3"-sulfo-galactosylceramide;

immunostimulatory oligonucleotides, such CpG motif containing ones (a dinucleotide sequence containing an unmethylated cytosine residue linked by a phosphate bond to a guanosine residue), or CpI motif containing ones (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded;

compounds containing lipids linked to a phosphate-containing acyclic backbone, such as the TLR4 antagonist E5564;

oil emulsions (e.g. Freund's adjuvant).

Theoretically, each molecule or substance that is able to favor or amplify a particular situation in the cascade of immunological events, ultimately leading to a more pronounced immunological response, can be defined as an adjuvant.

In principle, through the use of adjuvants in vaccine formulations, one can direct and optimize immune responses that are appropriate or desirable for the vaccine;

enable mucosal delivery of vaccines, i.e. administration that results in contact of the vaccine with a mucosal surface such as buccal or gastric or lung epithelium and the associated lymphoid tissue;

promote cell-mediated immune responses;

enhance the immunogenicity of weaker immunogens, such as highly purified or recombinant antigens;

reduce the amount of antigen or the frequency of immunization required to provide protective immunity; and improve the efficacy of vaccines in individuals with reduced or weakened immune responses, such as newborns, the aged, and immunocompromised vaccine recipients.

Although little is known about their mode of action, it is currently believed that adjuvants augment immune responses by one of the following mechanisms:

increasing the biological or immunologic half-life of antigens;

improving antigen delivery to antigen-presenting cells (APCs), as well as antigen processing and presentation by the APCs e.g., by enabling antigen to cross endosomal membranes into the cytosol after ingestion of antigen-adjuvant complexes by APC;

mimicking danger inducing signals from stressed or damaged cells, which serve to initiate an immune response;

inducing the production of immunomodulatory cytokines;

biasing the immune response towards a specific subset of the immune system; and blocking the rapid dispersal of the antigen challenge.

Saccharides are known by the person skilled in the art as TI-2 (T cell independent-2) antigens and poor immunogens. Therefore, to produce a saccharide-based vaccine, said saccharides are conjugated to an immunogenic carrier to provide a glycoconjugate, which presents an increased immunogenicity in comparison with the saccharide. In this context the term "immunogenic carrier" is defined as a structure, which is conjugated to the saccharide to form a glycoconjugate that presents an increased immunity in comparison with the saccharide per se. Thus, the conjugation of the saccharides to the immunogenic carrier has as effect the stimulation of the immune response against said saccharide, without inducing an immune response against the said immunogenic carrier.

As used herein the term "O-glycosidic bond" refers to the covalent bond connecting the anomeric carbon of sugar fragments S1, S2 and S3 (i.e. the carbon C-1) to sugar fragments S1, S2, S3 or to —O-A-SH fragment through an oxygen atom. In case the anomeric carbon of sugar fragments S1, S2 and S3 is connected to —O-A-SH fragment, the oxygen atom is the terminal oxygen atom of the fragment —O-A-SH. In case the anomeric carbon of sugar fragments S1, S2 and S3 is connected to another sugar fragment S1, S2, S3, then the oxygen atom is the oxygen atom at position 3 of sugar fragment S1, or the oxygen atom at position 3 of sugar fragment S2, or the oxygen atom at position 4 of sugar fragment S3. In other words, the saccharides according to the invention do not contain —O—O— bonds or sugar fragments connected or bound to each other via their anomeric or C-1 carbons.

Thus, the present invention relates to saccharides of general formula (I):

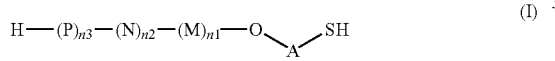

(I)

wherein A is a linker;
M, N and P represent independently of each other one of the following sugar fragments:

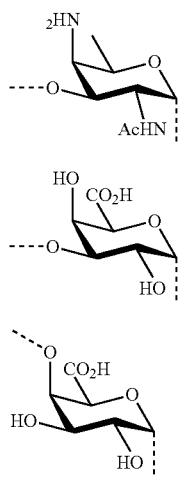

S1

S2

S3 wherein the sugar fragments S1, S2, S3 are connected to each other and to —O-A-SH fragment via O-glycosidic bonds, each sugar fragment S1, S2, and S3 is not more than once present in the general formula (I), sugar fragment S1 cannot be simultaneously connected to —O-A-SH and sugar fragment S3, sugar fragment S3 cannot be simultaneously connected to —O-A-SH and sugar fragment S2, and sugar fragment S2 cannot be simultaneously connected to —O-A-SH and sugar fragment S1, and n1, n2 and n3 are integers selected from 0 and 1, wherein at least one of the integers n1, n2 and n3 is 1 and pharmaceutically acceptable salts of these saccharides.

Each sugar fragment S1, S2, and S3 is not more than once present in the general formula (I) means that each of M, N and P has to represent one of S1, S2 and S3 and none of the sugar fragments S1, S2 and S3 can be selected twice. Thus, if M is S1, then N can only be selected from S2 and S3 but cannot represent S1, and if M is S1 and N is S2, P can only be S3.

The term "cannot be simultaneously connected to" refers to a direct connection. "Direct connection" means that, for instance when the sugar fragment S1 is directly connected to the fragment —O-A-SH, then the sugar fragment S1 is linked through its anomeric carbon atom to the fragment —O-A-SH and not indirectly via another sugar fragment (e.g. S3) to the fragment —O-A-SH. Each sugar fragment S1 or S2 or S3 can be connected through two positions, which are indicated by dotted lines. One position is the anomeric carbon C-1, which can be linked to the oxygen of the fragment —O-A-SH or to an oxygen atom with a dotted line of another sugar fragment. The oxygen with a dotted line of each sugar fragment S1 or S2 or S3 cannot be linked to the fragment —O-A-SH and can only be linked to a hydrogen atom (in case of the terminal sugar fragment) or to an anomeric carbon C-1 of another sugar fragment. However, when linking the sugar fragments and the —O-A-SH fragment together, the exceptions as disclosed herein have to be taken into consideration.

Thus, under the scope of the present invention are falling saccharides of general formula (Ia)

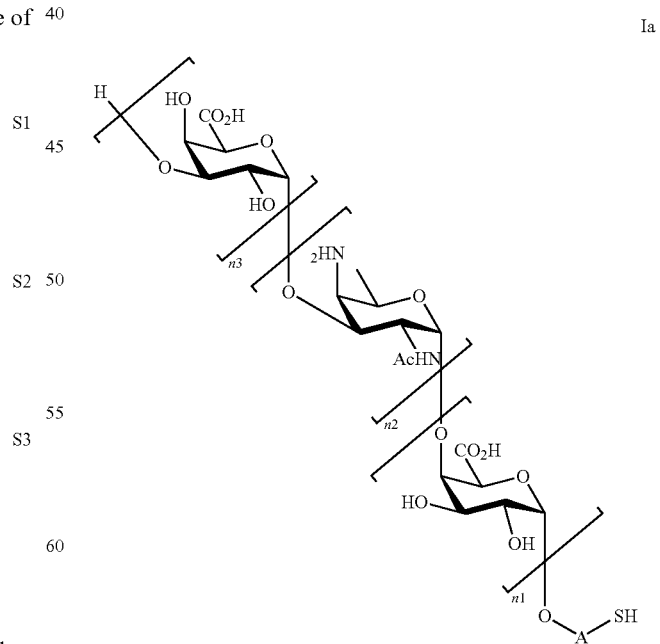

Ia wherein
n1=n2=n3=1, or n1=n2=1 and n3=0, or n2=n3=1 and n1=0, or n1=1 and n2=n3=0, or n2=1 and n1=n3=0;

and saccharides of general formula (Ib)

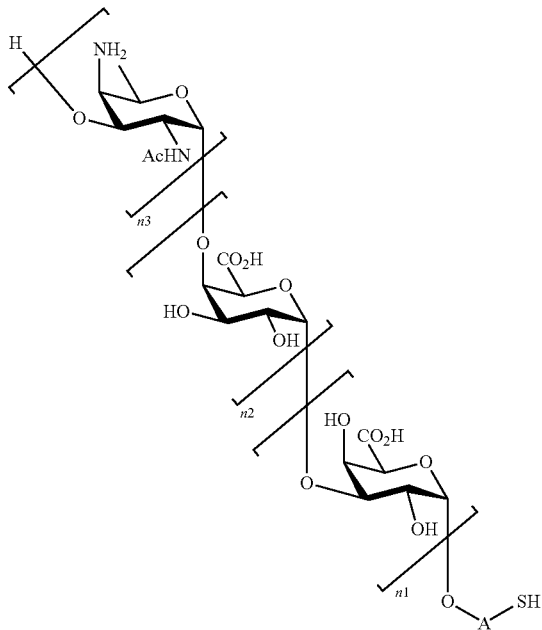

wherein
n1=n2=n3=1, or n1=n2=1 and n3=0, or n2=n3=1 and n1=0, or n1=1 and n2=n3=0, or n3=1 and n1=n2=0;
and saccharides of general formula (Ic)

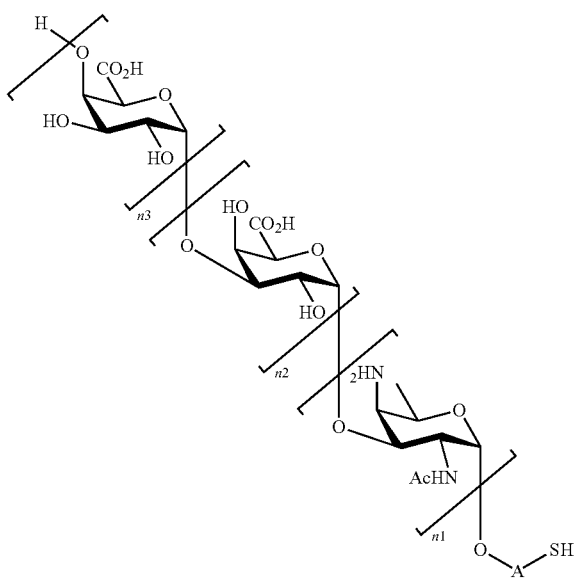

wherein
n1=n2=n3=1, or n1=n2=1 and n3=0, or n2=n3=1 and n1=0, or n3=1 and n1=n2=0
and pharmaceutically acceptable salts of these saccharides.

In other words, the present invention relates to saccharides of general formula (I):

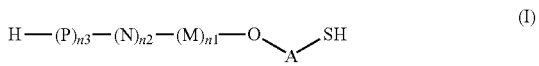

wherein A is a linker;
P represents S1, N represents S3, M represents S2;
or
P represents S3, N represents S2, M represents S1;
or
P represents S2, N represents S1, M represents S3;
and
n1=n2=n3=1, or n1=n2=1 and n3=0, or n2=n3=1 and n=0, or n1=1 and n2=n3=0, or n2=1 and n1=n3=0, or n3=1 and n1=n2=0
wherein S1, S2 and S3 are sugar fragments defined as

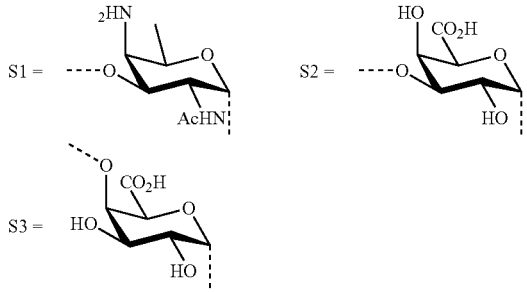

and the sugar fragments S1, S2, S3 are connected to the each other and to —O-A-SH fragment via O-glycosidic bonds,
and pharmaceutically acceptable salts of these saccharides.

Preferably not more than one of n1, n2 and n3 is 0 or n1=n2=n3=1, and even more preferred n1=n2=n3=1. Also saccharides of general formula (I) comprising the sugar S1 are preferred. Thus, it is preferred that general formula (I) represents the following sugars: H—(S1)-(S3)-(S2)-O-A-SH, H—(S2)-(S1)-(S3)-O-A-SH, H—(S3)-(S2)-(S1)-O-A-SH, H—(S2)-(S1)-O-A-SH, H—(S3)-(S2)-O-A-SH, H—(S1)-(S3)-O-A-SH, H—(S1)-O-A-SH, H—(S2)-O-A-SH and more preferred H—(S1)-(S3)-(S2)-O-A-SH, H—(S2)-(S1)-(S3)-O-A-SH, H—(S3)-(S2)-(S1)-O-A-SH, H—(S2)-(S1)-O-A-SH, H—(S1)-(S3)-O-A-SH, and H—(S1)-O-A-SH.

Especially preferred saccharides of general formula (I) are:

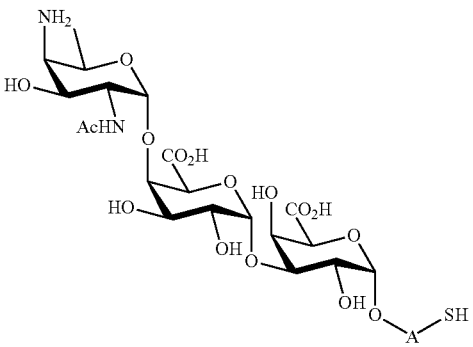

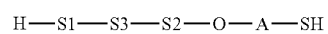

-continued

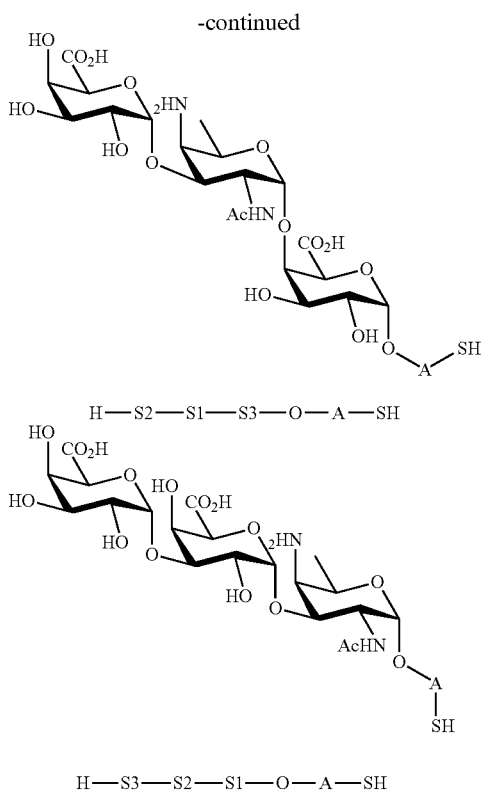

H—S2—S1—S3—O—A—SH

H—S3—S2—S1—O—A—SH

A is defined as a linker and is part of the fragment —O-A-SH. Thus, the linker A is bound to an oxygen atom and to an SH-group, while the oxygen atom and the SH-group are bound to different carbon atoms of the linker A. It is preferred that at least two carbon atoms of the linker are between the oxygen atom and the SH-group, like —O—C—C-SH.

The linker A preferably contains between 2 and 20 carbon atoms (including the carbon atoms of optional side chains), more preferably between 2 and 18, more preferably between 2 and 16, more preferably between 2 and 14, more preferably between 2 and 12, and still more preferably between 2 and 10 carbon atoms.

The shortest atom chain between the oxygen (i.e. the oxygen of —O-A-SH) and the SH-group consists preferably of 2 to 14 atoms, more preferably of 2 to 12 atoms, more preferably of 2 to 10 atoms, more preferably of 2 to 8 atoms. In case the shortest chain (which is the shortest possible connection between the oxygen and the SH-group) consists of 2 to 5 atoms, these are preferably carbon atoms. In case the shortest chain consists of 4 to 8 atoms, the chain may contain 1, 2, 3, or 4 heteroatoms selected from O, N and S. In case the shortest chain consists of 9 to 14 atoms, the chain may contain 1, 2, 3, 4, 5, or 6 heteroatoms selected from O, N and S. It is preferred that the shortest chain contains 0, 1, or 2 sulphur atoms and/or 0, 1, or 2 nitrogen atoms and/or 0, 1, 2, or 3 oxygen atoms. In case more than 4 oxygen atoms are present, preferably no other heteroatoms are present.

It is also preferred that the linker A, or the shortest chain is fully or partially fluorinated. The linker A may contain a 4-membered or a 5-membered or a 6-membered saturated carbocycle or a 6-membered partly unsaturated (and not aromatic) carbocycle or a 4-membered or a 5-membered or a 6-membered saturated oxygen heterocycle or a 4-membered or a 5-membered or a 6-membered saturated nitrogen heterocycle.

The linker A may also contain amide (—NH—CO—, —CO—NH—) and/or urea (—NH—CO—NH—) residues and preferably only one amide or urea residue. The linker may also contain substituents and preferably one substituent such as $R^1$ or two substituents such as $R^1$ and $R^2$, which have the meanings as defined herein and which are preferably selected from —OCH$_3$, —OC$_2$H$_5$, —CH$_3$, —C$_2$H$_5$, —CH$_2$F, —CF$_2$H, —CF$_3$, —C(O)—NH$_2$, —NHAc, —NH(CH$_3$), —NH(C$_2$H$_5$), —N(CH$_3$)$_2$, —N(C$_2$H$_5$)$_2$, —NH—C(O)—CH$_3$, and —C(O)—CH$_3$.

In case the linker is fluorinated, more than two substituents —F are preferred.

In case an oxygen heterocycle is present each carbon atom of the oxygen heterocycle may be substituted by a hydroxy group (—OH). Thus, a 5-membered oxygen heterocycle may contain one or two hydroxy groups and a 6-membered oxygen heterocycle may contain one or two or preferably 3 hydroxy groups.

The linker A, also defined herein as -$A^a$-$A^b$-$A^c$-$A^d$- or -$A^a$-$A^b$-$A^d$- contains preferably 1, 2, 3 or 4 and more preferably 1, 2, or 3 of the following fragments:
—(CH$_2$)$_{o1}$—, —(CR$^1$R$^2$)$_{o1}$—, —(CH$_2$)$_{o3}$—(CH$_2$—CH$_2$—O)$_{o2}$—(CH$_2$)$_{o1}$—, —(CH$_2$)$_{o1}$—S—(CH$_2$)$_{o4}$—, —(CH$_2$)$_{o1}$—O—(CH$_2$)$_{o4}$—, —(CH$_2$)$_{o1}$—NH—(CH$_2$)$_{o4}$—, —(CH$_2$)$_{o1}$—NAc—(CH$_2$)$_{o4}$—, —(CH$_2$)$_{o1}$—C(O)—(CH$_2$)$_{o4}$—, —(CH$_2$)$_{p1}$—, —(CR$^7$R$^8$)$_{p1}$—, —(CH$_2$—CH$_2$—O)$_{p1}$—, —O—, —S—, —NH—, —C(O)—, —NH—C(O)—NH—, —NH—C(O)—(CH$_2$)$_{p2}$—, —C(O)—NH—(CH$_2$)$_{p2}$—, —NH—C(O)—C$_2$H$_4$—C(O)—NH—, —C(O)—NH—, —C(O)—NH—(CH$_2$—CH$_2$—O)$_{p1}$—C$_2$H$_4$—, —C(O)—NH—(CH$_2$—CH$_2$—O)$_{p1}$—, —(CH$_2$)$_{q1}$—, —(CR$^{16}$R$^{17}$)$_{q1}$—, —(CH$_2$)$_{q1}$—NH—C(O)—, —(CH$_2$)$_{q1}$—C(O)—NH—,

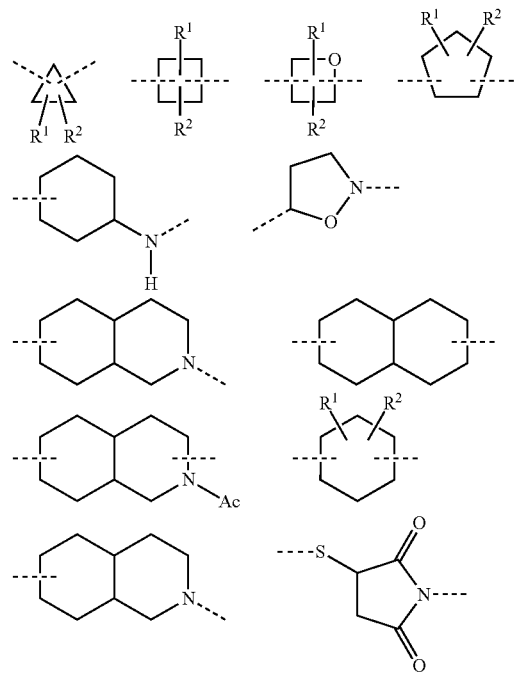

-continued

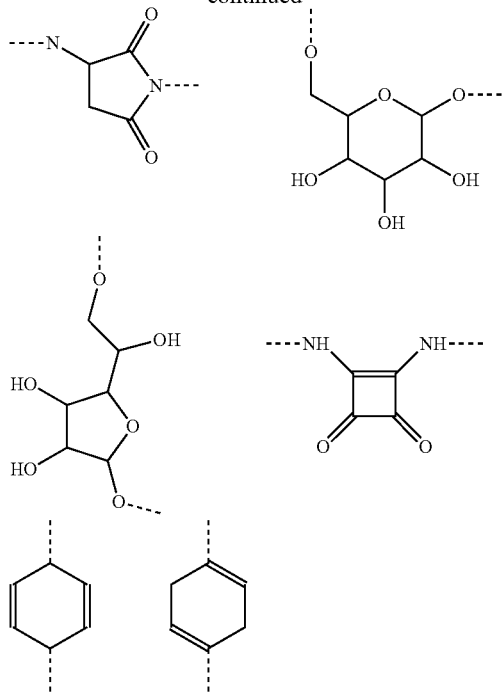

wherein not two heteroatoms of the above-mentioned residues are linked together, such as a group —S— is not linked to a group —NH—C(O)—NH—;

p2, o2, o3 are integers selected independently of each other from: 0, 1, 2, 3, 4, 5, 6, 7, 8, 9, 10;

p1, q1, o1, o4 are integers selected independently of each other from: 1, 2, 3, 4, 5, 6, 7, 8, 9, 10;

and $R^1$, $R^2$, $R^7$, $R^8$, $R^{16}$, and $R^{17}$ represent independently of each other —H, —OCH$_3$, —OC$_2$H$_5$, —CH$_3$, —C$_2$H$_5$, —C$_3$H$_7$, —CH(CH$_3$)$_2$, —F, —CH$_2$F, —CF$_2$H, —CF$_3$, —C(O)—NH$_2$, —SCH$_3$, —SC$_2$H$_5$, —NHAc, —NH(CH$_3$), —NH(C$_2$H$_5$), —N(CH$_3$)$_2$, —N(C$_2$H$_5$)$_2$, —NH—C(O)—CH$_3$, and —C(O)—CH$_3$.

The linker -A- according to the present invention represents:

-$A^a$-$A^b$-$A^c$-$A^d$- or -$A^a$-$A^b$-$A^d$- or -$A^a$-$A^d$- or -$A^a$-;

wherein $A^a$ represents —(CH$_2$)$_{o1}$—, —(CR$^1$R$^2$)$_{o1}$—, —(CR$^1$R$^2$)$_{o1}$—(CR$^3$R$^4$)$_{o2}$—, —(CR$^1$R$^2$)$_{o1}$—(CR$^3$R$^4$)$_{o2}$—(CR$^5$R$^6$)$_{o3}$—, —(CR$^1$R$^2$)$_{o3}$—(CH$_2$—CH$_2$—O)$_{o2}$—(CR$^3$R$^4$)$_{o1}$—, —(CH$_2$—CH$_2$—O)$_{o2}$—(CR$^1$R$^2$)$_{o3}$—(CR$^3$R$^4$)$_{o1}$—, —(CR$^1$R$_2$)$_{o1}$—(CR$^3$R$^4$)$_{o2}$—S—(CR$^5$R$^6$)$_{o4}$—, —(CR$^1$R$^2$)$_{o1}$—(CR$^3$R$^4$)$_{o2}$—O—(CR$^5$R$^6$)$_{o4}$—, —(CR$^1$R$^2$)$_{o1}$—(CR$^3$R$^4$)$_{o2}$—NH—(CR$^5$R$^6$)$_{o4}$—, —(CR$^1$R$^2$)$_{o1}$—S—(CR$^3$R$^4$)$_{o4}$—, —(CR$^1$R$^2$)$_{o1}$—S—(CR$^5$R$^6$)$_{o3}$—(CR$^3$R$^4$)$_{o4}$—, —(CR$^1$R$^2$)$_{o1}$—O—(CR$^3$R$^4$)$_{o4}$—, —(CR$^1$R$^2$)$_{o1}$—O—(CR$^5$R$^6$)$_{o3}$—(CR$^3$R$^4$)$_{o4}$—, —(CR$^1$R$^2$)$_{o1}$—NH—(CR$^3$R$^4$)$_{o4}$—, —(CR$^1$R$^2$)$_{o1}$—NH—(CR$^5$R$^6$)$_{o3}$—(CR$^3$R$^4$)$_{o4}$—, —(CR$^1$R$^2$)$_{o1}$—C(O)—(CR$^3$R$^4$)$_{o4}$—, —(CR$^1$R$^2$)$_{o1}$—C(O)—(CR$^5$R$^6$)$_{o3}$—(CR$^3$R$^4$)$_{o4}$—,

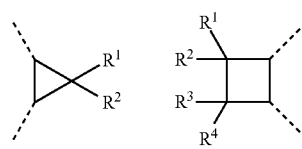

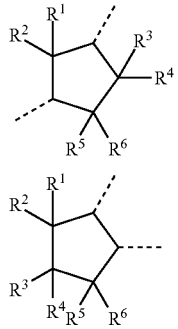
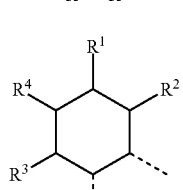
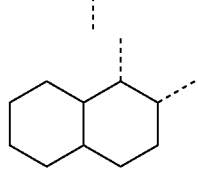

$A^b$ represents —C$_2$)$_{p1}$—, —C$^7$R$^8$)$_{p1}$—, —(CH$_2$—CH$_2$—O)$_{p1}$—, —(C$^7$R$^8$)$_{p1}$—S—(CR$^9$R$^{10}$)$_{p2}$—, —(CR$^7$R$^8$)$_{p1}$—O—(CR$^9$R$^{10}$)$_{p2}$—, —(CR$^7$R$^8$)$_{p1}$—NH—(CR$^9$R$^{10}$)$_{p2}$—, —O—, —S—, —NH—, —C(O)—, —NH—C(O)—NH—, —NH—C(O)—(CH$_2$)$_{p2}$—, —C(O)—NH—(CH$_2$)$_{p2}$—, —NH—C(O)—C$_2$H$_4$—C(O)—NH—, —(CR$^7$R$^8$)$_{p1}$—(CR$^9$R$^{10}$)$_{p2}$—(CH$_2$CH$_2$—O)$_{p3}$—, —(CR$^7$R$^8$)$_{p1}$—(CH$_2$CH$_2$—O)$_{p2}$—(CR$^9$R$_{10}$)$_{p3}$—, —(CH$_2$—CH$_2$—O)$_{p1}$—(CR$^7$R$^8$)$_{p2}$—(CR$^9$R$^{10}$)$_{p3}$—, —C(O)—NR$^{15}$—, —(CR$^7$R$^8$)$_{p1}$—(CR$^9$R$^{10}$)$_{p2}$—(CR$^{11}$R$^{12}$)$_{p3}$, —C(O)—NH—CH(R$^{18}$)—, —C(O)—NH—CH(R$^{18}$)—C(O)—NH—CH(R$^{19}$)—, —C(O)—NH—(CH$_2$—CH$_2$—O)$_{p1}$—C$_2$H$_4$—, —C(O)—NH—(CH$_2$—CH$_2$—O)$_{p1}$—,

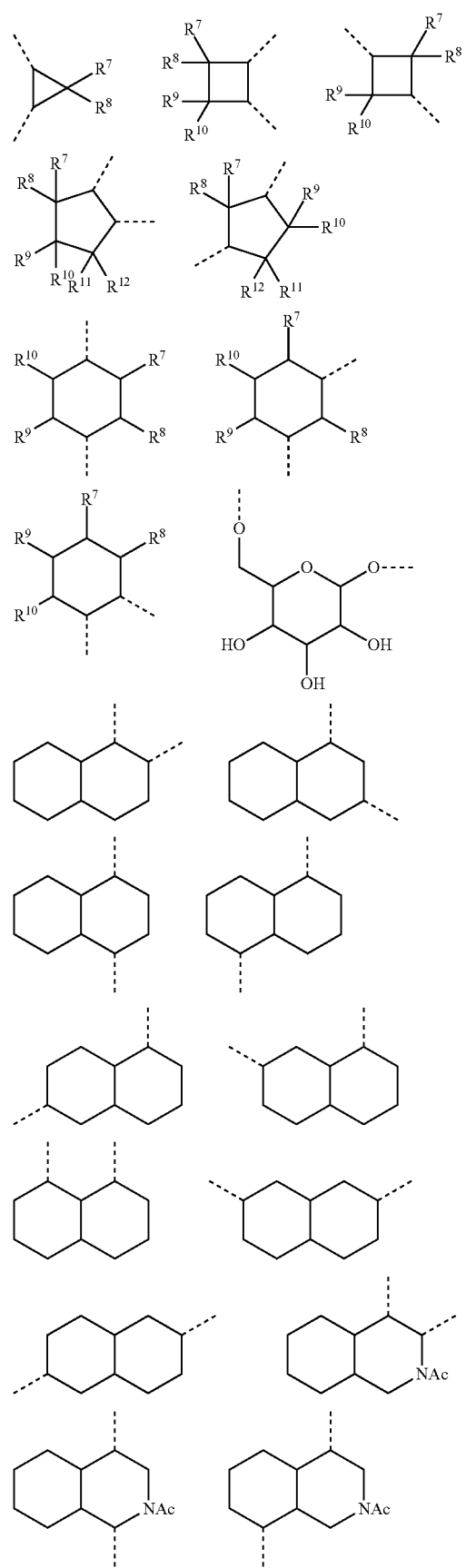
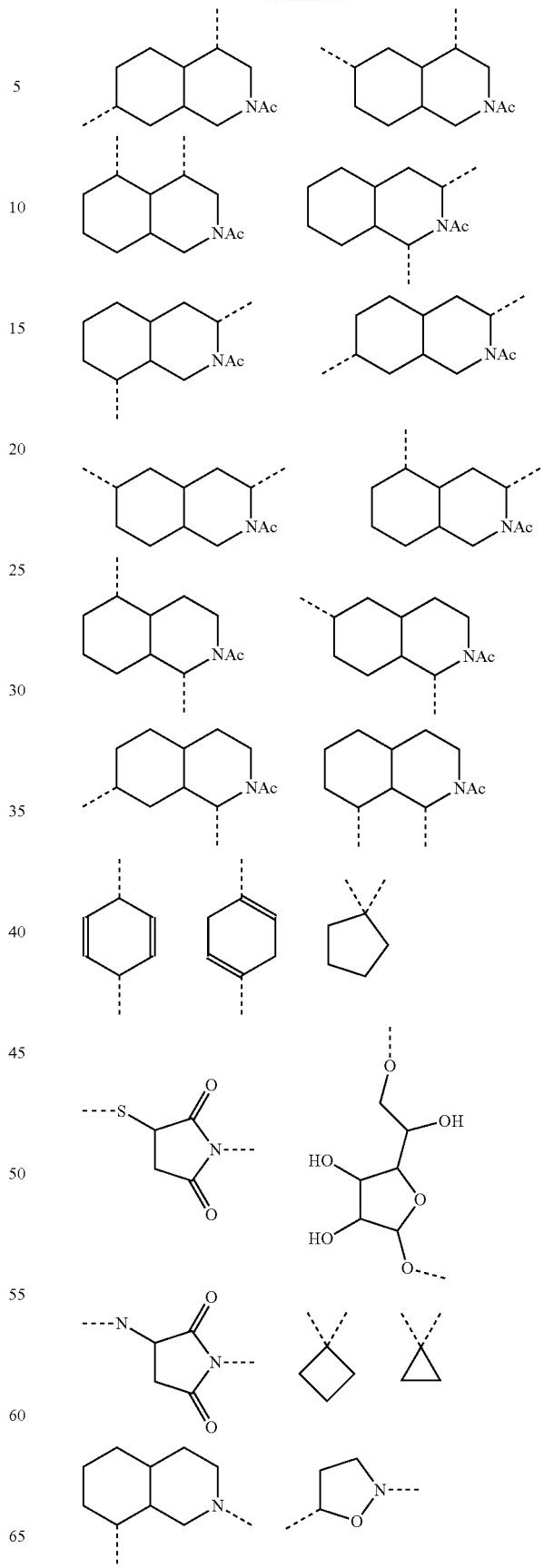

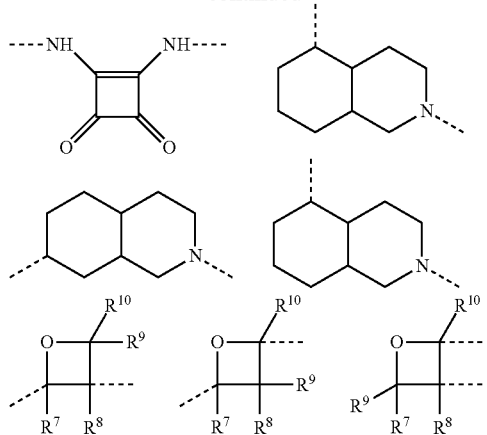

$A^c$ represents $(CH_2)_{q1}$—, —$(CR^{16}R^{17})_{q1}$—, $(CH_2)_{q1}$—NH—C(O)—, $(CH_2)_{q1}$—C(O)—NH—,

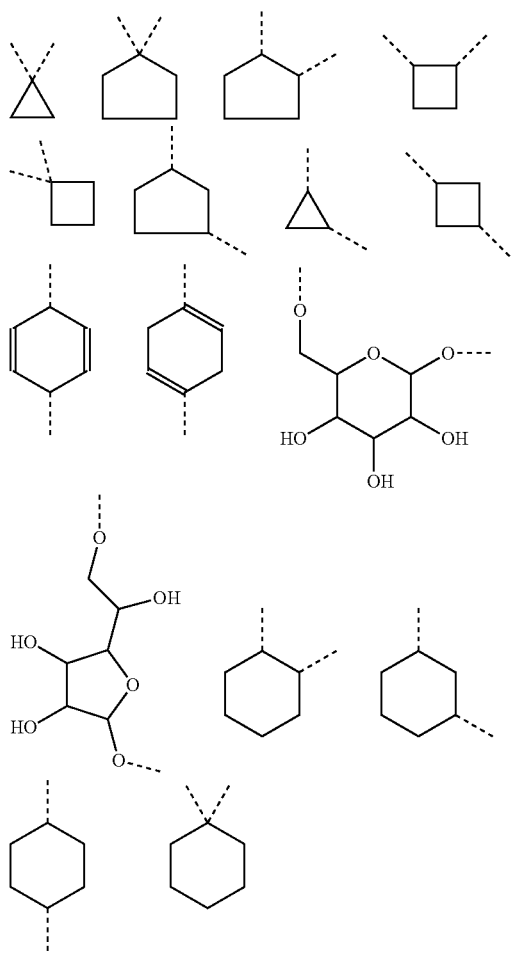

$A^d$ represents —$(CH_2)_{m1}$—, —$(CR^{13}R^{14})_{m1}$—, —$CH_2$—$S(CH_2)_{m1}$—, —$CH_2$—$O(CH_2)_{m1}$—, —$CH_2$—C(O)—$(CH_2)_{m1}$—, —$(CH_2$—$CH_2$—$O)_{m1}$—$(CR^{13}R^{14})_{m2}$—, —$(CH_2)_{m1}$—$(CR^{13}R^{14})_{m2}$—, —$(CR^{13}R^{14})_{m2}$—$(CH_2)_{m1}$—, —$(CR^{13}R^{14})_{m1}$—$(CH_2)_{m2}$—, —$(CH_2)_{m2}$—(O—$CH_2$—$CH_2)_{m1}$—,

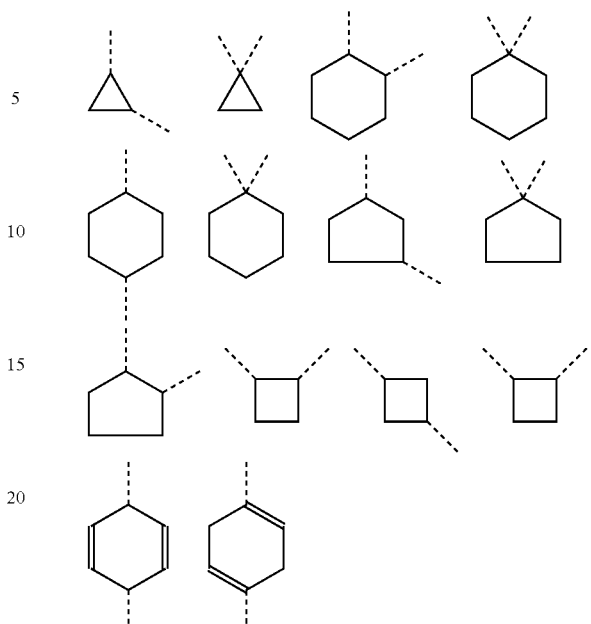

$R^1$-$R^{14}$, $R^{16}$ and $R^{17}$ represent independently of each other —H, —$OCH_3$, —$OC_2H_5$, —$OC_3H_7$, -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$, —$CH_2$-cyclo-$C_6H_{11}$, —C(cyclo-$C_6H_{11})_3$, —$CH_3$, —$C_2H_5$, —$C_3H_7$, —$CH(CH_3)_2$, —$C_4H_9$, —$CH_2$—CH$(CH_3)_2$, —CH$(CH_3)$—$C_2H_5$, —C$(CH_3)_3$, —$C_5H_{11}$, —CH$(CH_3)$—$C_3H_7$, —$CH_2$—CH$(CH_3)$—$C_2H_5$, —CH$(CH_3)$—CH$(CH_3)_2$, —C$(CH_3)_2$—$C_2H_5$, —$CH_2$—C$(CH_3)_3$, —CH$(C_2H_5)_2$, —$C_2H_4$—CH$(CH_3)_2$, —$C_6H_{13}$, —$C_3H_6$—CH$(CH_3)_2$, —$C_2H_4$—CH$(CH_3)$—$C_2H_5$, —CH$(CH_3)$—$C_4H_9$, —$CH_2$—CH$(CH_3)$—$C_3H_7$, —CH$(CH_3)$—$CH_2$—CH$(CH_3)_2$, —CH$(CH_3)$—CH$(CH_3)$—$C_2H_5$, —$CH_2$—CH$(CH_3)$—CH$(CH_3)_2$, —$CH_2$—C$(CH_3)_2$—$C_2H_5$, —C$(CH_3)_2$—$C_3H_7$, —C$(CH_3)_2$—CH$(CH_3)_2$, —$C_2H_4$—C$(CH_3)_3$, —CH$(CH_3)$—C$(CH_3)_3$, —$C_7H_{15}$, —$C_8H_{17}$, —$C_6H_4$—$OCH_3$, —$CH_2$—$CH_2$—$OCH_3$, —$CH_2$—$OCH_3$, —$CH_2$—$C_6H_4$—$OCH_3$, —F, —$CH_2F$, —$CF_2H$, —$CF_3$, —C(O)—$NHR^{15}$, —C(O)—$NHR^{22}$, —C(O)—$NHR^{23}$, —C(O)—$NHR^{24}$, —C(O)—$NHR^{25}$, —$SCH_3$, —$SC_2H_5$, —$NR^{15}R^{22}$, —$NHR^{15}$, —$NHR^{22}$, —$NHR^{23}$, —$NHR^{24}$, —$NHR^{25}$, —NH—C(O)—$R^{15}$, —NH—C(O)—$R^{22}$, —NH—C(O)—$R^{23}$, —NH—C(O)—$R^{24}$, —NH—C(O)—$R^{25}$, —C(O)—$R^{15}$, —C(O)—$R^{22}$, —C(O)—$R^{23}$, —C(O)—$R^{24}$, —C(O)—$R^{25}$.

$R^{15}$, $R^{22}$, $R^{23}$, $R^{24}$ and $R^{25}$ represents: —$CH_3$, —$O_2H_5$, —$C_3H_7$, —CH$(CH_3)_2$, —$C_4H_9$, —$CH_2$—CH$(CH_3)_2$, —CH$(CH_3)$—$C_2H_5$, —C$(CH_3)_3$, —$C_5H_{11}$, —CH$(CH_3)$—$C_3H_7$, —$CH_2$—CH$(CH_3)$—$C_2H_5$, —CH$(CH_3)$—CH$(CH_3)_2$, —C$(CH_3)_2$—$C_2H_5$, —$CH_2$—C$(CH_3)_3$, —CH$(C_2H_5)_2$, —$C_2H_4$—CH$(CH_3)_2$, —$C_6H_{13}$, —$C_3H_6$—CH$(CH_3)_2$, —$C_2H_4$—CH$(CH_3)$—$C_2H_5$, —CH$(CH_3)$—$C_4H_9$, —$CH_2$—CH$(CH_3)$—$C_3H_7$, —CH$(CH_3)$—$CH_2$—CH$(CH_3)_2$, —CH$(CH_3)$—CH$(CH_3)$—$C_2H_5$, —$CH_2$—CH$(CH_3)$—CH$(CH_3)_2$, —$CH_2$—C$(CH_3)_2$—$C_2H_5$, —C$(CH_3)_2$—$C_3H_7$, —C$(CH_3)_2$—CH$(CH_3)_2$, —$C_2H_4$—C$(CH_3)_3$;

$R^{18}$, $R^{19}$, $R^{20}$ and $R^{21}$ represent independently of each other —$CH_2$—$OCH_3$, —$CH_2$—$SCH_3$, —$CH_2$—$SeCH_3$, —$C_2H_4$—$OCH_3$, —$C_2H_4$—$SCH_3$, —$C_2H_4$—$SeCH_3$, —H —$CH_3$, —$C_2H_5$, —$C_3H_7$, —$CH(CH_3)(OCH_3)$, —CH $(CH_3)_2$, —$CH_2$—$CH(CH_3)_2$, —$CH_2$-Ph, —$CH_2$—$CH(CH_3)$ $(C_2H_5)$, —$CH_2$—C(O)—$NH_2$, —$C_2H_4$—C(O)—$NH_2$, —$CH_2$-p-$C_6H_4$—$OCH_3$;

p2, p3, o2, o3 are integers selected independently of each other from: 0, 1, 2, 3, 4, 5, 6, 7, 8, 9, 10;

p1, q1, o1, o4, m1, m2 are integers selected independently of each other from: 1, 2, 3, 4, 5, 6, 7, 8, 9, 10.

Preferably the linker A represents the residue -$A^a$-.

-$A^a$- is preferably a linear carbon chain or a saturated carbocycle selected from

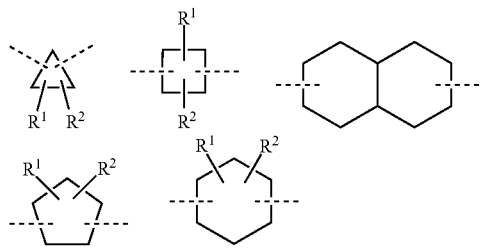

Also preferably the linker A represents —$(CH_2)_{o1}$-$A^b$-$A^c$-$A^d$-, —$(CH_2)_{o1}$-$A^b$-$A^d$-, —$(CH_2)_{o1}$-$A^d$-, —$(CR^1R^2)_{o1}$-$A^b$-$A^c$-$A^d$-, —$(CR^1R^2)_{o1}$-$A^b$-$A^d$-, or —$(CR^1R^2)_{o1}$-$A^d$-, wherein $A^b$, $A^c$ and $A^d$ have the meanings as defined herein and $R^1$ and $R^2$ have the meanings as defined herein and preferably represent independently of each other —H, —$OCH_3$, —$OC_2H_5$, —$CH_3$, —$C_2H_5$, —$C_3H_7$, —$CH(CH_3)_2$, —F, —$CH_2F$, —$CF_2H$, —$CF_3$, —C(O)—$NH_2$, —$SCH_3$, —$SC_2H_5$, —NHAc, —$NH(CH_3)$, —$NH(C_2H_5)$, —N $(CH_3)_2$, —$N(C_2H_5)_2$, —NH—C(O)—$CH_3$, and —C(O)—$CH_3$.

$A^b$ represents in general and especially in the aforementioned general formula —$(CH_2)_{o1}$-$A^b$-$A_c$-$A^d$-, —$(CH_2)_{o1}$-$A^b$-$A^d$-, —$(CR^1R^2)_{o1}$-$A^b$-$A^c$-$A^d$-, —$(CR^1R^2)_{o1}$-$A^b$-$A^d$-preferably one of the following residues: —O—, —S—, —NH—, —C(O)—, —NH—C(O)—NH—, —NH—C(O)—$(CH_2)_{p2}$—, —C(O)—NH—$(CH_2)_{p2}$—, —NH—C(O)—$C_2H_4$—C(O)—NH—, —C(O)—$NR^{15}$—, —C(O)—NH—$CH(R^{18})$—, —C(O)—NH—$(CH_2$—$CH_2$—$O)_{p1}$—$C_2H_4$—, —C(O)—NH—$(CH_2$—$CH_2$—$O)_{p1}$—, wherein the substituents $R^{15}$ and $R^{18}$ have the meanings as defined herein and preferably —$CH_3$, —$C_2H_5$, or —$C_3H_7$.

$A^c$ represents in general and especially in the aforementioned general formula —$(CH_2)_{o1}$-$A^b$-$A^c$-$A^d$- and —$(CR^1R^2)_{o1}$-$A^b$-$A^c$-$A^d$- preferably one of the following residues: —$(CH_2)_{q1}$—,

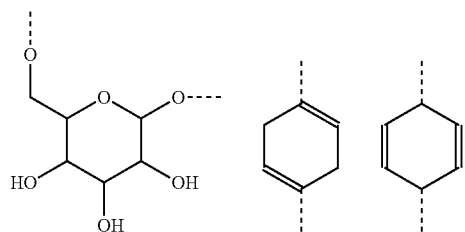

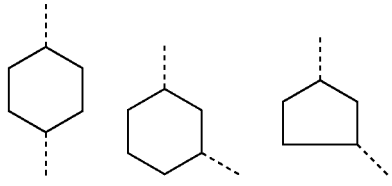

$A^d$ represents in general and especially in the aforementioned general formula —$(CH_2)_{o1}$-$A^b$-$A^c$-$A^d$-, —$(CH_2)_{o1}$-$A^b$-$A^d$-, —$(CH_2)_{o1}$-$A^d$-, —$(CR^1R^2)_{o1}$-$A^b$-$A^c$-$A^d$-, —$(CR^1R^2)_{o1}$-$A^b$-$A^d$-, and —$(CR^1R^2)_{o1}$-$A^d$- preferably one of the following residues:

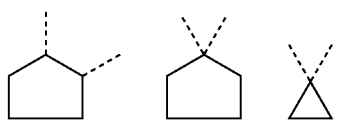

—$(CH_2)_{m1}$—

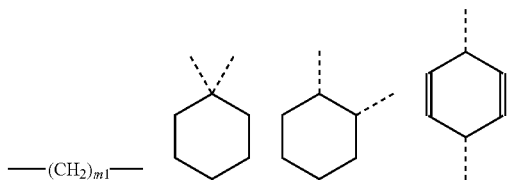

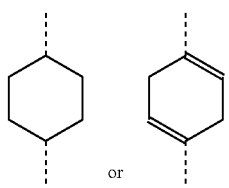

or

The function of the linker alone or together with the interconnecting molecule is to covalently connect the reducing-end of the saccharides to an immunogenic carrier or to a solid support. An interconnecting molecule according to the present invention refers to a bifunctional molecule containing functional group X and functional group Y, wherein functional group X is capable of reacting with the terminal thiol group on the linker A and the functional group Y is capable of binding to an immunogenic carrier or to a solid support. Thus, the present invention refers to saccharides of the formula (I), wherein the linker per se or together with the interconnecting molecule is capable of establishing, keeping and/or bridging a special distance between the reducing-end monosaccharide and an immunogenic carrier or a solid support.

In a preferred embodiment according to the present invention the linker -A- represents -$A^a$-$A^b$-$A^c$-$A^d$-. Preferably, the fragment -$A^c$-$A^b$-$A^c$-$A^d$- is selected from the following fragments:

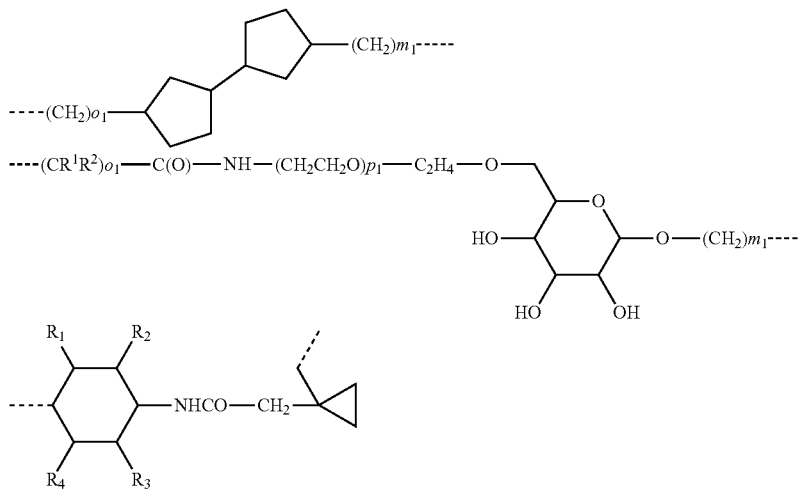

Another preferred embodiment is directed to saccharides of general formula (I), wherein the linker -A- represents -$A^a$-$A^b$-$A^d$-. Preferably, fragment -$A^a$-$A^b$-$A^d$- is selected from:

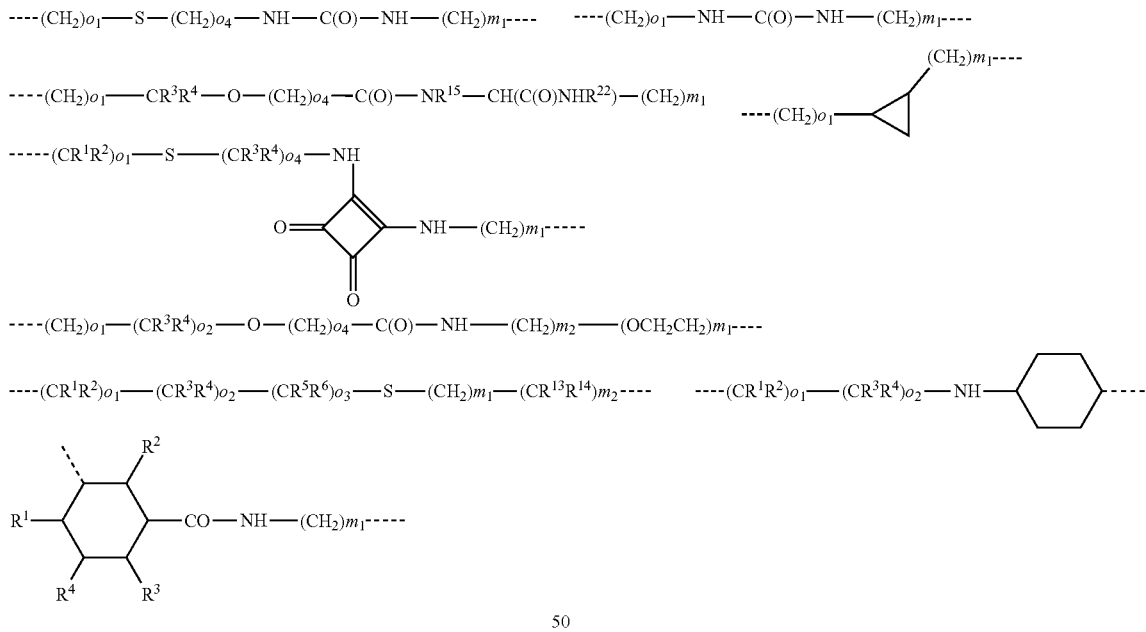

Preferably the linker A represents -$A^a$-$A^d$-, and more preferably fragment -$A^a$-$A^d$- is selected from

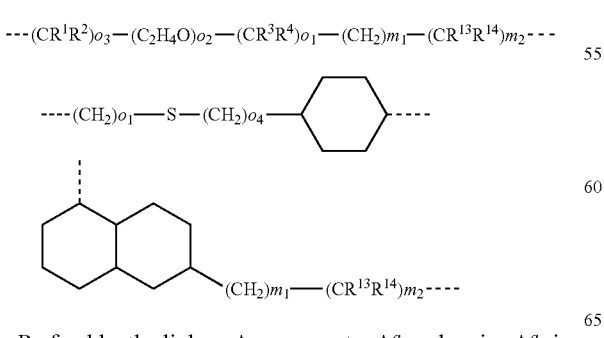

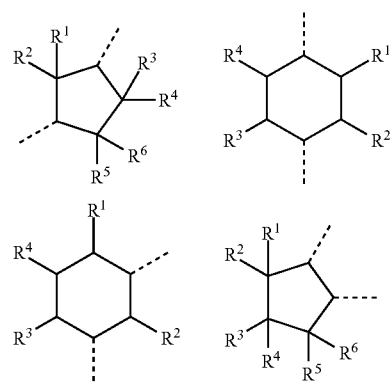

Preferably, the linker -A- represents -$A^a$-, wherein -$A^a$- is selected from:

-continued

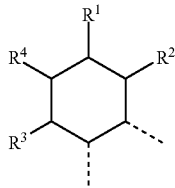

—(CH$_2$)$_{o1}$—, —(CR$^1$R$^2$)$_{o1}$—, —(CR$^1$R$^2$)$_{o3}$—(CH$_2$—CH$_2$—O)$_{o2}$—(CR$^3$R$^4$)$_{o1}$—, —(CR$^1$R$^2$)$_{o1}$—(CR$^3$R$^4$)$_{o2}$—(CR$^5$R$^6$)$_{o3}$, —(CH$_2$—CH$_2$—O)$_{o2}$—(CR$^1$R$^2$)$_{o3}$—(CR$^3$R$^4$)$_{o1}$—, —(CH$_2$)$_{o1}$—(CR$^3$R$^4$)$_{o2}$—S—(CH$_2$)$_{o4}$—, —(CH$_2$)$_{o1}$—(CR$^3$R$^4$)$_{o2}$—O—(CH$_2$)$_{o4}$—, —(CH$_2$)$_{o1}$—(CR$^3$R$^4$)$_{o2}$—NH—(CH$_2$)$_{o4}$—, —(CR$^1$R$^2$)$_{o1}$—S—(CR$^3$R$^4$)$_{o4}$, —(CR$^1$R$^2$)$_{o1}$—O—(CR$^3$R$^4$)$_{o4}$, —(CR$^1$R$^2$)$_{o1}$—NH—(CR$^3$R$^4$)$_{o4}$, or —(CR$^1$R$^2$)$_{o1}$—C(O)—(CR$^3$R$^4$)$_{o4}$.

In a preferred embodiment, substituents R$^1$-R$^{14}$, R$^{16}$ and R$^{17}$ are selected from: —H, —OCH$_3$, —OC$_2$H$_5$, —CH$_3$, —C$_2$H$_5$, —C$_3$H$_7$, —F, —CH$_2$F, —CF$_2$H, —CF$_3$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —CH$_2$—CH$_2$—OCH$_3$, —CH$_2$—OCH$_3$, —SCH$_3$, —SC$_2$H$_5$, —NR$^{15}$R$^{22}$, —NHR$^{15}$, —NHR$^{22}$, —NHR$^{23}$, —NHR$^{24}$, —NHR$^{25}$, —NH—C(O)—R$^{15}$, —NH—C(O)—R$^{22}$, —NH—C(O)—R$^{23}$, —NH—C(O)—R$^{24}$, —NH—C(O)—R$^{25}$.

Even more preferred are linkers, wherein -A- represents -A$^a$-. Preferably, fragment -A$^a$- has the meaning: —(CH$_2$)$_{o1}$—, —(CR$^1$R$^2$)$_{o1}$—, —(CH$_2$)$_{o1}$—(CR$^3$R$^4$)$_{o2}$—(CH$_2$)$_{o3}$, —(CH$_2$—CH$_2$—O)$_{o2}$—(CH$_2$)$_{o1}$—, —(CH$_2$—CH$_2$—O)$_{o2}$—(CR$^1$R$^2$)—(CH$_2$)$_{o1}$—, —(CH$_2$)$_{o1}$—(CR$^3$R$^4$)$_{o2}$—S—(CH$_2$)$_{o4}$, —(CR$^1$R$^2$)$_{o1}$—S—(CH$_2$)$_{o4}$, —(CH$_2$)$_{o1}$—(CR$^3$R$^4$)$_{o2}$—O—(CH$_2$)$_{o4}$, —(CR$^1$R$^2$)$_{o1}$—O—(CH$_2$)$_{o4}$, or —(CR$^1$R$^2$)$_{o1}$—C(O)—(CR$_3$R$^4$)$_{o4}$,

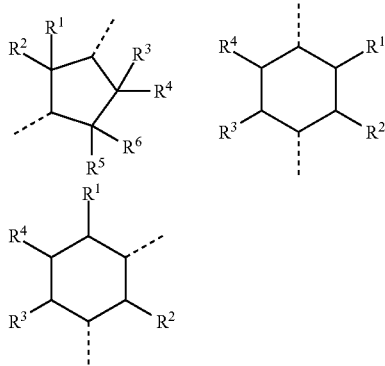

wherein
o1 and o4 are integers selected from 1, 2, 3, 4, 5, 6;
o2 and o3 are integers selected from 0, 1, 2, 3, 4, 5, 6;
and, substituents R$^1$-R$^6$ are selected from:
—H, —OCH$_3$, —OC$_2$H$_5$, —CH$_3$, —C$_2$H$_5$, —C$_3$H$_7$, —F, —CH$_2$F, —CF$_2$H, —CF$_3$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —CH$_2$—CH$_2$—OCH$_3$, —CH$_2$—OCH$_3$, —SCH$_3$, —SC$_2$H$_5$, —NHR$^{15}$, —NHR$^{22}$, —NHR$^{23}$, —NHR$^{24}$, —NHR$^{25}$, —NH—C(O)—R$^{15}$, —NH—C(O)—R$^{22}$, —NH—C(O)—R$^{23}$, —NH—C(O)—R$^{24}$, —NH—C(O)—R$^{25}$.

The linker A according to the current invention can be easily accessed by the person skilled in the art following procedures described in the literature.

Further, the present invention refers to synthetic saccharides of the formula (I), wherein the linker is a molecular fragment capable of connecting the reducing-end monosaccharide of saccharides of general formula (I) via the thiol group with an immunogenic carrier or a solid support, optionally by binding to at least one further interconnecting molecule. More specifically, one extremity of the linker is connected to the exocyclic oxygen atom at the anomeric center of the reducing-end monosaccharide and the other extremity is connected via the sulfur atom with the interconnecting molecule, or directly with the immunogenic carrier or the solid support.

The compounds of the present invention bear basic and/or acidic substituents and they may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples of suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of an acid, selected out of the group mentioned above.

Further, it is also possible that the compounds of the present invention bear simultaneously basic and acid groups. Further, it may also occur that these basic and acid groups appear to be in close vicinity to one another enabling an intramolecular proton transfer from the acidic group to the basic group. Therefore, in a preferred embodiment of the present invention the compound of the formula (I) may be zwitter-ionic, bearing at least e.g. one —O$^-$ and one —NH$_3^+$ group.

Thus, the present invention relates to saccharides of general formula (I):

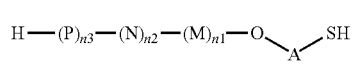

wherein A is a linker;

M, N and P represent independently of each other one of the following sugar fragments:

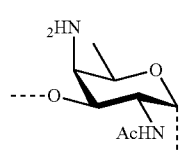

-continued

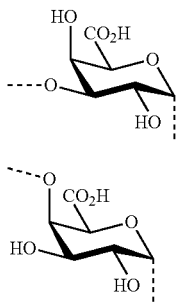
S2

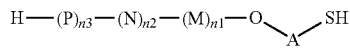
S3 wherein each sugar fragment S1, S2, and S3 is not more than once present in the general formula (I), and if sugar fragment S1 is present then its anomeric carbon can be linked only to —O-A-SH or to the oxygen atom at position 4 of sugar fragment S3, and if sugar fragment S2 is present, then its anomeric carbon is linked only to —O-A-SH or to the oxygen atom at position 3 of sugar fragment S1, and if sugar fragment S3 is present then its anomeric carbon can be linked only to —O-A-SH or to the oxygen atom at position 3 of sugar fragment S2;

n1, n2 and n3 are integers selected from 0 and 1, wherein at least one of the integers n1, n2 and n3 is 1 and pharmaceutically acceptable salts of these saccharides.

The same connections as disclosed herein for the saccharides of general formula (I) apply also to the disulfides (i.e. the dimeric saccharides) of general formula (II) named herein as intermediates.

Thus, included under the scope of the present invention are trisaccharides of general formula: H—(S1)-(S3)-(S2)-O-A-SH, H—(S2)-(S1)-(S3)-O-A-SH, H—(S3)-(S2)-(S1)-O-A-SH; disaccharide of general formula: H—(S1)-(S3)-O-A-SH, H—(S3)-(S2)-O-A-SH, H—(S2)-(S1)-O-A-SH, and monosaccharides of general formula: H—(S1)-O-A-SH, H—(S3)-O-A-SH, wherein A is defined as a linker.

A preferred embodiment of the present application is directed to saccharides of general formula (I)

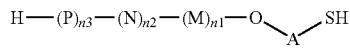 (I)

wherein A is a linker defined as above,
P represents S1,
N represents S3,
M represents S2,
sugar fragments S1, S2, S3 are connected to the each other and to —O-A-SH fragment via O-glycosidic bonds, sugar fragment S2 cannot be connected to the sugar fragment S1, and n1, n2 and n3 are integers selected from 0 and 1, wherein at least one of the integers n1, n2 and n3 is 1 and pharmaceutically acceptable salts of these saccharides.

In other words, preferred saccharides of the present invention are saccharides of general formula (I)

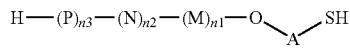 (I)

wherein A is a linker defined as above,
P represents S1,
N represents S3,
M represents S2,
sugar fragments S1, S2, S3 are connected to the each other and to —O-A-SH fragment via O-glycosidic bonds and n1=n2=n3=1, or n1=n2=1 and n3=0, or n1=1 and n2=n3=0, or n1=0 and n2=n3=1, or n1=n2=0 and n3=1.

In yet another preferred embodiment of the present invention, the compound according to the general formula (I) is selected from the group comprising or consisting of:

2-mercaptoethanyl O-(2-acetamido-4-amino-2,4,6-trideoxy-α-D-galactopyranosyl)-(1→4)-O-(α-D-galactopyranosyluronate)-(1→3)-O-(α-D-galactopyranosyluronate);

2-mercaptoethanyl O-(α-D-galactopyranosyluronate)-(1→3)-O-(2-acetamido-4-amino-2,4,6-trideoxy-α-D-galactopyranosyl)-(1→4)-O-(α-D-galactopyranosyluronate);

2-mercaptoethanyl O-(α-D-galactopyranosyluronate)-(1→3)-O-(α-D-galactopyranosyluronate)-(1→3)-O-(2-acetamido-4-amino-2,4,6-trideoxy-α-D-galactopyranoside);

2-mercaptoethanyl O-(α-D-galactopyranosyluronate)-(1→3)-O-(α-D-galactopyranosyluronate);

2-mercaptoethanyl O-(2-acetamido-4-amino-2,4,6-trideoxy-α-D-galactopyranosyl)-(1→4)-O-(α-D-galactopyranosyluronate);

2-mercaptoethanyl O-(α-D-galactopyranosyluronate);

2-mercaptoethanyl O-(α-D-galactopyranosyluronate)-(1→3)-O-(2-acetamido-4-amino-2,4,6-trideoxy-α-D-galactopyranoside);

2-mercaptoethanyl O-(2-acetamido-4-amino-2,4,6-trideoxy-α-D-galactopyranoside)

Chemical Synthesis

Another aspect of the present invention relates to the synthesis of saccharides of general formula (I):

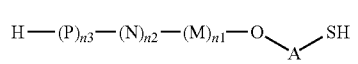 (I)

wherein A is a linker;
M, N and P represent independently of each other one of the following sugar fragments:

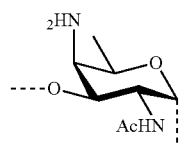
S1

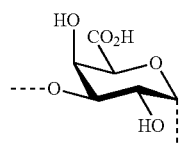
S2

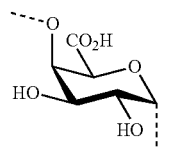
S3 wherein sugar fragments S1, S2, S3 are connected to each other and to —O-A-SH fragment via O-glycosidic bonds, each sugar fragment S1, S2, and S3 is not more than once present in the general formula (I), sugar fragment S1 cannot be simultaneously connected to —O-A-SH and sugar fragment S3, sugar fragment S3 cannot be simultaneously connected to —O-A-SH and sugar fragment S2, sugar fragment S2 cannot be simultaneously connected to —O-A-SH and sugar fragment S1, and n1, n2 and n3 are integers selected from 0 and 1, wherein at least one of the integers n1, n2 and n3 is 1 and comprising the steps:

A1) Reacting the compound 2 of the formula:

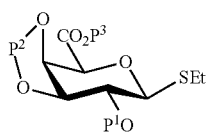

2 wherein $P^1$-$P^3$ represent protecting groups,
with the compound 3 of the formula:

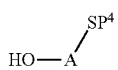

3 wherein $P^4$ represents a protecting group, in order to obtain compound 4 of general formula:

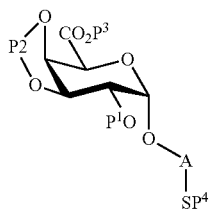

4 wherein $P^1$-$P^4$ and A are defined as above;
and performing removal of protecting groups $P^1$-$P^4$ on compound 4 to afford monosaccharide disulfide 5 of general formula:

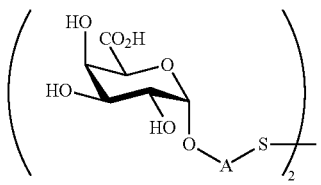

5 wherein A is defined as above, and wherein monosaccharide disulfide 5 is further treated with a reducing agent to afford monosaccharide 6 of general formula:

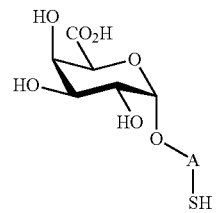

6

(H—S2—O—A—SH)

wherein A is defined as above;
or performing selective deprotection on compound 4 to afford compound 7 of general formula

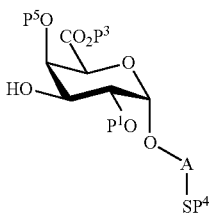

7 wherein $P^5$ is a protecting group and $P^1$, $P^3$, $P^4$ and A are defined as above.

or

A2) Reacting compound 8 of general formula

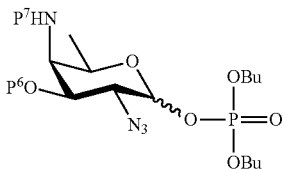

8 wherein $P^6$ and $P^7$ represent protecting groups, with compound 3 to afford compound 9 of general formula

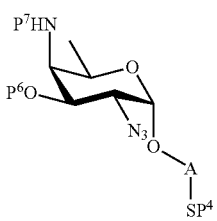

9 wherein $P^6$, $P^7$ and A are defined as above;
and performing conversion of the azido group to acetamido group and removal of the protecting groups $P^4$, $P^6$ and $P^7$ on compound 9 to afford monosaccharide disulfide 10 of general formula:

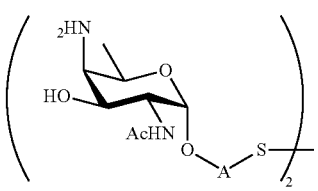

10 wherein A is defined as above, and wherein monosaccharide disulfide 10 is further treated with a reducing agent to afford monosaccharide 11 of general formula:

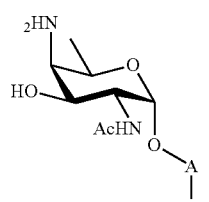

11

(H—S1—O—A—SH)

wherein A is defined as above;

or performing selective deprotection on compound 9 to afford compound 12 of general formula:

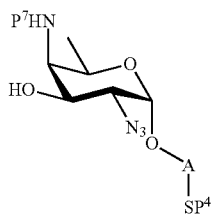
12 wherein $P^4$, $P^7$ and A are defined as above.

or

A3) Reacting compound 13 of general formula

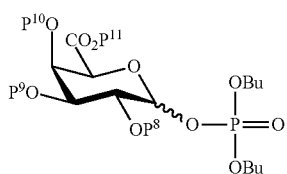
13 wherein $P^8$-$P^{11}$ represent protecting groups, with compound 3 to afford compound 14 of general formula:

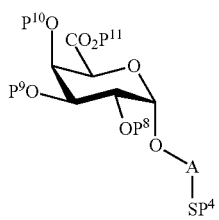
14 wherein $P^4$, $P^8$-$P^{11}$ are defined as above and performing selective deprotection of compound 14 to afford compound 15 of general formula:

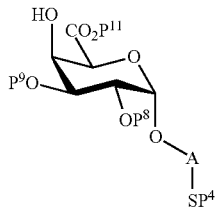
15 wherein $P^4$, $P^8$, $P^9$, $P^{11}$ and A are defined as above.

and

B1) Reacting compound 7 with compound 13 to afford compound 16 of general formula:

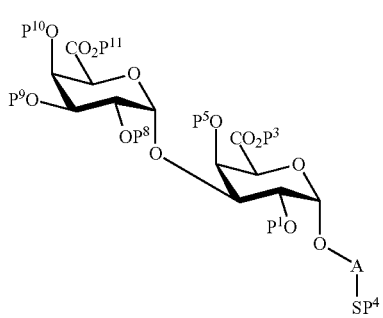
16 wherein $P^1$, $P^3$-$P^5$, $P^8$-$P^{11}$ and A are defined as above;

and performing removal of protecting groups $P^1$, $P^3$-$P^5$, $P^8$-$P^{11}$ on compound 16 to afford disaccharide disulfide 17 of general formula:

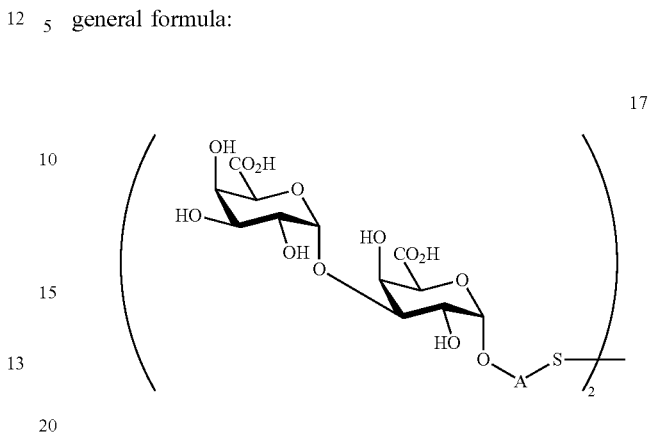
17 wherein A is defined as above and wherein disaccharide disulfide 17 is further treated with a reducing agent to afford disaccharide 18 of general formula:

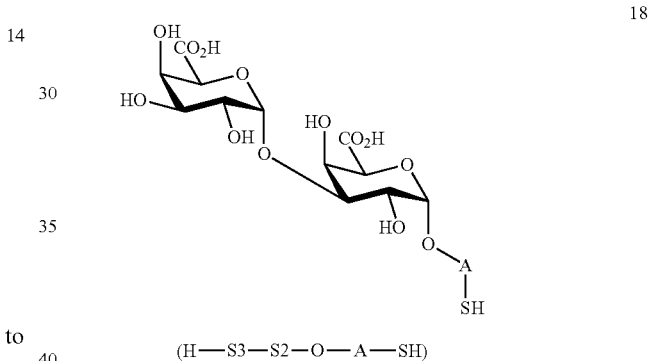
18

(H—S3—S2—O—A—SH)

wherein A is defined as above;

or performing selective removal of protecting group $P^{10}$ on compound 16 to afford compound 19 of general formula:

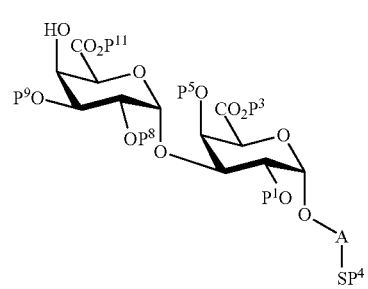
19 wherein $P^1$, $P^3$-$P^5$, $P^8$, $P^9$, $P^{11}$ and A are defined as above.

or

B2) Reacting compound 15 with compound 8 to afford compound 20 of general formula:

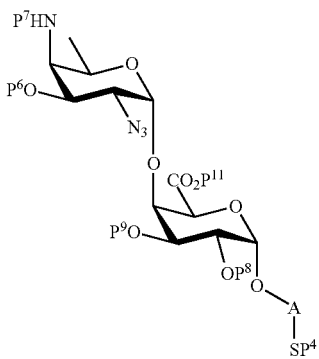

wherein $P^4$, $P^6$-$P^9$, $P^{11}$ and A are defined as above and performing conversion of the azido group to acetamido group and removal of the protecting groups $P^4$, $P^6$-$P^9$, $P^{11}$ on compound 20 to afford disaccharide disulfide 21 of general formula:

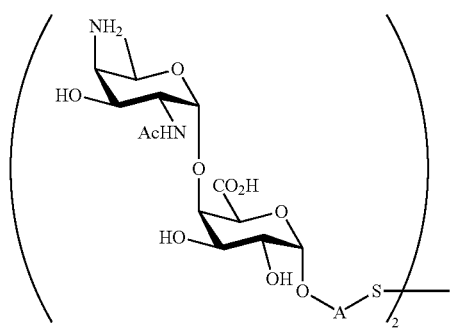

wherein A is defined as above and wherein disaccharide disulfide 21 is treated with a reducing agent to afford disaccharide 22 of general formula:

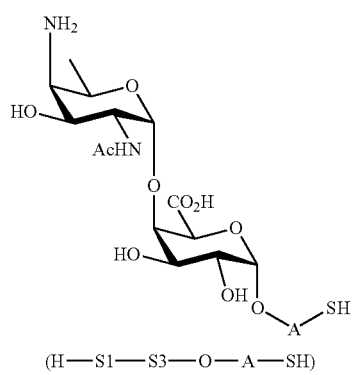

wherein A is defined as above;

or performing selective removal of protecting group $P^6$ on compound 20 to afford compound 23 of general formula:

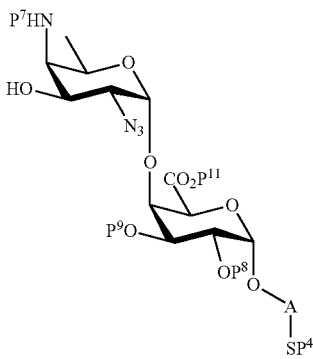

wherein $P^4$, $P^7$-$P^9$, $P^{11}$ and A are defined as above;

or

B3) Reacting compound 12 with compound 2 to afford compound 24 of general formula:

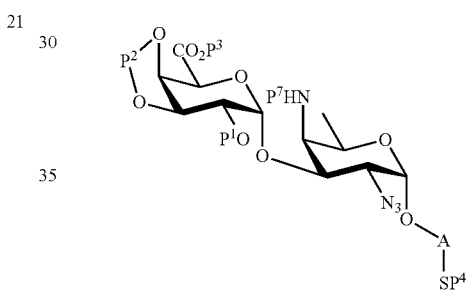

wherein $P^1$-$P^4$, $P^7$ and A are defined as above, and performing conversion of the azido group to acetamido group and removal of protecting groups $P^1$-$P^4$ and $P^7$ on compound 24 to afford disaccharide disulfide 25 of general formula:

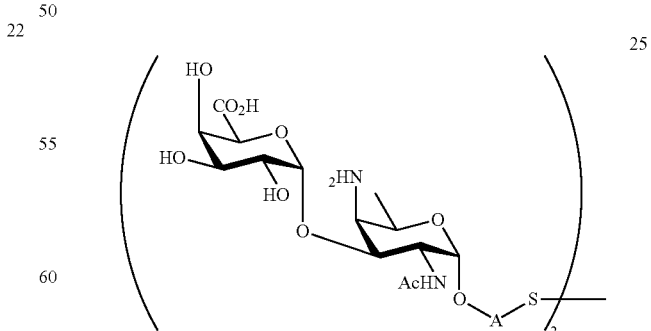

wherein A is defined as above, and wherein disaccharide disulfide 25 is further treated with a reducing agent to afford disaccharide 26 of general formula:

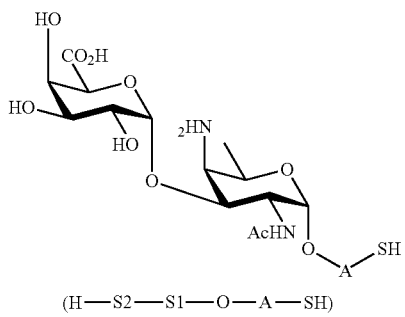

26

(H—S2—S1—O—A—SH)

wherein A is defined as above;

or performing selective deprotection on compound 24 to afford compound 27 of general formula:

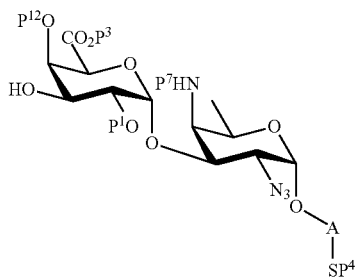

27 wherein $P^{12}$ is a protecting group and $P^1$, $P^3$, $P^4$, $P^7$ and A are defined as above.

and

C1) Reacting compound 19 with compound 8 to afford compound 28 of general formula:

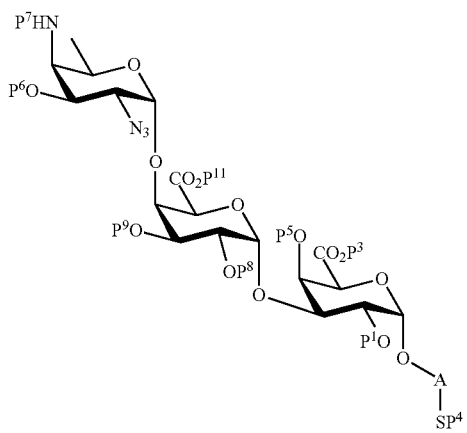

28 wherein $P^1$, $P^3$-$P^9$, $P^{11}$ and A are defined as above;
and wherein protecting group $P^6$ is replaced with protecting group $P^{13}$ in order to obtain compound 29 of the following chemical formula:

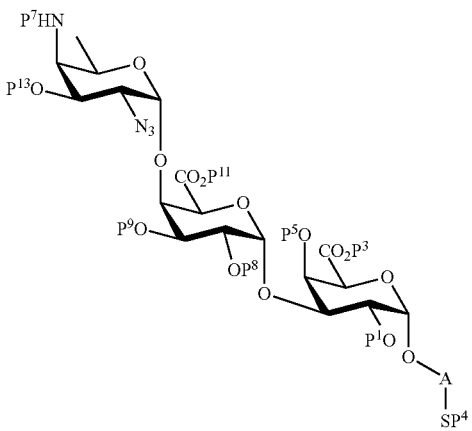

29 wherein $P^1$, $P^3$-$P^5$, $P^7$-$P^9$, $P^{11}$, $P^{13}$ and A are defined as above;

and conversion of compound 29 to trisaccharide disulfide 30 by conversion of the azido group in the acetamido group and cleavage of the protecting group $P^1$, $P^3$-$P^5$, $P^7$-$P^9$, $P^{11}$, $P^{13}$, wherein compound 30 is of general formula:

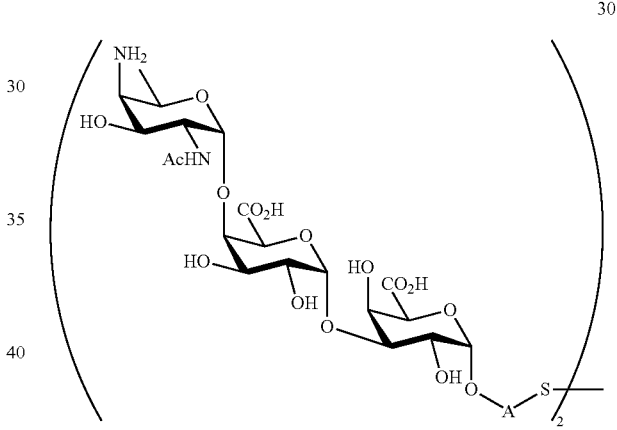

30 and wherein A is defined as above;
and conversion of trisaccharide disulfide 30 to trisaccharide 31 by treatment with a reducing agent, wherein compound 31 is of general formula:

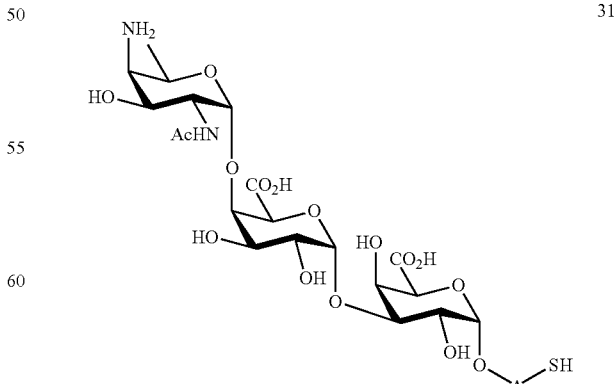

31

(H—S1—S3—S2—O—A—SH)

and wherein A is defined as above.

or

C2) Reacting compound 23 with compound 2 to afford compound 32 of general formula:

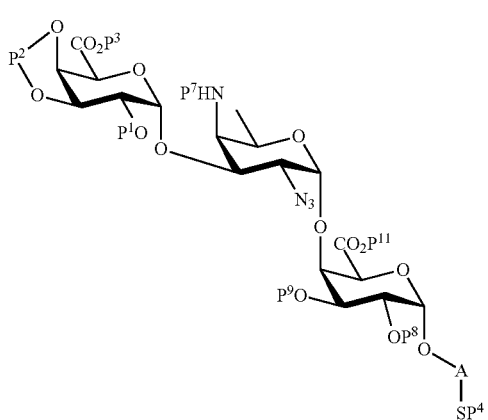

wherein $P^1$-$P^4$, $P^7$-$P^9$, $P^{11}$ and A are defined as above; and conversion of compound 32 to trisaccharide disulfide 33 by conversion of the azido group to the acetamido group and cleavage of the protecting group $P^1$-$P^4$, $P^7$-$P^9$, $P^{11}$, wherein compound 33 is of general formula:

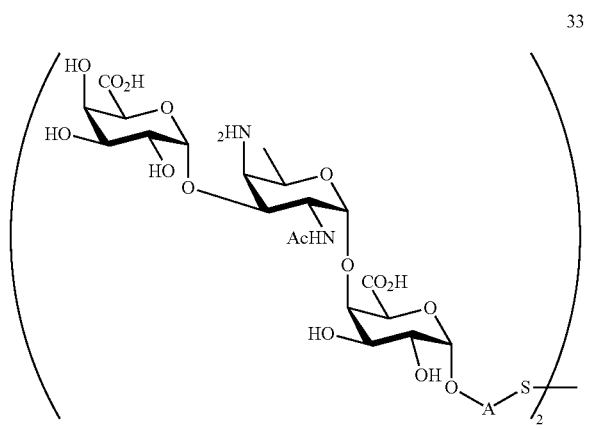

wherein A is defined as above; and conversion of trisaccharide disulfide 33 to trisaccharide 34 by treatment with a reducing agent, wherein compound 34 is of general formula:

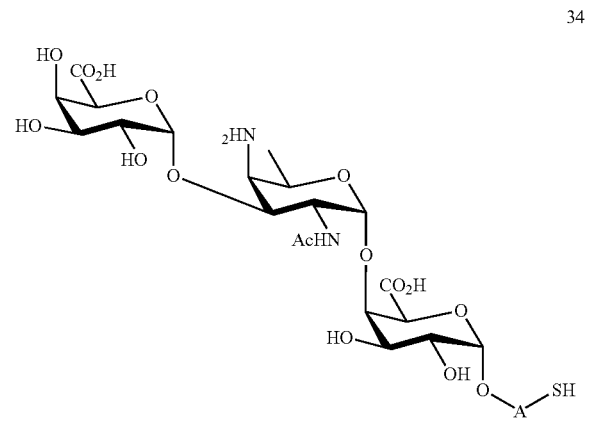

(H—S2—S1—S3—O—A—SH)

wherein A is defined as above;

or

C3) Reacting compound 27 with compound 13 to afford compound 35 of general formula:

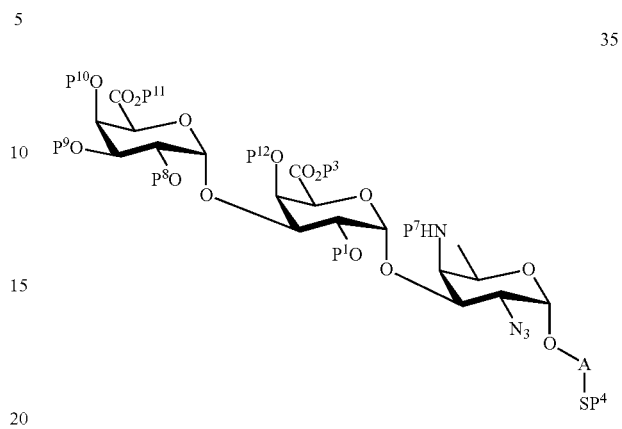

wherein $P^1$, $P^3$, $P^4$, $P^7$-$P^{11}$ and A are defined as above; and conversion of compound 35 to trisaccharide disulfide 36 by conversion of the azido group to the acetamido group and cleavage of the protecting group $P^1$, $P^3$, $P^4$, $P^7$-$P^{11}$, wherein compound 36 is of general formula:

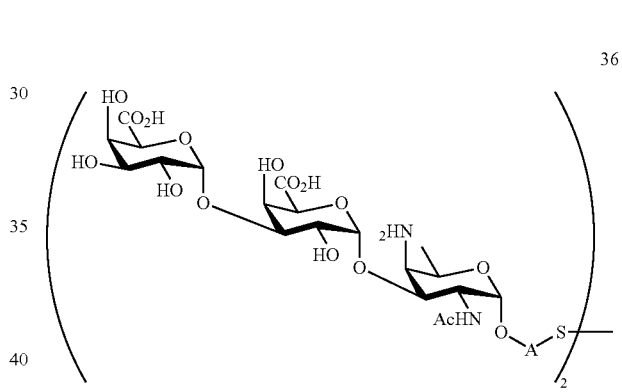

wherein A is defined as above; and conversion of trisaccharide disulfide 36 to trisaccharide 37 by treatment with a reducing agent, wherein compound 37 is of general formula:

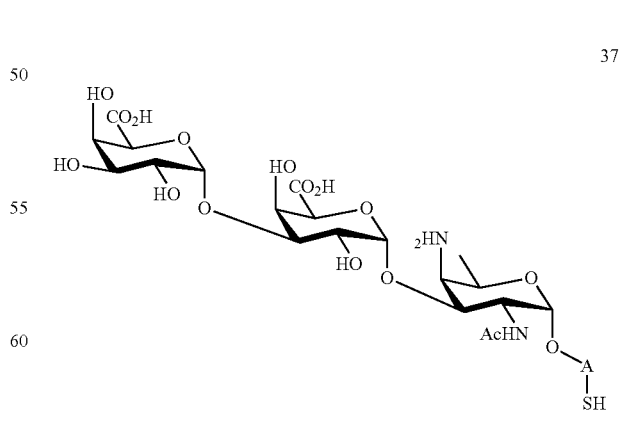

(H—S3—S2—S1—O—A—SH)

wherein A is defined as above.

The term "protecting group" as used herein refers to commonly used groups in organic synthesis, preferably used for protection of amines, hydroxyl groups, thiols, imines, carbonyls, carboxyls or other common functional groups, and particularly preferred for amines, hydroxyl groups, thiols and carboxyls.

More specifically, $P^1$, $P^2$, $P^5$, $P^6$, $P^8$-$P^{10}$, $P^{12}$ and $P^{13}$ preferably are suitable protecting groups for hydroxyl groups, more preferably different suitable protecting groups for hydroxyl groups capable of being removed subsequently one after another by a suitable sequence of deprotection reactions. Therefore, protecting groups for hydroxyl groups, namely $P^1$, $P^2$, $P^5$, $P^6$, $P^8$-$P^{10}$, $P^{12}$ and $P^{13}$ may be selected from the group consisting of or comprising: acetyl, benzyl, isopropylidene, benzylidene, benzoyl, p-methoxybenzyl, p-methoxybenzylidene, p-methoxyphenyl, p-bromobenzyl, p-bromobenzyledene, p-nitrophenyl, allyl, acetyl, isopropyl, p-bromobenzyl dimethoxytrityl, trityl, 2-naphthylmethyl, pyvaloyl, triisopropylsilyl, tert-butyldimethylsilyl, tert-butyldiphenylsilyl, tert-butylmethoxphenylsilyl, triethylsilyl, trimethylsilyl, 2-trimethylsilylethoxymethyl, 9-fluorenylmethoxycarbonyl, benzyloxymethyl, methyloxymethyl, tert-butyloxymethyl, methoxyethyloxymethyl, levulinoyl.

More specifically, in a preferred embodiment of the present invention protecting groups $P^1$, $P^5$, $P^8$, $P^9$ and $P^{12}$ are benzyl, $P^2$ is benzylidene, $P^6$ is levulinoyl, $P^{10}$ is 9-fluorenylmethoxycarbonyl and $P^{13}$ is benzyloxymethyl.

Amines are generally protected as carbamates. Therefore, protecting group $P^7$ may be selected from the group consisting of or comprising tert-butyloxy carbonyl, 9-fluorenylmethoxy carbonyl, allyloxy carbonyl, 2,2,2-trichloroethyloxy carbonyl, benzyloxy carbonyl. In a preferred embodiment of the present invention $P^7$ is benzyloxy carbonyl.

Carboxylic acids are generally protected as esters. Therefore protecting groups $P^3$ and $P^{11}$ may be selected from the group consisting of or comprising methyl, ethyl, allyl, isopropyl, tert-butyl, phenyl, benzyl, p-methoxybenzyl. In a preferred embodiment of the present invention protecting groups $P^3$ and $P^{11}$ are methyl.

Protecting groups for hydroxyl groups may serve as well as protecting groups for thiols. Therefore, preferred protecting groups for thiols groups are benzyl, benzoyl, 4-O-p-methoxybenzyl, allyl, acetyl, methylsulfonylethoxycarbonyl, levulinyl, dimethoxytrityl, 2-naphthylmethyl, triisopropylsilyl, tert-butyldimethylsilyl, tert-butyldiphenylsilyl, 2-trimethylsilylethoxymethyl. Specifically, in a preferred embodiment of the present invention protecting group $P^4$ is a benzyl group.

The protecting groups employed in the synthesis of saccharides of general formula (I) can be differentiated in permanent protecting groups and temporary protecting groups. Permanent protecting groups are protecting groups that are stable during the entire synthesis and that can be efficiently removed at the late stage of the synthesis. Such permanent groups include, but they are not restricted to benzyl, benzylidene, benzoate, acetate, alkyl esters. The temporary protecting groups are generally orthogonal protecting groups that can be selectively removed at different levels of the synthesis to free hydroxyl groups for subsequent introduction of different substituents, including mono-saccharides or other protecting groups. The ingenious choice of protecting groups allows expedient access to a library of saccharides of general formula (I) functionalized with a thiol group for subsequent conjugation to a carrier immunogen or a solid support.

A preferred embodiment of the present invention is directed to the synthesis of saccharides of general formula (I)

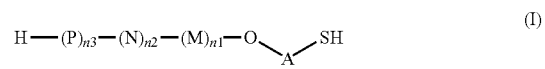

wherein A is a linker defined as above,

P represents S1,

N represents S3,

M represents S2, sugar fragments S1, S2, S3 are connected to the each other and to —O-A-SH fragment via O-glycosidic bonds, sugar fragment S2 cannot be connected to sugar fragment S1, and n1, n2 and n3 are integers selected from 0 and 1, wherein at least one of the integers n1, n2 and n3 is 1 and comprising the steps:

A1) Reacting the compound 2 of the formula:

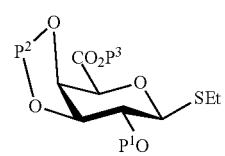

wherein $P^1$-$P^3$ represent protecting groups, with the compound 3 of the formula

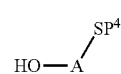

wherein $P^4$ represents a protecting group, in order to obtain compound 4 of general formula:

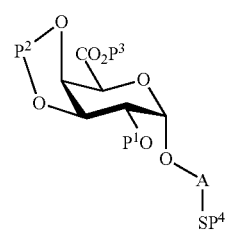

wherein $P^1$-$P^4$ and A are defined as above;

and performing removal of protecting groups $P^1$-$P^4$ on compound 4 to afford monosaccharide disulfide 5 of general formula:

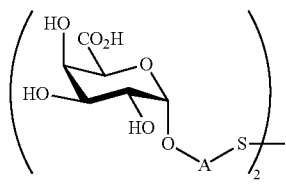

5 wherein A is defined as above, and wherein monosaccharide disulfide 5 is further treated with a reducing agent to afford monosaccharide 6 of general formula:

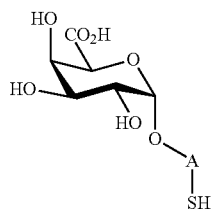

6

(H—S2—O—A—SH)

wherein A is defined as above;

or performing selective deprotection on compound 4 to afford compound 7 of general formula

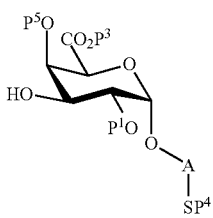

7 wherein $P^5$ is a protecting group and $P^1$, $P^3$, $P^4$ and A are defined as above.

or

A2) Reacting compound 8 of general formula

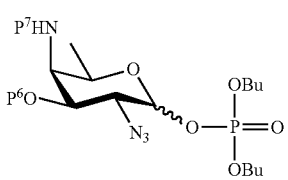

8 wherein $P^6$ and $P^7$ represent protecting groups, with compound 3 to afford compound 9 of general formula

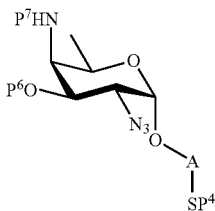

9 wherein $P^6$, $P^7$ and A are defined as above;

and performing conversion of the azido group to acetamido group and removal of the protecting groups $P^4$, $P^6$ and $P^7$ on compound 9 to afford monosaccharide disulfide 10 of general formula:

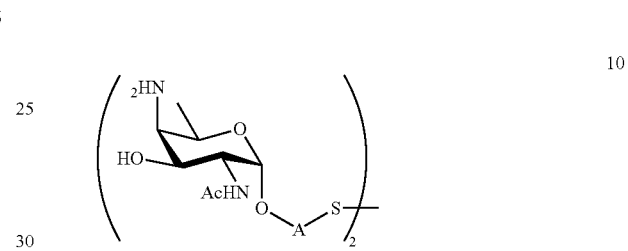

10 wherein A is defined as above and, wherein monosaccharide disulfide 10 is further treated with a reducing agent to afford monosaccharide 11 of general formula:

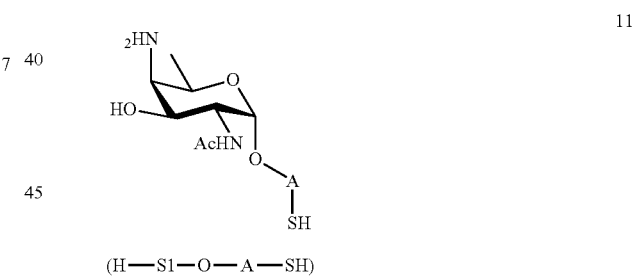

11

(H—S1—O—A—SH)

wherein A is defined as above.

or

A3) Reacting compound 13 of general formula

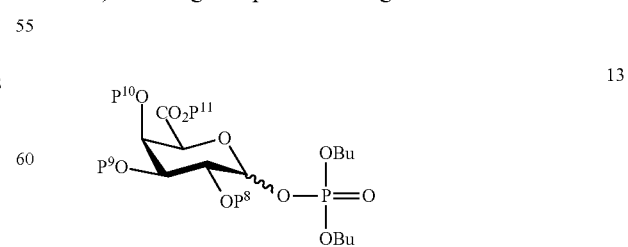

13 wherein $P^8$-$P^{11}$ represent protecting groups, with compound 3 to afford compound 14 of general formula:

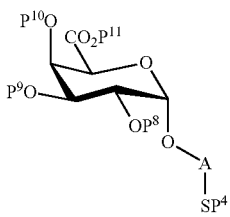

14 wherein $P^4$, $P^8$-$P^{11}$ are defined as above
and
performing selective deprotection of compound 14 to afford compound 15 of general formula:

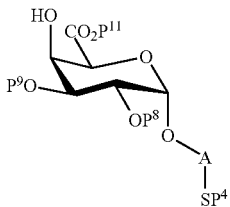

15 wherein $P^4$, $P^8$, $P^9$, $P^{11}$ and A are defined as above.
and
B1) Reacting compound 7 with compound 13 to afford compound 16 of general formula:

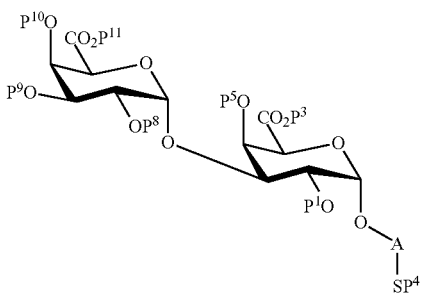

16 wherein $P^1$, $P^3$-$P^5$, $P^8$-$P^{11}$ and A are defined as above;
and
performing removal of protecting groups $P^1$, $P^3$-$P^5$, $P^8$-$P^{11}$ on compound 16 to afford disaccharide disulfide 17 of general formula:

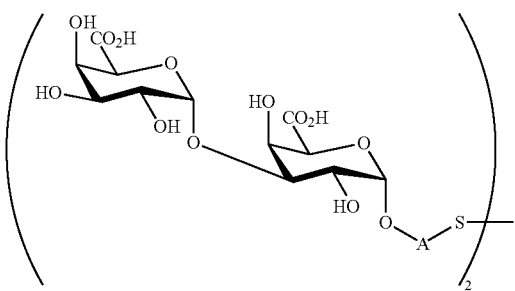

17 wherein A is defined as above and wherein disaccharide disulfide 17 is further treated with a reducing agent to afford disaccharide 18 of general formula:

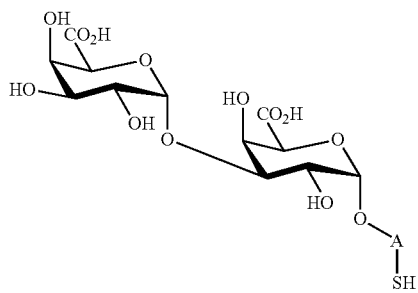

18

(H—S3—S2—O—A—SH)

wherein A is defined as above;
or
performing selective removal of protecting group $P^{10}$ on compound 16 to afford compound 19 of general formula:

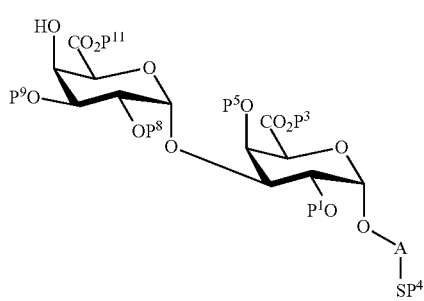

19 wherein $P^1$, $P^3$-$P^5$, $P^8$, $P^9$, $P^{11}$ and A are defined as above.
or
B2) Reacting compound 15 with compound 8 to afford compound 20 of general formula:

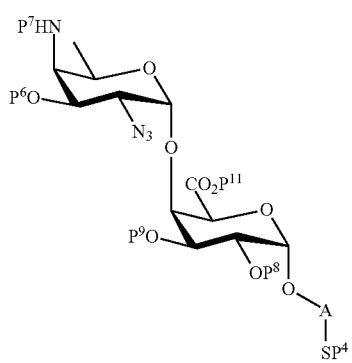

20 wherein $P^4$, $P^6$-$P^9$, $P^{11}$ and A are defined as above;
and
performing conversion of the azido group to acetamido group and removal of the protecting groups $P^4$, $P^6$-$P^9$, $P^{11}$ on compound 20 to afford disaccharide disulfide 21 of general formula:

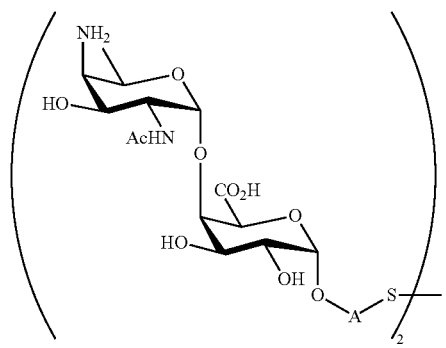

wherein A is defined as above and wherein disaccharide disulfide 21 is treated with a reducing agent to afford disaccharide 22 of general formula:

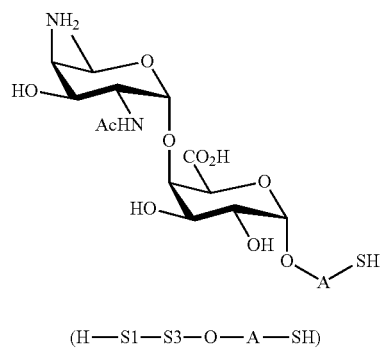

(H—S1—S3—O—A—SH)

wherein A is defined as above.

and

C1) Reacting compound 19 with compound 8 to afford compound 28 of general formula:

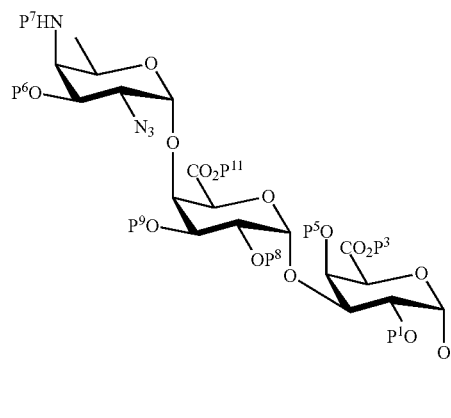

wherein $P^1$, $P^3$-$P^9$, $P^{11}$ and A are defined as above;

and wherein protecting group $P^6$ is replaced with protecting group $P^{13}$ in order to obtain compound 29 of the following chemical formula:

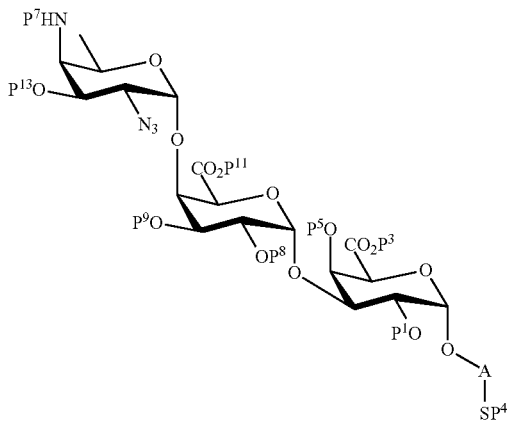

wherein $P^1$, $P^3$-$P^5$, $P^7$-$P^9$, $P^{11}$, $P^{13}$ and A are defined as above;

and conversion of compound 29 to trisaccharide disulfide 30 by conversion of the azido group to the acetamido group and cleavage of the protecting group $P^1$, $P^3$-$P^5$, $P^7$-$P^9$, $P^{11}$, $P^{13}$, wherein compound 30 is of general formula:

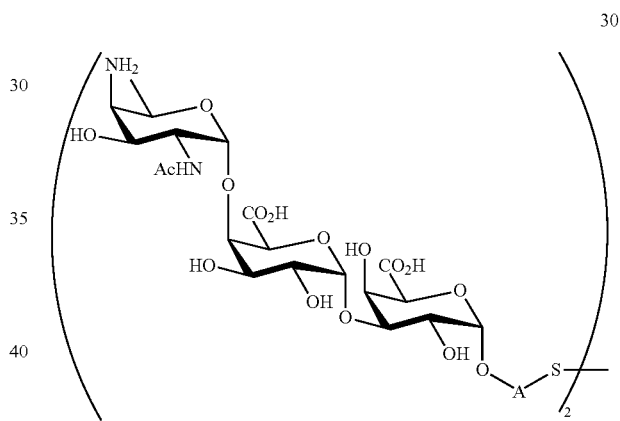

and wherein A is defined as above;

and conversion of trisaccharide disulfide 30 to trisaccharide 31 by treatment with a reducing agent, wherein compound 31 is of general formula:

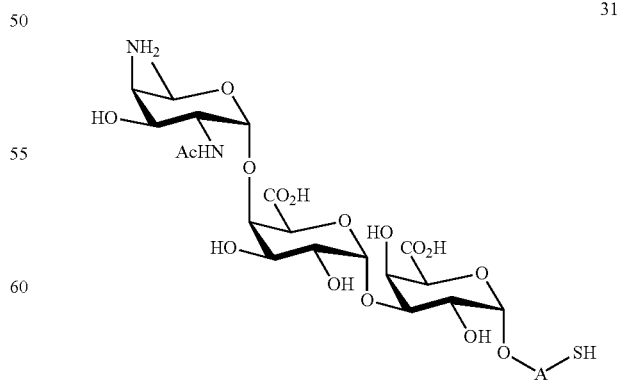

(H—S1—S3—S2—O—A—SH)

and wherein A is defined as above.

The conversion of the saccharide disulfides 36, 33, 30, 25, 21, 17, 10 and 5 to the saccharides 37, 34, 31, 26, 22, 18, 11, and 6 respectively is performed in presence of a reducing agent. Known reducing agent for the person skilled in the art include, but they are not restricted to: mercaptoethanol, ditriotheritol, tris(2-carboxyethyl)phosphine, magnesium/methanol, sodium/ammonia followed by ammonium chloride/chlorhydric acid. Preferably the conversion of the saccharide disulfides to the corresponding saccharides is carried out with tris(2-carboxyethyl)phosphine.

It is preferred that the reaction between compounds 2 and 3, compounds 2 and 12, compounds 5* and 11*, compounds 19* and 21*, compounds 2 and 23 is performed in presence of (dimethylthio)methylsulfonium trifluoromethanesulfonate (DMTST) and 2,4,6-tri-tert-butylpyridine (TTBPy) in a mixture of non-polar solvent and polar aprotic solvent. In addition activated molecular sieve (MS) such as 3 Å molecular sieve, 4 Å molecular sieves or 3 Å acid washed molecular sieves can be used. The reaction temperature is between −20° C. and room temperature, preferably the temperature is between −10° C. and room temperature, more preferably the temperature is between −5° C. and room temperature and most preferably the temperature is between 0° C. and room temperature. Preferred polar aprotic solvents are tetrahydrofuran, diethyl ether and dioxane. Preferred non-polar solvents are toluene, halogenated solvents such as chloroform and methylene chloride. Preferred mixtures of non-polar and polar aprotic solvent are: methylene chloride/tetrahydrofuran, methylene chloride/diethyl ether, toluene/diethyl ether, toluene/tetrahydrofuran.

It is also preferred that the reaction of compounds 13 and 7, compounds 8 and 3, compounds 12* and 9*, compounds 13* and 2*, compounds 2* and 21*, compounds 2* and 11*, compounds 19 and 8, compounds 27 and 13 and compounds 8 and 15, is performed in a non polar solvent or a mixture of non polar and polar aprotic solvents in presence of silyl triflate. Examples of silyl triflate include, but are not restricted to trimethylsilyl trifluoromethanesulfonate, tert-butyl dimethyl trifluoromethanesulfonate, triiospropyl trifluoromethanesulfonate. Suitable non-polar solvents are toluene, chloroform and methylene chloride. Preferred polar aprotic solvents are tetrahydrofuran, diethyl ether and dioxane. The reaction temperature is between −20° C. and +20° C., preferably the temperature is between −10° C. and +10° C. and more preferably the temperature is between −5° C. and +5° C. and most preferably about 0° C. Preferably, activated molecular sieve (MS) such as 3 Å molecular sieve, 4 Å molecular sieves or 3 Å acid washed molecular sieves can be used.

Preferably the replacement of protecting group $P^6$ on compound 28 with protecting group $P^{13}$ to obtain compound 29 is performed in two steps, first involving the reaction of compound 28 with hydrazine or a hydrazinium salt in a solvent or mixture of solvents and second by treatment of the product obtained after the first step with $BnOCH_2SCy$, DMTST and TTBPy in a non-polar solvent. For the first step, hydrazinium salts of weak acids are preferred such as hydrazinium acetate or hydrazinium propionate. Suitable solvents for this reaction are non-polar solvents, such as methylene chloride, polar solvents such as pyridine and acetic acid, and mixtures thereof. The second step is preferably conducted in presence of activated molecular sieves as the one mentioned above at a temperature preferably between −10° C. and 20° C. and most preferably between 0° C. and 10° C. Suitable non-polar solvents are mentioned above. It was found that the replacement of protecting group $P^6$ with protecting group $P^{13}$ is essential for avoiding side-reactions during the cleavage of the permanent protecting group.

The conversion of compound 4 to 5, 16 to 17, 13* to 27* and 20* to 22* requires cleavage of the protecting group, and more specifically of the permanent protecting groups. The cleavage of said protecting groups involves first cleavage of the base-labile protecting groups by treatment with a base in a mixture of polar aprotic and polar protic solvent; and second cleavage of the protecting groups sensitive to hydrogenation by exposure to sodium and ammonia in a mixture of polar protic and polar aprotic solvents. For the first step suitable aprotic solvents include tetrahydrofuran, ethyl acetate, acetone, N,N-dimethylformamide, acetonitrile and N,N-dimethylsulfoxide, which are mixed with a suitable protic solvent such as water and alcohols including methanol, ethanol, propanol, isopropanol or tert-buthanol. The basic cleavage of the protecting groups is preferably performed at room temperature comprised between 0° C. and room temperature. Appropriate base for performing first step include lithium hydroxide, sodium hydroxide and potassium hydroxide. The cleavage of the protecting groups sensitive to hydrogenation is conducted by exposure to sodium and ammonia in a mixture of polar protic and polar aprotic solvents at a temperature comprised between −78° C. and room temperature. Optionally, lithium can be used as equivalent of sodium during the cleavage of the protecting groups sensitive to hydrogenation.

Previous to the above mentioned cleavage of permanent protecting groups, the conversion of compounds 9 to 10, 20 to 21, 24 to 25, 29 to 30, 32 to 33, 36 to 37, and 16* to 18* involves conversion of the azido group in the acetamido group, which is preferably performed in presence of thioacetic acid and pyridine. An alternative method is to conduct conversion of the azido group in the acetamido group in two steps: first chemoselective reduction of the azido group, and then acetylation. The chemoselective reduction can be carried out using by hydrogenolysis on Pd/C in presence of ammonia, ammonium acetate, triphenylphosphine or pyridine. The acetylation can be accomplished using acetyl chloride or acetic anhydride in presence of a base.

The saccharides I, 5, 6, 10, 11, 17, 18, 21, 22, 25, 26, 30, 31, 33, 34, 36, 37, 27*, 26*, 24*, 22* and 18* bear basic and/or acidic substituents and they may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

Examples for suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of an acid, selected out of the group mentioned above.

Further, it is also possible that the compounds of the present invention bear simultaneously basic and acid groups. Further, it may also occur that these basic and acid groups appear to be in close vicinity to one another enabling an intramolecular proton transfer from the acidic group the basic group. Therefore, in a preferred embodiment of the present invention the compound of the formula (I) may be zwitter-ionic, bearing at least e.g. one —O⁻ and one —NH$_3^+$ group.

This invention includes within its scope stoechiometric solvates including hydrates as well as compounds containing variable amounts of water that may be produced by processes such as lyophilisation.

Thus, the synthesis of the saccharides of the general formula (I) may further comprise step D:

D) preparing a salt of the compound of general formula (I) or preparing a lyophilisate of the compound of general formula (I) or of the salt of the compound of general formula (I).

In another preferred embodiment, the synthesis of intermediates of general formula (II) may further comprise step D:

D) preparing a salt of the compound of general formula (II) or preparing a lyophilisate of the compound of general formula (II) or of the salt of the compound of general formula (II).

In a preferred embodiment, the synthesis of saccharides of the general formula (I)

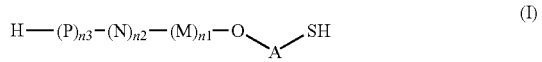

(I)

wherein A is a linker defined as above,
P represents S1,
N represents S3,
M represents S2,
sugar fragments S1, S2, S3 are connected to the each other and to —O-A-SH fragment via O-glycosidic bonds, sugar fragment S2 cannot be connected to sugar fragment S1, and
n1, n2 and n3 are integers selected from 0 and 1, wherein at least one of the integers n1, n2 and n3 is 1
and
may further comprise step D)

D) preparing a salt of the compound of general formula (I) or preparing a lyophilisate of the compound of general formula (I) or of the salt of the compound of general formula (I).

Intermediates

Another aspect of the present invention is directed to intermediates of general formula (II):

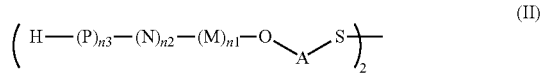

(II)

wherein A is a linker;

M, N and P represent independently of each other one of the following fragments:

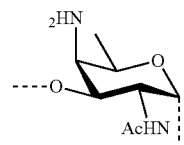

S1

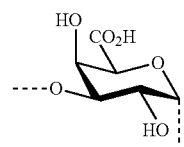

S2

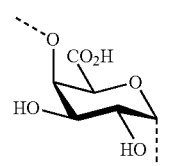

S3 wherein sugar fragments S1, S2, S3 are connected to each other and to —O-A-S— fragment via O-glycosidic bonds, each sugar fragment S1, S2, and S3 is not more than once present in the fragment H—(P)$_{n3}$—(N)$_{n2}$—(M)$_{n1}$—O-A-S—, sugar fragment S1 cannot be simultaneously connected to —O-A-S— and sugar fragment S3, sugar fragment S3 cannot be simultaneously connected to —O-A-S— and sugar fragment S2, sugar fragment S2 cannot be simultaneously connected to —O-A-S— and sugar fragment S1, and
n1, n2 and n3 are integers selected from 0 and 1, wherein at least one of the integers n1, n2 and n3 is 1, and pharmaceutically acceptable salts of these saccharides.

Thus, under the scope of the present invention are falling intermediates of general formula (IIa)

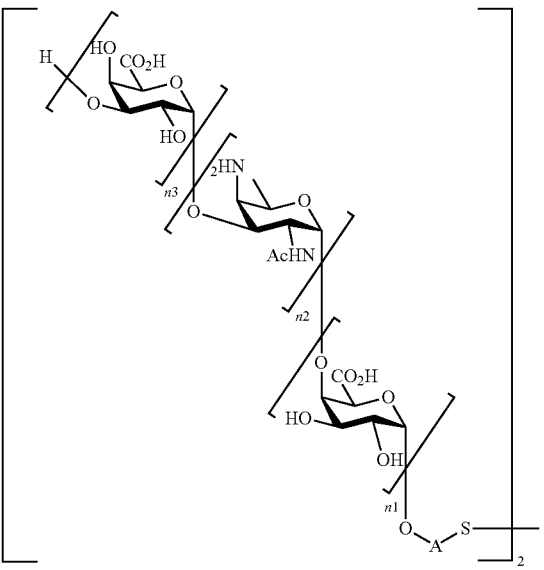

IIa wherein
n1=n2=n3=1, or n1=n2=1 and n3=0, or n2=n3=1 and n1=0, or n1=1 and n2=n3=0, or n2=1 and n1=n3=0;

and intermediates of general formula (IIb)

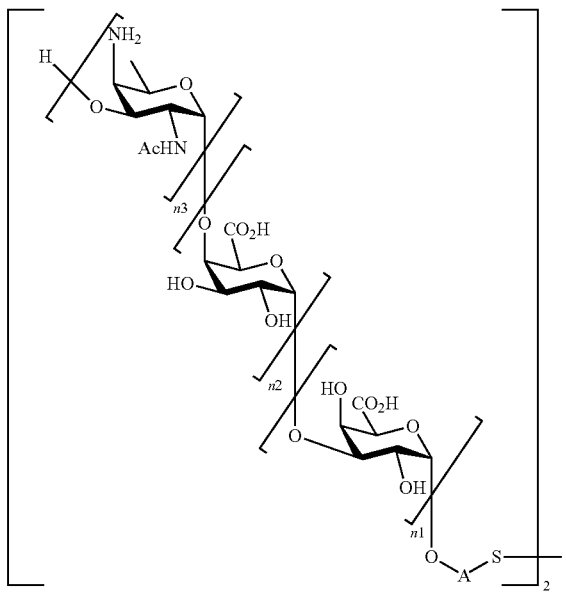

Wherein
n1=n2=n3=1, or n1=n2=1 and n3=, or n2=n3=1 and n1=, or n1=1 and n2=n3=0, or n3=1 and n1=n2=0;
and intermediates of general formula (IIc)

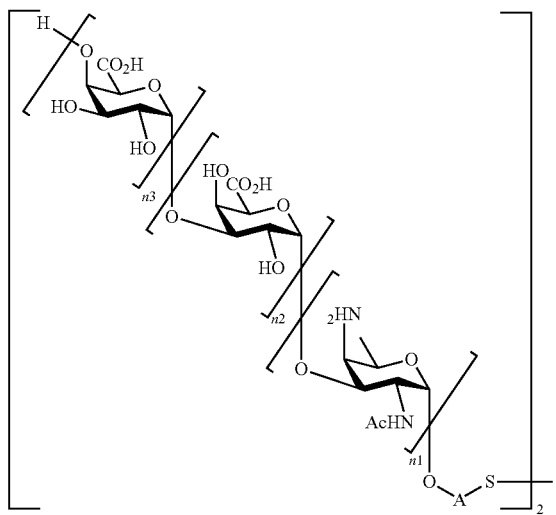

Wherein
n1=n2=n3=1, or n1=n2=1 and n3=0, or n2=n3=1 and n1=0, or n1=1 and n2=n3=0, or n3=1 and n1=n2=0
and pharmaceutically acceptable salts of these saccharides.

In other words, the present invention relates to intermediates of general formula (II):

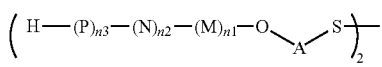

wherein A is a linker;
P represents S1, N represents S3, M represents S2;
or
P represents S3, N represents S2, M represents S1;
or
P represents S2, N represents S1, M represents S3, and wherein
n1=n2=n3=1, or n1=n2=1 and n3=0, or n2=n3=1 and n1=0, or n1=1 and n2=n3=0, or n2=1 and n1=n3=0, or n3=1 and n1=n2=0;
wherein

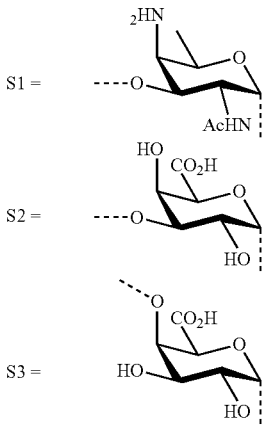

and the sugar fragments S1, S2, S3 are connected to the each other and to —O-A-S— fragment via O-glycosidic bonds,
and pharmaceutically acceptable salts of these saccharides.

Preferred are intermediates of general formula (II)

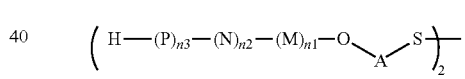

wherein
A is a linker defined as above,
P represents S1,
N represents S3,
M represents S2,
sugar fragments S1, S2, S3 are connected to the each other and to —O-A-S-fragment via O-glycosidic bonds and sugar fragment S2 cannot be connected to sugar fragment S1, and
n1, n2 and n3 are integers selected from 0 and 1, wherein at least one of the integers n1, n2 and n3 is 1 and
pharmaceutically acceptable salts of these saccharides.

More preferred are intermediates of general formula (II)

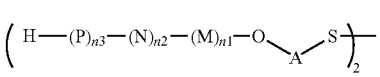

wherein A is a linker defined as above,
P represents S1,
N represents S3,
M represents S2,
sugar fragments S1, S2, S3 are connected to the each other and to —O-A-S-fragment via O-glycosidic bonds and wherein n1=n2=n3=1 or wherein n1=n2=1 and n3=0 or wherein n1=1 and n2=n3=0 or wherein n1=0 and n2=n3=1 or wherein n1=n2=0 and n3=1.

Even more preferred are the intermediates:

H—(S1)-(S3)-(S2)-O-A-S—S-A-O—(S2)-(S3)-(S1)-H,
H—(S2)-(S1)-(S3)-O-A-S—S-A-O—(S3)-(S1)-(S2)-H,
H—(S3)-(S2)-(S1)-O-A-S—S-A-O—(S1)-(S2)-(S3)-H,
H—(S1)-(S3)-O-A-S—S-A-O—(S3)-(S1)-H,
H—(S3)-(S2)-O-A-S—S-A-O—(S2)-(S3)-H,
H—(S2)-(S1)-O-A-S—S-A-O—(S1)-(S2)-H, H—(S1)-O-A-S—S-A-O—(S1)-H, and
H—(S3)-O-A-S—S-A-O—(S3)-H. Particularly preferred are intermediates of general formula (II) comprising the sugar fragment S1, such as:

H—(S1)-(S3)-(S2)-O-A-S—S-A-O—(S2)-(S3)-(S1)-H,
H—(S2)-(S1)-(S3)-O-A-S—S-A-O—(S3)-(S1)-(S2)-H,
H—(S3)-(S2)-(S1)-O-A-S—S-A-O—(S1)-(S2)-(S3)-H,
H—(S1)-(S3)-O-A-S—S-A-O—(S3)-(S1)-H,
H—(S2)-(S1)-O-A-S—S-A-O—(S1)-(S2)-H, and
H—(S1)-O-A-S—S-A-O—(S1)-H.

Glycoconjugates

Another aspect of the present invention refers to a glycoconjugate obtained by reacting a saccharide of general formula (I), (Ia), (Ib) and (Ic) with an immunogenic carrier. Said glycoconjugate proved to be efficient as a vaccine for immunization against diseases associated with bacteria. Hence, glycoconjugates comprising a saccharide of general formula (I), (Ia), (Ib) and (Ic) covalently linked to an immunogenic carrier are useful for raising a protective immune response in a human and/or animal host and therefore are useful for the prevention and/or treatment of diseases associated with bacteria.

Saccharides are known by the person skilled in the art as generally TI-2 (T cell independent-2) antigens and poor immunogens. TI-2 antigens are antigens, which are recognized only by mature B cells through the cross linking of surface exposed immunoglobulin receptors. Without T cell help, no immunological memory is generated and neither isotype switching from IgM to other IgG subclasses, nor B cells affinity maturation occurs. Moreover, saccharides are known poor immunogens in humans due to the structural homology to human glycolipids and glycoproteins. Due to their poor immunogenic properties, saccharides manifest poor ability to produce both antibody production by B cells, as well as the formation of memory cells, features which are essential for the production of potent vaccines.

Therefore, to produce a potent saccharide-based vaccine, the saccharides of general formula (I), (Ia), (Ib) and (Ic) are conjugated to an immunogenic carrier to provide glycoconjugates, which present increased immunogenicity in comparison with the saccharide.

In this context the term "immunogenic carrier" is defined as a structure, which is conjugated to the saccharide to form a glycoconjugate that presents an increased immunity in comparison with the saccharide per se. Thus, the conjugation of the saccharides of general formula (I), (Ia), (Ib) and (Ic) to the immunogenic carrier has as effect the stimulation of the immune response against the saccharide of general formula (I), (Ia), (Ib) or (Ic) without inducing an immune response against the said immunogenic carrier.

Preferred immunogenic carriers are carrier proteins or glycosphingolipid with immunomodulatory properties. For the person skilled in the art, a carrier protein is a protein selected from the group comprising or consisting of: a diphtheria toxoid, a mutated diphtheria toxoid, a modified diphtheria toxoid, a mutated and modified diphtheria toxoid, a tetanus toxoid, a modified tetanus toxoid, a mutated tetanus toxoid, outer membrane protein (OMP), bovine serum albumin (BSA), keyhole limpet hemocyanine (KLH) or cholera toxoid (CT). The term "toxoid" as used herein refers to a bacterial toxin (usually an exotoxin), whose toxicity has been inactivated or suppressed either by chemical (formalin) or heat treatment, while other properties, typically immunogenicity, are maintained. A mutated toxoid as used herein is a recombinant bacterial toxin, which has been amended to be less toxic or even non-toxic by amending the wild-type amino acid sequence. Such a mutation could be a substitution of one or more amino acids. Such a mutated toxoid presents on its surface a functionality that can react with the functional group Y of the interconnecting molecule to provide a modified toxoid. Said functionality is known to the person skilled in the art and includes, but is not restricted to the primary amino functionality of a lysine residue that can react with activated esters, an isocyanate group or an aldehyde in presence of a reducing agent, to the carboxylate functionality of a glutamate or aspartate residue that can be activated by carbodiimides or to the thiol functionality of a cysteine residue. Activated esters include N-(γ-maleimidobutyryloxy) sulfosuccinimide ester (sulfo-GMBS), succinimidyl (4-iodoacetyl) aminobenzoate (sulfo-SIAB), succinimidyl-3-(bromoacetamido)propionate (SBAP), disuccinimidyl glutarat (DSG), 2-pyridyldithiol-tetraoxatetradecane-N-hydroxysuccinimide (PEG-4-SPDP) (see FIG. 2). The cysteine residue on the carrier protein can be converted to the corresponding dehydroalanine that can be further reacted with a suitable interconnecting molecule to provide modified carrier protein having on their surface the functional group X of the interconnecting molecule. In this case the functional group Y on the interconnecting molecule might be a thiol group and the group X might be an alkene. Such interconnecting molecules include allylmercaptan. After reaction with such interconnecting molecule, the carrier protein is converted to a modified carrier protein presenting the vinyl group X of the interconnecting molecule, which is suitable to react with the saccharides of general formula (I), (Ia), (Ib) and (Ic).

It is especially preferred that the saccharides of general formula (I), (Ia), (Ib) and (Ic) and preferably saccharides 37, 34, 31, 26, 22, 18, 11 and 6 are conjugated to the non-toxic mutated diphtheria toxin $CRM_{197}$ presenting as a functionality a primary amine functionality of a lysine residue.

$CRM_{197}$ like wild-type diphtheria toxin is a single polypeptide chain of 535 amino acids (58 kD) consisting of two subunits linked by disulfide bridges having a single amino acid substitution of glutamic acid for glycine. It is utilized as a carrier protein in a number of approved conjugate vaccines for diseases such as Prevnar.

Thus, in a preferred embodiment of the present invention the carrier protein presents on its surface primary amino functionalities of lysine residues that are able to react with the functional group Y of the interconnecting molecule to provide modified carrier protein having on their surface said functional group X of the interconnecting molecule, which is able to react with the terminal thiol group of the linker of the compounds of general formula (I). Said functional group X of the interconnecting molecules is selected of the group comprising or consisting of maleimide; α-iodoacetyl; α-bromoacetyl; N-hydroxysuccinimide ester (NHS), 2-pyridyldithiols, thiol and vinyl (see FIG. 3).

Preferably, the saccharide of general formula (I), (Ia), (Ib) or (Ic) is conjugated to the non-toxic mutated diphtheria toxin $CRM_{197}$, which is modified by maleimide. In yet another preferred embodiment, the saccharide of general formula (I), (Ia), (Ib) or (Ic) is conjugated to the non-toxic mutated diphtheria toxin $CRM_{197}$, which is modified by vinyl. In the most preferred embodiment, the saccharide of general formula (I), (Ia), (Ib) or (Ic) is conjugated to the non-toxic mutated diphtheria toxin $CRM_{197}$, which is modified by α-bromoacetamide.

In another embodiment, said immunogenic carrier is preferably a glycosphingolipid with immunomodulatory properties, and more preferably (2S,3S,4R)-1-(α-D-galactopyranosyl)-2-hexacosanoylaminooctadecane-3,4-diol. The term glycosphingolipid with immunomodulatory properties, as used herein, refers to a suitable glycosphingolipid capable of stimulating the immune system's response to a target antigen, but which does not in itself confer immunity as defined above.

Glycoshingolipids as used herein are compounds containing a carbohydrate moiety α-linked to a sphingolipid. Preferably, the carbohydrate moiety is a hexopyranose and most preferably is α-D-galactopyranose. For the person skilled in the art, sphingolipids are a class of lipids containing a C18 amino alcohol connected via an amide bond to a fatty acid. The C18 amino alcohol is preferably mono-, di- or poly-substituted with hydroxyl groups. Especially preferred, the C18 amino alcohol is phytosphingosine. The fatty acid is preferably a monocarboxylic acid having a saturated alkyl chain of a number of carbons ranging from 16 to 28 and more preferably from 18 to 26. Glycosphingolipids with immunomodulatory properties include, but they are not restricted to (2S,3S,4R)-1-(α-D-galactopyranosyl)-2-hexacosanoylaminooctadecane-3,4-diol, which can stimulate natural killer (NK) activity and cytokine production by natural killer T (NKT) cells and exhibits potent antitumor activity in vivo (*Proc. Natl Acad. Sci. USA*, 1998, 95, 5690).

The conjugates of the saccharides of general formula (I), (Ia), (Ib) or (Ic) with a glycosphingolipid with immuno-modulatory properties have the advantage of being heat stable. To be suitable for conjugation, on the glycosphingolipid with immunomodulatory properties a functionality is introduced. Said functionality is prone to react directly with the terminal thiol group of the linker of the saccharides of general formula (I), (Ia), (Ib) or (Ic) to provide glycoconjugates of the saccharides of general formula (I), (Ia), (Ib) or (Ic), or with the functional group Y of the interconnecting molecule to provide the modified glycosphingolipid with immunomodulatory properties.

Preferably, said functionality is introduced at the C6 of the carbohydrate moiety of the glycosphingolipid with immunomodulatory properties. Thus, the glycosphingolipid with immunomodulatory properties is functionalized with a functionality, which is prone of reacting with thiol group, activated ester, isocyanate group, aldehyde, vinyl, amino group and azido group to provide directly the glycoconjugate of the saccharides of general formula (I) or the modified glycosphingolipid with immunomodulatory properties presenting the functional group X of the interconnecting molecule.

Preferably, the functionality introduced at the C6 of the carbohydrate moiety of the glycosphingolipid with immunomodulatory properties is selected from the group comprising or containing an amine, a thiol, an alcohol, a carboxylic acid, a vinyl, maleimide, α-iodoacetyl, α-bromoacetyl, N-hydroxysuccinimide ester (NHS), 2-pyridyldithiols.

Said functional group X of the interconnecting molecules is selected of the group comprising or consisting of maleimide, α-iodoacetyl, α-bromoacetyl, N-hydroxysuccinimide ester (NHS), 2-pyridyldithiols, thiol and vinyl.

As used herein, the term "interconnecting molecule" refers to a bifunctional molecule containing functional group X and functional group Y, wherein functional group X is capable of reacting with the terminal thiol group on the linker A and the functional group Y is capable of binding to an immunogenic carrier or to a solid support.

It was found that the glycoconjugates obtained by reacting the saccharides of general formula (I), (Ia), (Ib) and (Ic) with an immunogenic carrier are suitable to elicit an immune response in an animal, and therefore are useful as a vaccine in immunization against diseases associated with bacteria containing in their capsular polysaccharide a saccharide structure selected from:

α-2,4,6-trideoxy-4-amino-D-GalNAc-(1→4)-α-D-GalAp-(1→3)-α-D-GalAp

α-2,4,6-trideoxy-4-amino-D-GalNAc-(1→4)-α-D-GalAp

α-D-GalAp-(1→3)-α-D-GalAp

α-D-GalAp

α-2,4,6-trideoxy-4-amino-D-GalNAc

α-D-GalAp-(1→3)-α-D-GalAp-(1→3)-α-2,4,6-trideoxy-4-amino-D-GalNAc

α-D-GalAp-(1→3)-α-2,4,6-trideoxy-4-amino-D-GalNAc

α-D-GalAp-(1→3)-α-2,4,6-trideoxy-4-amino-D-GalNAc-(1→4)-α-D-GalAp

Preferably, the bacterium containing in the capsular polysaccharide one of the above mentioned saccharide structures is *Streptococcus pneumoniae* type 1.

In a preferred embodiment, the glycoconjugates obtained by reacting the saccharides of general formula (I), (Ia), (Ib) and (Ic) with an immunogenic carrier are useful as a vaccine for immunization against diseases associated with bacteria, wherein said diseases include pneumonia, meningitis, otitis media, bacteremia and acute exacerbation of chronic bronchitis, sinusitis, arthritis and conjunctivitis One aspect of the present invention relates to pharmaceutical compositions, especially vaccines comprising at least one glycoconjugate obtained by reacting any saccharide of general formula (I) with an immunogenic carrier, and/or one saccharide of general formula (I) and/or a intermediate of general formula (II), together with at least one pharmaceutically acceptable cryoprotectant, lyoprotectant, excipient and/or diluent.

Said vaccine may be prepared in the form of a suspension or may be lyophilized. The suspension form may be stored frozen. In the lyophilized form, it is preferable to add one or more stabilizers. Optionally, one or more adjuvants may be added as well. Any conventional stabilizers and adjuvants may be included in a vaccine according to this invention.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the persons skilled in the art, classically recognized examples immunological adjuvants include but are not restricted to oil emulsions (e.g. Freund's adjuvant), saponins, aluminium or calcium salts (e.g. alum), non-ionic block polymer surfactants, and many others.

Vaccination can be performed at any age. The vaccine many be administered subcutaneously, by spray, by injection, orally, intraocularly, intratracheally or nasally.

Another aspect of the present invention relates to pharmaceutical formulations and pharmaceutical compositions containing the vaccine as an active ingredient, together with at least one pharmaceutically acceptable carrier, excipient, solvent and/or diluents.

Further preferred, the pharmaceutical composition is formulated in the form of a lyophilisate or liquid buffer solution.

The vaccine can also be administered in form of its pharmaceutically active salt optionally using substantially nontoxic pharmaceutically acceptable carrier, excipients, adjuvants or diluents. The vaccine of the present invention is prepared in a conventional solid or liquid carrier or diluents and a conventional pharmaceutically-made adjuvant at suitable dosage level in a known way. The preferred preparations and formulations are in administrable form, which is suitable for oral application. These administrable forms, for example, include pills, tablets, film tablets, coated tablets, capsules, powders and deposits. Other than oral administratable forms are also possible. The inventive vaccine may be administered by any appropriate means, including but not limited to inhalation; injection (intravenous, intraperitoneal, intramuscular, subcutaneous); by absorption through epithelial or mucocutaneous linings (oral mucosa, rectal and vaginal epithelial linings, nasopharyngial mucosa, intestinal mucosa); orally, rectally, transdermally, topically, intradermally, intragastrically, intracutaneously, intravaginally, intravasally, intranasally, intrabuccally, percutaneously, sublingually, or any other means available within the pharmaceutical arts.

The vaccine of the present invention, containing the glycoconjugate obtained by reacting the saccharide of general formula (I) with an immunogenic carrier or pharmaceutically acceptable salts thereof as an active ingredient will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active ingredient may be combined with any oral nontoxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture.

Suitable binders include starch, gelatin, natural sugars, corn sweeteners, natural and synthetic gums such as acacia, sodium alginate, carboxymethyl-cellulose, polyethylene glycol and waxes. Among the lubricants that may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the vaccine of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidifies.

Also included are solid form preparations that are intended to be converted, shortly before use, to liquid form preparations for either oral or parenteral administration. Such liquid forms include solutions, suspensions and emulsions.

The vaccine of the present invention may also be deliverable transdermally. The transdermal compositions may take the form of creams, lotions, aerosols and/or emulsions and can be included in a transdermal patch of the matrix or reservoir type as are conventional in the art for this purpose.

The term capsule refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet means compressed or molded solid dosage form containing the active ingredients with suitable diluents. The tablet can be prepared by compression of mixtures or granulations obtained by wet granulation, dry granulation or by compaction well known to a person skilled in the art.

Oral gels refer to the active ingredients dispersed or solubilized in a hydrophilic semi-solid matrix.

Powders for constitution refer to powder blends containing the active ingredients and suitable diluents which can be suspended in water or juices.

Suitable diluents are substances that usually make up the major portion of the composition or dosage form. Suitable diluents include sugars such as lactose, sucrose, mannitol and sorbitol, starches derived from wheat, corn rice and potato, and celluloses such as microcrystalline cellulose. The amount of diluents in the composition can range from about 5 to about 95% by weight of the total composition, preferably from about 25 to about 75%, more preferably from about 30 to about 60% by weight, and most preferably from about 40 to 50% by weight.

The term disintegrants refers to materials added to the composition to help it break apart (disintegrate) and release the medicaments. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses and cross-linked microcrystalline celluloses such as sodium croscarmellose, alginates such as alginic acid and sodium alginate, clays such as bentonites, and effervescent mixtures. The amount of disintegrant in the composition can range from about 1 to about 40% by weight of the composition, preferably 2 to about 30% by weight of the composition, more preferably from about 3 to 20% by weight of the composition, and most preferably from about 5 to about 10% by weight.

Binders characterize substances that bind or "glue" powders together and make them cohesive by forming granules, thus serving as the "adhesive" in the formulation. Binders add cohesive strength already available in the diluents or bulking agent. Suitable binders include sugars such as sucrose, starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropyl-methylcellulose; polyvinylpyrrolidone; and inorganics such as magnesium aluminum silicate. The amount of binder in the composition can range from about 1 to 30% by weight of the composition, preferably from about 2 to about 20% by weight of the composition, more preferably from about 3 to about 10% by weight, even more preferably from about 3 to about 6% by weight.

Lubricant refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and D, L-leucine. Lubricants are usually added at the very last step before compression, since they must be present on the surfaces of the granules and in between them and the parts of the tablet press. The amount of lubricant in the composition can range from about 0.05 to about 15% by weight of the composition, preferably 0.2 to about 5% by weight of the composition, more preferably from about 0.3 to about 3%, and most preferably from about 0.3 to about 1.5% by weight of the composition.

Glidents are materials that prevent caking and improve the flow characteristics of granulations, so that flow is smooth and uniform. Suitable glidents include silicon dioxide and talc. The amount of glident in the composition can range from about 0.01 to 10% by weight of the composition, preferably 0.1% to about 7% by weight of the total composition, more preferably from about 0.2 to 5% by weight, and most preferably from about 0.5 to about 2% by weight.

Coloring agents are excipients that provide coloration to the composition or the dosage form. Such excipients can include food grade dyes and food grade dyes adsorbed onto a suitable adsorbent such as clay or aluminum oxide. The amount of the colouring agent can vary from about 0.01 to 10% by weight of the composition, preferably from about 0.05 to 6% by weight, more preferably from about 0.1 to about 4% by weight of the composition, and most preferably from about 0.1 to about 1%.

Techniques for the formulation and administration of the vaccine of the present invention may be found in "Remington's Pharmaceutical Sciences" Mack Publishing Co., Easton Pa. A suitable vaccine composition comprising at least one glycoconjugate of the present invention and/or pharmaceutically acceptable salts thereof may be a solution of one glycoconjugate obtained by reacting any saccharide of general formula (I) with an immunogenic carrier in a suitable liquid pharmaceutical carrier or any other formulation such as tablets, pills, film tablets, coated tablets, dragees, capsules, powders and deposits, gels, syrups, slurries, suspensions, emulsions, and the like.

A therapeutically effective dosage of one glycoconjugate obtained by reacting any saccharide of general formula (I) with an immunogenic carrier refers to that amount of the compound that results in an at least a partial immunization against a disease.

Toxicity and therapeutic efficacy of such compounds can be determined by standard pharmaceutical, pharmacological, and toxicological procedures in cell cultures or experimental animals. The dose ratio between toxic and therapeutic effect is the therapeutic index. The actual amount of the composition administered will be dependent on the subject being treated, on the subject's weight, the severity of the affliction, the manner of administration and the judgement of the prescribing physician.

Another preferred embodiment of the present invention is directed to pharmaceutical composition comprising the glycoconjugate obtained by reacting any saccharide of general formula (I) with an immunogenic carrier, and/or the saccharide of general formula (I), and/or the intermediate of general formula (II) together with at least one one pharmaceutically acceptable cryoprotectant, lyoprotectant, excipient and/or diluent. Said pharmaceutical composition are useful in immunization against diseases associated with *Streptococcus pneumoniae* bacteria.

*Streptococcus pneumoniae* bacteria referred herein include the following serotypes *Streptococcus pneumoniae* type 1, *Streptococcus pneumoniae* type 4, *Streptococcus pneumoniae* type 9V, *Streptococcus pneumoniae* type 2, *Streptococcus pneumoniae* type 19F, *Streptococcus pneumoniae* type 3, *Streptococcus pneumoniae* type 19A, *Streptococcus pneumoniae* type 12F, *Streptococcus pneumoniae* type 31, *Streptococcus pneumoniae* type 7F, *Streptococcus pneumoniae* type 5, *Streptococcus pneumoniae* type 14, *Streptococcus pneumoniae* type 6A, *Streptococcus pneumoniae* type 6B, *Streptococcus pneumoniae* type 18C and *Streptococcus pneumoniae* type 23F.

A preferred embodiment of the present invention is directed to a pharmaceutical composition, especially a vaccine comprising the glycoconjugate obtained by reacting any saccharide of general formula (I) with an immunogenic carrier and/or the saccharide of general formula (I), and/or the intermediate of general formula (II) together with at least one one pharmaceutically acceptable cryoprotectant, lyoprotectant, excipient and/or diluents for use in immunization against diseases associated with *Streptococcus pneumoniae* type 1.

The saccharides derived from [→3)-α-2,4,6-trideoxy-4-amino-D-GalNAc-(1→4)-α-D-GalAp-(1→3)-α-D-GalAp-(1→] are functionalized with suitable linker, which allows their conjugation to an immunogenic carrier, as defined herein to provide glycoconjugates. Said glycoconjugates proved to be efficient as a vaccine for immunization against diseases associated with bacteria, and in particularly against diseases associated with *Streptococcus pneumoniae*, and particularly against *Streptococcus pneumoniae* type 1. Said diseases include pneumonia, meningitis, otitis media, bacteremia and acute exacerbation of chronic bronchitis, sinusitis, arthritis and conjunctivitis.

Yet another aspect of the present invention refers to saccharide of general formula (I) and/or intermediate of general formula (II) for use as a marker in immunological assays for diagnostics of diseases caused by bacteria containing in the capsular polysaccharide a saccharide structure selected from:

α-2,4,6-trideoxy-4-amino-D-GalNAc-(1→4)-α-D-GalAp-(1→3)-α-D-GalAp

α-2,4,6-trideoxy-4-amino-D-GalNAc-(1→4)-α-D-GalAp

α-D-GalAp-(1→3)-α-D-GalAp

α-D-GalAp

α-2,4,6-trideoxy-4-amino-D-GalNAc
α-D-GalAp-(1→3)-α-D-GalAp-(1→3)-α-2,4,6-trideoxy-4-amino-D-GalNAc
α-D-GalAp-(1→3)-α-2,4,6-trideoxy-4-amino-D-GalNAc
α-D-GalAp-(1→3)-α-2,4,6-trideoxy-4-amino-D-GalNAc-(1→4)-α-D-GalAp Such assays comprise, for instance, microarray and ELISA useful for diagnosis of diseases caused by bacteria containing or comprising the saccharides of the present invention, said diseases including pneumonia, meningitis, otitis media, bacteremia and acute exacerbation of chronic bronchitis, sinusitis, arthritis and conjunctivitis.

The saccharides of the present invention can be easily conjugated to solid supports for providing assays useful for diagnosis of diseases caused by bacteria containing or comprising the saccharides of the present invention. Said solid supports present on their surface a functionality that is prone to react with the functional group Y of the interconnecting molecule to provide modified solid supports, presenting on their surface the functional group X of the interconnecting molecule, which are able to react with the thiol group of saccharides of general formula (I). Said solid supports include, but are not restricted to microarray slides, which present on their surface a functionality that is prone to react with the functional group Y of the interconnecting molecule to provide modified microarray slides, presenting of their surface the functional group X of the interconnecting molecule. Preferably, the microarray slides present on their surface an amino group. Microarray slides presenting on their surface an amino group include, but are not restricted to amine-coated GAPS II slides (Corning) or CodeLink NHS slides on which the amino functionality was introduced by incubation with Bovin Serum Albumin (BSA).

Microarray slides coated with the saccharides of general formula (I) were synthesized by conjugating the saccharides of general formula (I) to said modified microarray slides, and incubated with rabbit anti-*Streptococcus pneumoniae* type 1 typing serum human pneumococcal serum 007sp in the presence or absence of native *Streptococcus pneumoniae* type 1 polysaccharide. The binding experiments show that both rabbit anti-*Streptococcus pneumoniae* type 1 typing serum and human pneumococcal serum 007sp bound to α-2,4,6-trideoxy-4-amino-D-GalNAc-(1→4)-α-D-GalAp-(1→3)-α-D-GalAp and α-D-GalAp-(1→3)-α-D-GalAp saccharide structures (see FIGS. 4-8). Moreover, the binding could be inhibited with the native *Streptococcus pneumoniae* type 1 polysaccharide, suggesting that the saccharides according to the present invention share epitopes that are recognized by the immune system (see FIG. 5 and FIG. 6).

DESCRIPTION OF THE FIGURES

FIG. 4 shows the printing pattern of the saccharides of general formula (I) on microarray slides FIG. 5 shows the binding of human pneumococcal serum 007sp (pooled sera of 287 humans immunized with Pneumovax vaccine) to saccharides of general formula (I), which are coated on modified CodeLink NHS slides in presence and in absence of native *Streptococcus pneumoniae* type 1 polysaccharide.

FIG. 6 shows the binding of the rabbit anti-*Streptococcus pneumoniae* type 1 typing serum to saccharides of general formula (I), which are coated on modified amine-coated GAPS II slides (Corning) in presence and in absence of native *Streptococcus pneumoniae* type 1 polysaccharide.

Figure 1:
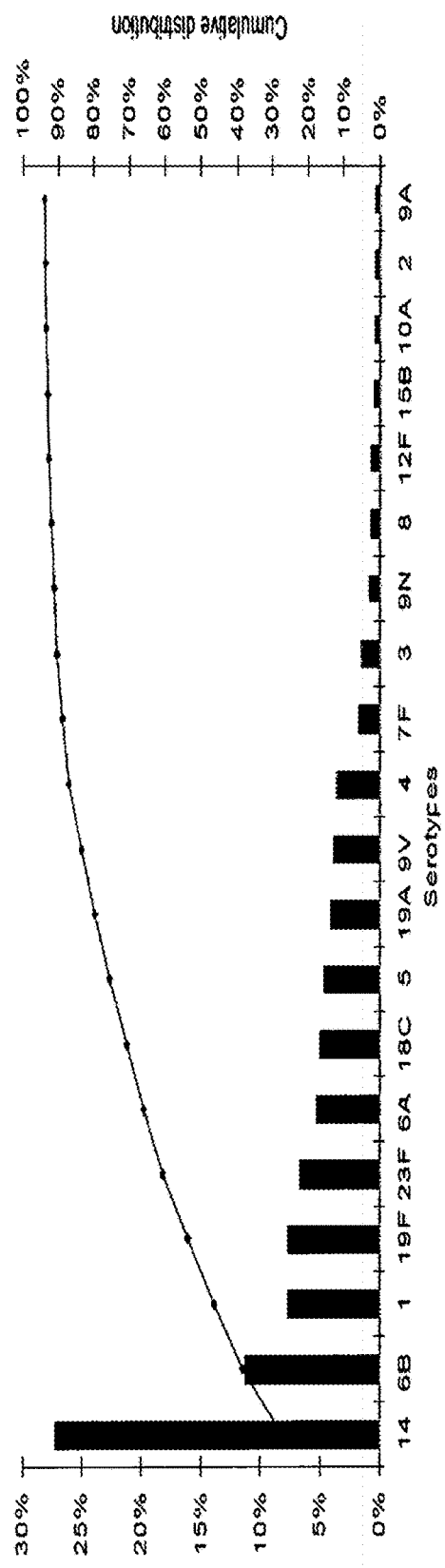
FIG. 1 shows the global distribution of *Streptococcus pneumoniae* serotypes
Figure 3:
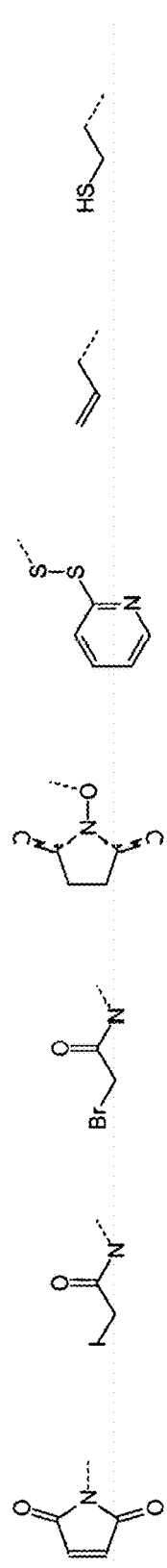
FIG. 3 provides examples of functional group X of the interconnecting molecule according to the present invention.
Figure 2:
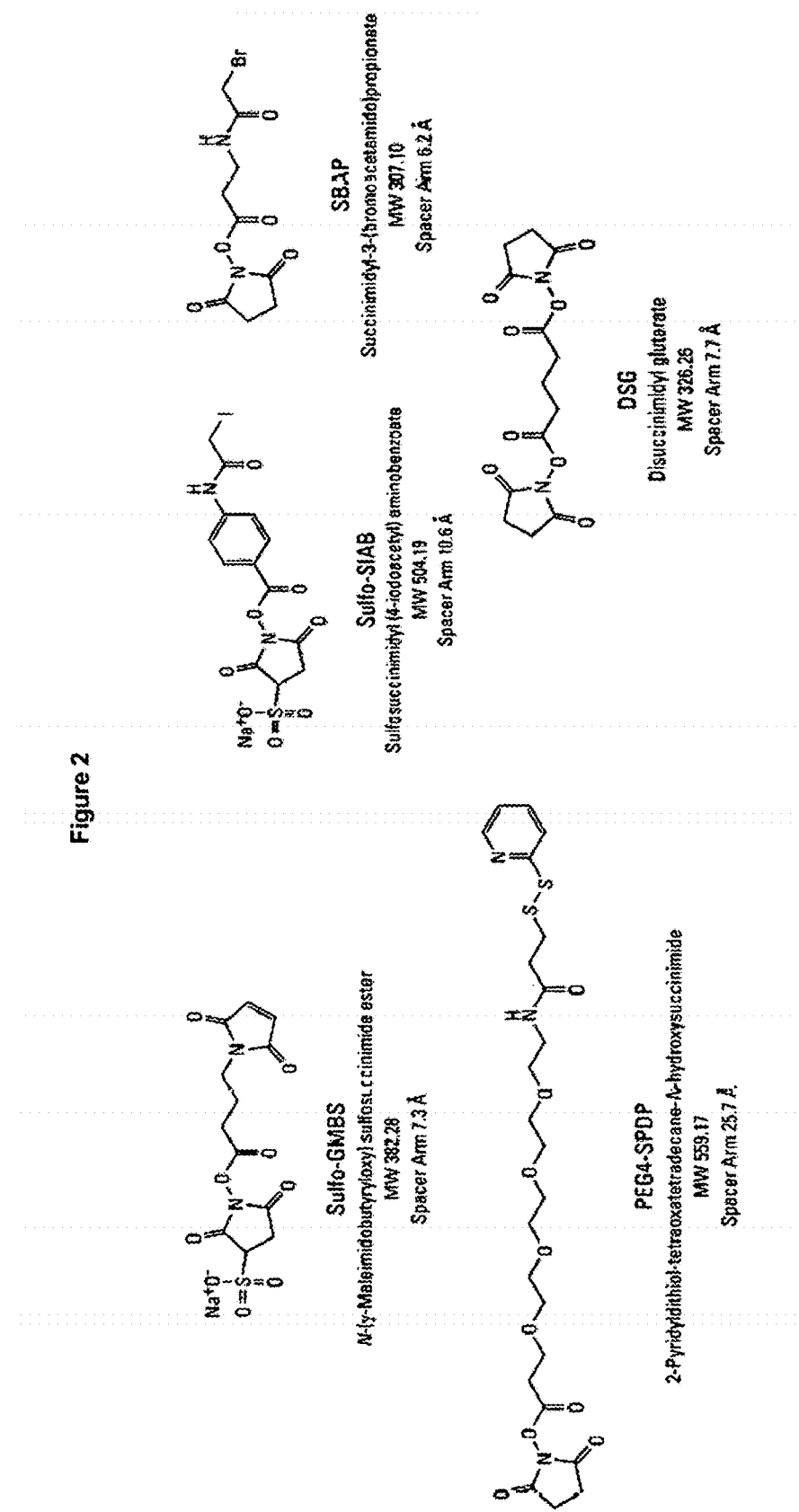
FIG. 2 provides examples of commercially available interconnecting molecules according to the present invention.
Figure 7:
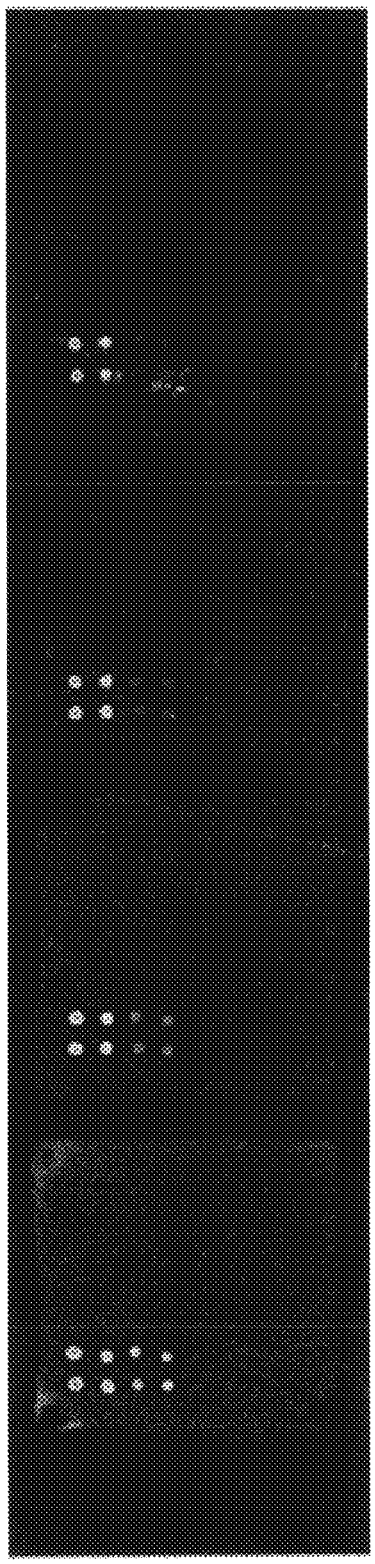
FIG. 7 shows the binding of the rabbit anti-*Streptococcus pneumoniae* type 1 typing serum to saccharides of general formula (I), which are coated on modified amine-coated GAPS II slides (Corning).
Figure 8:
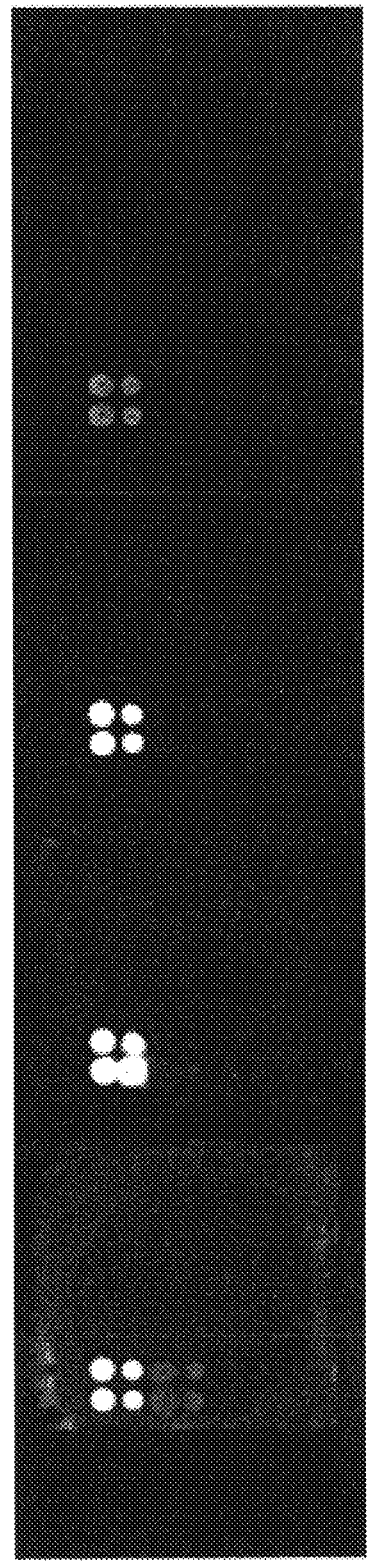
FIG. 8 shows the binding of the rabbit anti-*Streptococcus pneumoniae* type 1 typing serum to saccharides of general formula (I), which are coated on modified CodeLink NHS slides.

The following examples are included to demonstrate preferred embodiments of the invention. It should be appreciated by those skilled in the art that the techniques disclosed in the examples, which follow represent techniques discovered by the inventor to function well in the practice of the invention, and thus can be considered to constitute preferred modes for its practice. However, those skilled in the art should, in light of the present disclosure, appreciate that many changes can be made in the specific embodiments, which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Chemical Synthesis

General information for chemical synthesis. Commercial reagents were used without further purification except where noted. Solvents were dried and redistilled prior to use in the usual way. All reactions were performed in oven-dried glassware under an inert atmosphere unless noted otherwise. Analytical thin layer chromatography (TLC) was performed on Kieselgel 60 F254 glass plates precoated with a 0.25 mm thickness of silica gel. The TLC plates were visualized with UV light and by staining with Hanessian solution (ceric sulfate and ammonium molybdate in aqueous sulfuric acid) or sulfuric acid-ethanol solution. Column chromatography was performed on Fluka Kieselgel 60 (230-400 mesh). Optical rotations (OR) were measured with a Schmidt & Haensch UniPol L1000 polarimeter at a concentration (c) expressed in g/100 mL. $^1$H and $^{13}$C NMR spectra were measured with a Varian 400-MR or Varian 600 spectrometer with Me$_4$Si as the internal standard. NMR chemical shifts (δ) were recorded in ppm and coupling constants (J) were reported in Hz. High-resolution mass spectra (HRMS) were recorded with an Agilent 6210 ESI-TOF mass spectrometer at the Freie Universität Berlin, Mass Spectrometry Core Facility.

Example 1

4-(Benzyloxycarbonyl)amino-3-O-levulinoyl-4,6-dideoxy-D-galactal (1*)

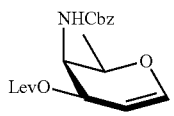

To a stirred solution of 4-O-(benzyloxycarbonyl)amino-3-hydroxy-4,6-dideoxy-D-galactal (*Org. Lett.* 2010, 12, 1624) (1.64 g, 6.21 mmol) (1.64 g, 6.21 mmol) in $CH_2Cl_2$ (40 ml) were added at 0° C. pyridine (0.501 ml, 6.21 mmol), levulinic acid (0.96 ml, 9.31 mmol), DMAP (0.152 g, 1.242 mmol) and EDC (1.205 ml, 6.83 mmol). The mixture was warmed to room temperature and stirred at that temperature. After 3 h, 0.5 eq. levulinic acid and 0.5 eq. EDC were added to drive the reaction to completion. After 5 h, the mixture was diluted with 100 ml DCM and washed with water (50 ml), sat. aq. $NH_4Cl$ (50 ml), sat. aq. $NaHCO_3$ (50 ml) and brine (50 ml). The organic fraction was dried over $Na_2SO_4$ and concentrated. The residue was purified by flash chromatography (EtOAc/hexanes 1:1) to give ester 1* (2.07 g, 5.73 mmol, 92%) as a clear oil. HRMS (ESI) calcd for $C_{19}H_{23}NO_6$ (M+Na+) 384.1423. found 384.1415 m/z.

Example 2

Dibutyl [2-azido-4-(benzyloxycarbonyl)amino-3-O-levulinoyl-2,4,6-trideoxy-D-galactopyranosyl] phosphate (2*)

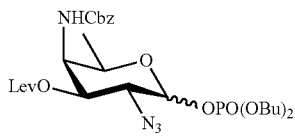

To a stirred solution of galactal 1* (3.17 g, 8.77 mmol) in dry MeCN (44 ml) were added at −25° C. ceric ammonium nitrate (14.42 g, 26.3 mmol) and sodium azide (0.86 g, 13.15 mmol). The reaction was stirred vigorously between −25° C. and −20° C. for 6 h. The mixture was diluted with cold $Et_2O$ (50 ml). The organic layer was washed with cold water (3×30 ml), dried over $Na_2SO_4$ and concentrated. The residue was filtered through a plug of silica gel (EtOAc/hexanes/$Et_3N$ 1:1:0.01) to give the crude glycosyl nitrate as 4:1 galacto/talo mixture (2.01 g) as a slightly yellow oil.

To the crude glycosyl nitrate (2.01 g) was added at room temperature a solution of cesium dibutyl phosphate (2.21 g, 6.45 mmol) in dry DMF (28 ml). The mixture was stirred at that temperature for 4.5 h, diluted with EtOAc (100 ml) and poured into water (100 ml). The organic phase was washed with water (5×50 ml) and the combined aqueous fractions were re-extracted with EtOAc (50 ml). The organic phase was dried over $Na_2SO_4$ and concentrated. The residue was purified by flash chromatography (EtOAc/hexanes 45:55 to 50:50) to give glycosyl phosphate 2* (1.84 g, 3.00 mmol, 37%, 1:10 α/β) as a clear oil. HRMS (ESI) calcd for $C_{27}H_{41}N_4O_{10}P$ (M+Na+) 635.2458. found 635.2422 m/z.

Example 3

Ethyl 2-O-benzyl-3,4-isopropylidene-1-thio-β-D-galactopyranoside (3*)

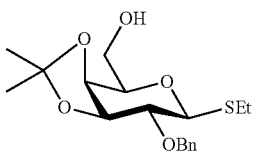

To a stirred solution of ethyl 6-O-tert-butyldimethylsilyl-3,4-isopropylidene-1-thio-β-D-galactopyranoside (*Bioorg. Med. Chem.* 2001, 9, 1395) (45.7 g, 121 mmol) in DMF (150 ml) and THF (75 ml) were added at 0° C. portionwise sodium hydride (60%, 7.24 g, 181 mmol) and then benzyl bromide (17.2 ml, 145 mmol). The mixture was stirred for 1 h at 0° C., slowly warmed to room temperature and stirred for 16 h at that temperature. The reaction was quenched at 0° C. with sat. aq. $NH_4Cl$ (20 ml), diluted with water (200 ml) and EtOAc (150 ml) and stirred for 15 min at 0° C. After separation, the organic phase was washed with water (5×100 ml) and the combined aqueous fractions were re-extracted with EtOAc (2×100 ml). The combined organic extracts were dried over $Na_2SO_4$ and concentrated to give the crude benzyl ether (61 g) as a yellow oil.

To a stirred solution of the crude benzyl ether (61 g) in THF (370 ml) was added at 0° C. tetrabutylammonium fluoride (1 M in THF, 166 ml, 166 mmol). The mixture was warmed to room temperature and stirred for 1 h. The reaction was diluted with sat. aq. $NaHCO_3$ (200 ml) and EtOAc (100 ml). After separation, the aqueous phase was extracted with EtOAc (3×100 ml), the combined organic fractions were dried over $MgSO_4$ and concentrated. The residue was purified by flash chromatography (EtOAc/hexanes 0:1 to 1:3 to 1:1) to give alcohol 3* as a white solid. HRMS (ESI) calcd for $C_{18}H_{26}O_5S$ (M+Na+) 377.1398. found 377.1416 m/z.

Example 4

Methyl (ethyl 2-O-benzyl-1-thio-β-D-galactopyranosid)uronate (4*)

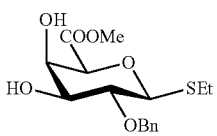

To a vigorously stirred solution of alcohol 4* (6.0 g, 16.93 mmol) in $CH_2Cl_2$ (50 ml) and $H_2O$ (25 ml) were added at 0° C. TEMPO (0.53 g, 3.39 mmol) and BAIB (10.9 g, 33.9 mmol). The mixture was warmed to room temperature and stirred for 1 h at that temperature. The reaction was quenched with 10% aq. $Na_2S_2O_3$ (10 ml) and diluted with EtOAc (30 ml). After separation, the organic phase was washed with 10% $Na_2S_2O_3$ (4×20 ml). The aqueous phase was extracted with EtOAc (2×20 ml) and the combined organic fractions were dried over $Na_2SO_4$ and concentrated to give the crude acid (7.92 g) as yellow oil.

To a stirred solution of acetyl chloride (6.04 ml, 85 mmol) in MeOH (300 ml) was added dropwise at 0° C. a solution of the crude acid (7.92 g) in MeOH (40 ml). The mixture was warmed to room temperature, stirred for 2 h at that temperature and cooled to 0° C. The reaction was quenched with sat. aq. NaHCO3 (30 ml) and neutralized to pH 7 with solid NaHCO$_3$. The volatiles were evaporated and the mixture was diluted with EtOAc (70 ml). After separation, the aqueous phase was extracted with EtOAc (5×50 ml). The combined organic fractions were dried over Na$_2$SO$_4$ and concentrated. Flash chromatography was performed (EtOAc/hexanes 2:3 to 1:1, then 1:0) to give the crude product, which was crystallized in methanol at −20° C. (5 ml/g crude product) to give diol 4* (3.47 g, 10.13 mmol, 60%) as a white solid. HRMS (ESI) calcd for $C_{16}H_{22}O_6S$ (M+Na)$^+$ 365.1034. found 365.1058 m/z.

Example 5

Methyl (ethyl 2-O-benzyl-3,4-O-endo-benzylidene-1-thio-β-D-galactopyranosid)urinate (5*) and Methyl (ethyl 2-O-benzyl-3,4-O-exo-benzylidene-1-thio-β-D-galactopyranosid)uronate (6*)

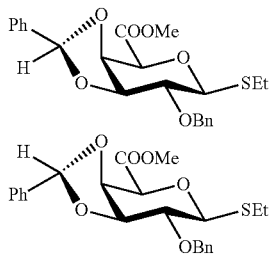

To a stirred solution of diol 4* (2.99 g, 8.73 mmol) in dry acetonitrile (29 ml) were added at room temperature benzaldehyde dimethyl acetal (6.57 ml, 43.6 mmol) and DL-camphorsulfonic acid (0.51 g, 2.18 mmol). The mixture was stirred at room temperature for 5 h and the reaction was quenched by addition of triethylamine (0.35 ml). The mixture was concentrated under reduced pressure to give a residue, which was filtered through a short plug of silica gel (hexanes/EtOAc 8:1 (2% Et$_3$N) to 1:1 (2% Et$_3$N)) to give a 1:1 mixture of benzylidene acetals 5* (endo) and 6* (exo) (3.46 g, 8.03 mmol, 92%). The isomers were separated by selective crystallization of exo-isomer 6* from EtOAc/hexanes and chromatographic separation of the mother liquor (Biotage, flat gradient of 10% to 40% EtOAc in hexanes+0.5% Et$_3$N). Analytical data for 5*: Clear oil. HRMS (ESI) calcd for $C_{23}H_{26}O_6S$ (M+Na)$^+$ 453.1348. found 453.1352 m/z. Analytical data for 6*: White solid. HRMS (ESI) calcd for $C_{23}H_{26}O_6S$ (M+Na)$^-$ 453.1348. found 453.1338 m/z.

Example 6

Methyl (ethyl 2,3-O-benzyl-1-thio-β-D-galactopyranosyl)uronate (7*)

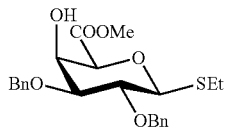

To a solution of acetal 6* (162 mg, 0.38 mmol) and sodium cyanoborohydride (296 mg, 4.70 mmol) in THF (9.4 ml) was added at room temperature a solution of hydrogen chloride (1 M in Et$_2$O) until the evolution of gas ceased. After 10 min, sodium cyanoborohydride (296 mg, 4.70 mmol) was added, followed by the addition of HCl. The reaction was stirred at room temperature, diluted with EtOAc (30 ml) and quenched with sat. aq. NaHCO$_3$ (30 ml). After separation, the organic layer was washed with sat. aq. NaHCO$_3$ (20 ml) and the aqueous layer was re-extracted with EtOAc (2×20 ml). The organic extracts were pooled, dried over MgSO$_4$ and concentrated. The residue was purified by flash chromatography (EtOAc/hexanes 1:1) to give alcohol 7* (67.5 mg, 0.156 mmol, 42%) as a white solid. HRMS (ESI) calcd for $C_{23}H_{28}O_6S$ (M+Na$^+$) 455.1504. found 455.1511 m/z.

Example 7

Methyl (ethyl 2,3-O-benzyl-4-O-fluorenylmethoxycarbonyl-1-thio-β-D-galactopyranosyl uronate (8*)

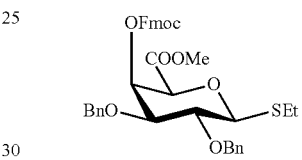

To a stirring solution of alcohol 7* (160 mg, 0.370 mmol) in pyridine (1.2 ml) was added at 0° C. FmocCl (383 mg, 1.48 mmol). The mixture was warmed to room temperature and stirred for 3 h. The mixture was then diluted with EtOAc (50 ml) and washed with 1 N HCl (2×30 ml) and sat. aq. NaHCO$_3$ (30 ml). The organic phase was dried over Na$_2$SO$_4$ and concentrated. The residue was purified by flash chromatography (EtOAc/hexanes 1:2) to give carbonate 8* (217 mg, 0.331 mmol, 90%) as a white foam. HRMS (ESI) calcd for $C_{38}H_{38}O_8S$ (M+Na)$^+$ 677.2185. found 677.2167 m/z.

Example 8

Dibutyl [methyl (2,3-O-benzyl-4-O-fluorenylmethoxycarbonyl-α/β-D-galactopyranosyl)uronate] phosphate (9*)

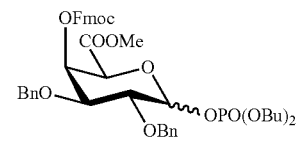

Thioglycoside 8* (200 mg, 0.305 mmol) was co-evaporated with dry toluene (2×30 ml), kept under high vacuum for 1 h and dissolved in dry CH$_2$Cl$_2$ (3 ml). Activated molecular sieves (3 Å-AW) were added and the solution was stirred for 15 min at room temperature. The solution was then cooled to 0° C., treated with dibutyl phosphoric acid (128 mg, 0.611 mmol) and stirred for another 15 min. The mixture was then treated with NIS (89 mg, 0.397 mmol), warmed to room temperature and stirred for 3 h at that temperature. The reaction was diluted with CH$_2$Cl$_2$ (20 ml) and quenched with a 1:1 (v/v) mixture of 10% aq. Na$_2$S$_2$O$_3$ and sat. aq. NaHCO$_3$ (20 ml). The aqueous phase was extracted with CH$_2$Cl$_2$ (3×30 ml), the combined organic fractions were dried over Na$_2$SO$_4$ and concentrated. The residue was purified by flash chromatography (EtOAc/hexanes 1:1 to 2:1) to give glycosyl phosphate 9* (218 mg, 0.272 mmol, 89%, 10:1 α/β as clear oil. Analytical data of 9*α: HRMS (ESI) calcd for C$_{44}$H$_{51}$O$_{12}$P (M+Na)$^+$ 825.3015. found 825.3020 m/z. Analytical data of 9*β: HRMS (ESI) calcd for C$_{44}$H$_{51}$O$_{12}$P (M+Na)$^+$825.3015. found 825.2970 m/z.

Example 9

Methyl (2-O-benzyl-3,4-O-endo-benzylidene-α/β-D-galactopyranosyl)uronate-(1→1)-2-(benzylthio)ethanol (10*)

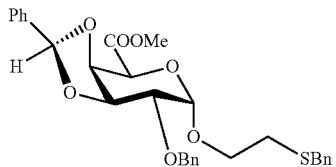

Thioglycoside 5* (102 mg, 0.237 mmol), 2-(benzylthio)ethanol 11* (60 mg, 0.355 mmol) and TTBPy. (117 mg, 0.474 mmol) were co-evaporated with anh. toluene (3×10 ml) and kept under high vacuum for 30 min. The mixture was dissolved in THF (4.8 ml) and stirred over activated molecular sieves (3 Å) for 30 min at room temperature. The solution was cooled to 0° C. and treated with DMTST (92 mg, 0.355 mmol in 0.2 ml dry CH$_2$Cl$_2$). The reaction was warmed to room temperature and stirred for 2 h at that temperature. The reaction was quenched with a 1:1 (v/v) MeOH/Et$_3$N mixture (0.1 ml) and concentrated. The residue was purified by flash chromatography (EtOAc/hexanes/Et$_3$N 0:1:0.01 to 30:70:0.01 to 45:55:0.01) to give thioether 10*α (59 mg, 0.110 mmol, 46%) as a clear oil, along with the corresponding β-isomer 10*β (35 mg, 0.065 mmol, 27%). Analytical data for 10*α: HRMS (ESI) calcd for C$_{30}$H$_{32}$O$_7$S (M+Na)$^+$559.1766. found 559.1731 m/z.

Example 10

Methyl (2,4-di-O-benzyl-α-D-galactopyranosid)uronate-(1→1)-2-(benzylthio)ethanol (12*)

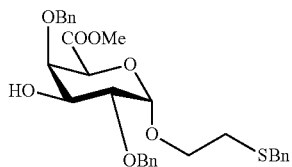

To a stirred solution of acetal 10*a (100.0 mg, 0.186 mmol) in dry THF (5.3 ml) was added first borane trimethylamine complex (57.4 mg, 0.745 mmol) and then aluminium chloride (149 mg, 1.118 mmol) at room temperature. The mixture was stirred for 4.5 h. The reaction was quenched by addition of water (10 ml) and 1 M aq. HCl (5 ml). The mixture was extracted with EtOAc (3×10 ml) and the combined organic fractions were dried over Na$_2$SO$_4$ and concentrated. The residue was purified by flash chromatography (EtOAc/hexanes 2:5 to 1:1) to give alcohol 12* (70.0 mg, 0.13 mmol, 70%) as a clear oil. HRMS (ESI) calcd for C$_{30}$H$_{34}$O$_7$S (M+Na)$^+$561.1923. found 561.1879 m/z.

Example 11

Methyl (2,3-di-O-benzyl-α-D-galactopyranosyl)uronate-(1→3)-methyl (2,4-di-O-benzyl-α-D-galactopyranosyl)uronate-(1→3)-(2-(benzylthio)ethanol (13*)

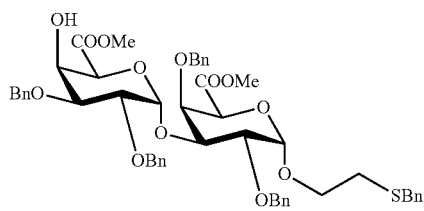

Alcohol 12* (90 mg, 0.166 mmol) and glycosyl phosphate 9* (208 mg, 0.259 mmol) were co-evaporated with dry toluene (3×10 ml) and kept under high vacuum for 1 h. The mixture was dissolved in dry CH$_2$Cl$_2$ (3.3 ml) and stirred over activated molecular sieves (3 Å-AW) for 30 min at room temperature. The solution was cooled to 0° C. and treated dropwise with TBSOTf (0.133 mmol in 0.2 ml dry CH$_2$Cl$_2$). The solution was warmed to room temperature and stirred for 20 h. The reaction was diluted with CH$_2$Cl$_2$ (10 ml) and quenched with a 1:1 (v/v) MeOH/pyridine mixture (0.2 ml). The solution was filtered through Celite and concentrated. The crude product was filtered through a short plug of silica gel (EtOAc/hexanes 1:1) to give the intermediate disaccharide mixture (150 mg, 0.133 mmol, 80%, 3:1 α/β) as a clear oil.

To a stirred solution of the carbonate mixture (150 mg) in CH$_2$Cl$_2$ (2.6 ml) was added at room temperature triethylamine (1.1 ml, 7.96 mmol). The reaction was stirred for 3 h at that temperature and co-evaporated with toluene (2×10 ml). The residue was purified by flash chromatography (EtOAc/hexanes 1:6 to 2:3 to 1:1) to give alcohol 13* (62 mg, 0.068 mmol, 51%) along with the corresponding β-anomer (20 mg, 0.022 mmol, 17%). HRMS (ESI) calcd for C$_{51}$H$_{56}$O$_{13}$S (M+Na)$^+$931.3339. found 931.3340 m/z.

Example 12

2-Azido-4-(benzyloxycarbonyl)amino-3-O-levulinoyl-2,4,6-trideoxy-α-D-galactopyranosyl-(1→4)-methyl (2,3-di-O-benzyl-α-D-galactopyranosyl)uronate-(1→3)-methyl (2,4-di-O-benzyl-α-D-galactopyranosyl)uronate-(1→1)-2-(benzylthio)ethanol (14*)

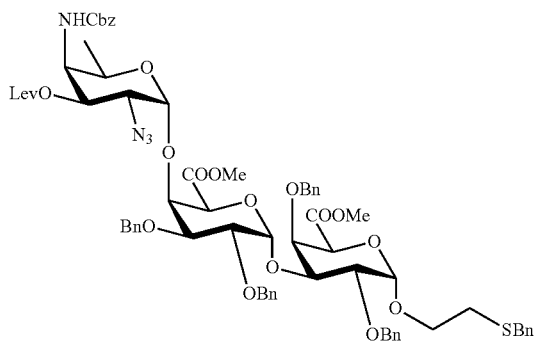

Alcohol 13* (65 mg, 0.062 mmol) and glycosyl phosphate 2* (61 mg, 0.100 mmol) were co-evaporated with dry toluene (3×10 ml) and kept under high vacuum for 30 min. The mixture was dissolved in CH$_2$Cl$_2$ (2.1 ml) and stirred over activated molecular sieves (4 Å-AW) for 1 h at room temperature. The solution was then cooled to 0° C. and treated with TMSOTf (17 μl, 0.093 mmol in 0.2 ml dry CH$_2$Cl$_2$). The mixture was allowed to stir for 3 h at 0° C., when TLC (EtOAc/hexanes 2:3) indicated complete consumption of the acceptor. The reaction was quenched with a 1:1 (v/v) MeOH/NEt$_3$ mixture (0.5 ml), diluted with CH$_2$Cl$_2$ (20 ml) and filtered through Celite. The crude product was purified by flash chromatography (EtOAc/hexanes 1:2 to 1:1) to give trisaccharide 14* (69 mg, 0.053 mmol, 85%) as a clear oil. HRMS (ESI) calcd. for C$_{70}$H$_{78}$N$_4$O$_{19}$S (M+Na)$^+$ 1333.4879. found 1333.4911 m/z.

Example 13

2-Azido-4-(benzyloxycarbonyl)amino-2,4,6-trideoxy-α-D-galactopyranosyl-(1→4)-methyl (2,3-di-O-benzyl-α-D-galactopyranosyl)uronate-(1→3)-methyl (2,4-di-O-benzyl-α-D-galactopyranosyl)uronate-(1→1)-2-(benzylthio)ethanol (15*)

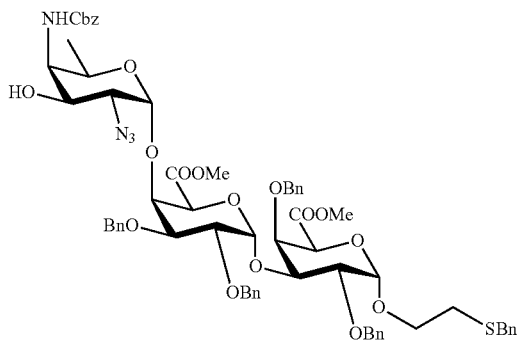

To a stirred solution of levulinoyl ester 14* (30 mg, 0.023 mmol) in dry CH$_2$Cl$_2$ (1.0 ml) was added at room temperature first a mixture of pyridine (56 μl, 0.692 mmol) and acetic acid (37 μl, 0.646 mmol), and then hydrazine hydrate (2 μl, 0.041 mmol). The mixture was allowed to stir for 4 h at room temperature, diluted with EtOAc (2 ml), quenched with acetone (0.1 ml) and poured into water (15 ml). The aqueous phase was extracted with EtOAc (4×10 ml), and the combined organic extracts were dried over Na$_2$SO$_4$ and concentrated under reduced pressure. The residue was purified by flash chromatography (EtOAc/hexanes 0:1 to 1:2 to 2:3) to give alcohol 15* (28 mg, 0.023 mmol, 100%) as a clear oil. HRMS (ESI) calcd. for C$_{65}$H$_{72}$N$_4$O$_{17}$S (M+Na)$^+$ 1235.4511. found 1235.4539 m/z.

Example 14

2-Azido-4-(benzyloxycarbonyl)amino-3-O-benzyloxymethyl-2,4,6-trideoxy-α-D-galactopyranosyl-(1→4)-methyl (2,3-di-O-benzyl-α-D-galactopyranosyl)uronate-(1→3)-methyl (2,4-di-O-benzyl-α-D-galactopyranosyl)uronate-(1→1)-2-(benzylthio)ethanol (16*)

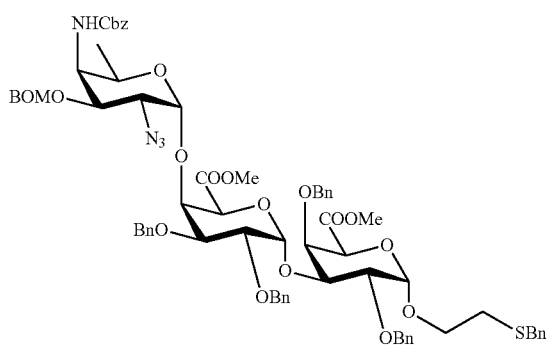

Alcohol 15* (8.6 mg, 7.1 μmol), benzyloxymethyl thiocyclohexane (79 mg, 0.354 mmol) and TTBPy. (105 mg, 0.425 mmol) were coevaproated with dry toluene (3×10 ml) and kept under high vacuum for 30 min. The mixture was dissolved in dry CH$_2$Cl$_2$ (0.4 ml) and stirred over activated molecular sieves (3 Å) for 30 min at room temperature. The mixture was cooled to 0° C. and DMTST (7.1 mg, 0.18 mmol in 0.1 ml CH$_2$Cl$_2$) was added dropwise over 45 min, while the reaction temperature was kept below 10° C. The reaction was stirred for another 45 min, quenched by addition of a 1:1 (v/v) MeOH/Et$_3$N mixture and concentrated. The residue was purified by flash chromatography (EtOAc/hexanes 1:10 to 1:2) to give acetal 16* (6.0 mg, 4.5 μmol, 64%) as a clear oil. HRMS (ESI) calcd for C$_{73}$H$_{80}$N$_4$O$_{18}$S (M+Na)$^+$1355.5086. found 1355.5071 m/z.

Example 15

2-Acetamido-4-(benzyloxycarbonyl)amino-3-O-benzyloxymethyl-2,4,6-trideoxy-α-D-galactopyranosyl-(1→4)-methyl (2,3-di-O-benzyl-α-D-galactopyranosyl)uronate-(1→3)-methyl (2,4-di-O-benzyl-α-D-galactopyranosyl)uronate-(1→1)-2-(benzylthio) ethanol (17*)

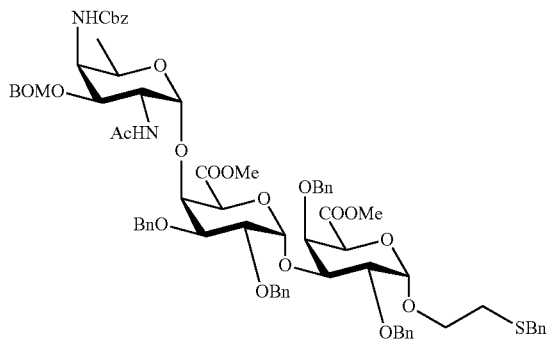

To a stirred solution of azide 16* (14.0 mg, 10.5 μmol) in dry pyridine (0.35 ml) was added at 0° C. thioacetic acid (0.35 ml). The mixture was warmed to room temperature and stirred for 24 h at that temperature. The solution was co-evaporated with toluene (2×5 ml) and the residue was purified by flash chromatography (EtOAc/hexanes 1:10 to acetone/hexanes 1:7 to 1:5 to 1:3) to give acetamide 17* (9.4 mg, 7.0 μmol, 66%) as a white solid. HRMS (ESI) calcd for $C_{75}H_{84}N_2O_{19}S$ (M+Na)$^+$1371.5281. found 1371.5314 m/z.

Example 16

2,2'-Dithiobis[2-acetamido-4-amino-2,4,6-trideoxy-α-D-galactopyranosyl-(1→4)-α-D-galactopyranosyluronate-(1→3)-α-D-galactopyranosyluronate-(1→1)-1-ethanol] (18*)

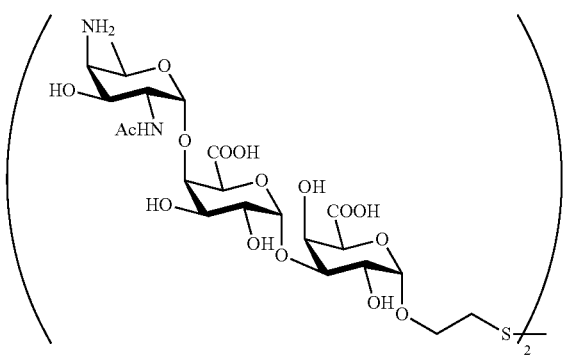

To a stirred solution of diester 17* in THF (4.0 ml) and MeOH (0.8 ml) was added at 0° C. a 1 M solution of NaOH in water (1.5 ml). The reaction was slowly warmed to room temperature and stirred for 16 h. The reaction was diluted with EtOAc (5 ml) and acidified to pH 4 with 0.5 M aq. NaHSO$_4$. After separation, the aqueous fraction was extracted with EtOAc (8×10 ml), the combined organic fractions were dried over Na$_2$SO$_4$ and concentrated to give the intermediate diacid as a white solid.

To a stirring solution of liquid ammonia (5 ml) was added at −78° C. a solution of the crude diacid in THF (1.5 ml). The mixture was treated with tBuOH (0.5 ml) and lumps of freshly cut sodium (45 mg) were added until a deeply blue color persisted. The reaction was stirred at −78° C. for 45 min and quenched by addition of solid ammonium acetate (200 mg). The solution was warmed to room temperature under a stream of argon and co-evaporated with MeOH (2×10 ml) and water (2×5 ml). The residue was left under air for 16 h, purified by size exclusion chromatography (Sephadex G-25, 1:1 MeOH/5 mM aq. NH$_4$OAc) and lyophilized repeatedly to give disulfide 18* (1.4 mg, 1.65 μmol, 32%) as a white solid. HRMS (MALDI) calcd for $C_{44}H_{70}N_4O_{32}S_2$ (M−H$^+$) 1229.3330. found 1229.3342 m/z.

Example 17

Methyl (ethyl 2,3-O-benzyl-4-O-levulinoyl-1-thio-β-D-galactopyranosyl)uronate (19*)

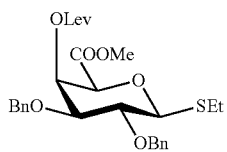

To a stirred solution of alcohol 7* (94 mg, 0.217 mmol) in CH$_2$Cl$_2$ (1.9 mL) were added at room temperature levulinic acid (386 mg, 3.26 mmol), DCC (673 mg, 3.26 mmol) and pyridine (0.26 mL, 3.26 mmol). The mixture was stirred at that temperature for 35 h, diluted with CH$_2$Cl$_2$ (5 mL) and filtered through Celite. The mixture was concentrated, the residue was dissolved in a minimal volume of CH$_2$Cl$_2$ (1-3 mL) and filtered through cotton wool. The same procedure was repeated 3 times. The residue was purified by flash chromatography (EtOAc/toluene 1:1) to give ester 19* (91 mg, 0.171 mmol, 79%) as a slightly yellow oil. HRMS (ESI) calcd for $C_{28}H_{34}O_8S$ (M+Na)$^+$ 553.1872. found 553.1872 m/z.

Example 18

Methyl (2,3-di-O-benzyl-α-D-galactopyranosid)uronate-(1→1)-6-(benzylthio)hexanol (20*)

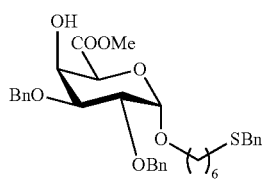

Thioglycoside 19* (87 mg, 0.164 mmol), 6-(benzylthio)hexanol 21* (85 mg, 0.379 mmol) and TTBPy. (97 mg, 0.392 mmol) were co-evaporated with anh. toluene (3×10 ml) and kept under high vacuum for 30 min. The mixture was dissolved in Et$_2$O (2.5 ml) and CH$_2$Cl$_2$ (0.83 ml) and stirred over activated molecular sieves (3 Å) for 30 min at room temperature. The solution was cooled to 0° C. and treated with DMTST (63.5 mg, 0.246 mmol). The reaction was warmed to room temperature and stirred for 8 h at that temperature. The reaction was quenched with a 1:1 (v/v) mixture of MeOH and triethylamine (0.1 ml) and concentrated. The residue was purified by flash chromatography (EtOAc/CH$_2$Cl$_2$/hexanes 0:0:1 to 1:2:1) to give the corresponding glycosides (60 mg) as an inseparable α/β mixture.

To a stirred solution of the glycoside mixture in dry CH$_2$Cl$_2$ (2.2 ml) were added at room temperature first a mixture of pyridine (195 μl, 2.411 mmol) and acetic acid (137 μl, 2.393 mmol), and then hydrazine hydrate (5.9 μl, 0.121 mmol). The mixture was stirred for 2 h at that temperature, diluted with EtOAc (2 ml), quenched with acetone (0.1 ml) and poured into water (15 ml). The aqueous phase was extracted with EtOAc (4×10 ml), the combined organic extracts were dried over Na$_2$SO$_4$ and concentrated. The residue was purified by flash chromatography (EtOAc/hexanes 1:2) to give alcohol 20* (29 mg, 0.049 mmol, 30% over two steps) as a clear oil, along with the corresponding 1-isomer (22 mg, 0.037 mmol, 22%). HRMS (ESI) calcd. for $C_{34}H_{42}O_7S$ (M+Na)$^+$ 617.2544. found 617.2542 m/z.

Example 19

6,6'-Dithiobis[α-D-galactopyranosyluronate-(1→1)-1-hexanol] (22*)

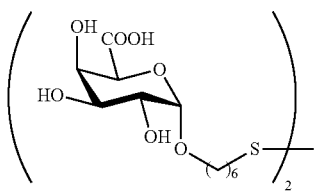

To a stirred solution of ester 20* (10 mg, 0.017 mmol) in THF (1.0 ml) and MeOH (0.5 ml) was added at 0° C. a 1 M solution of NaOH in water (0.8 ml). The reaction was slowly warmed to room temperature and stirred for 16 h. The reaction was diluted with EtOAc (5 ml) and water (5 ml) and acidified to pH 4 with 0.5 M aq. NaHSO$_4$. After separation, the aqueous fraction was extracted with EtOAc (8×5 ml), the combined organic fractions were dried over Na$_2$SO$_4$ and concentrated to give the intermediate acid as a white solid.

To a stirred solution of liquid ammonia (8 ml) was added at −78° C. a solution of the crude diacid in THF (2 ml). The mixture was treated with tBuOH (0.4 ml) and lumps of freshly cut sodium (45 mg) were added until a deeply blue color persisted. The reaction was stirred at −78° C. for 45 min and quenched by addition of solid ammonium acetate (100 mg). The solution was warmed to room temperature under a stream of argon and co-evaporated with MeOH (2×10 ml) and water (2×5 ml). The residue was left under air for 16 h, purified by size exclusion chromatography (Sephadex G-25, 9:1 MeOH/5 mM aq. NH$_4$OAc) and lyophilized repeatedly to give disulfide 22* (3.1 mg, 5.1 μmol, 60% over two steps) as a white solid. HRMS (MALDI) calcd for C$_{24}$H$_{42}$O$_{14}$S$_2$ (M-H$^+$) 617.1938. found 617.1954 m/z.

Example 20

2-Acetamido-4-(benzyloxycarbonyl)amino-3-O-levulinoyl-2,4,6-trideoxy-α-D-galactopyranosyl-(1→1)-6-(benzylthio)hexanol (23*)

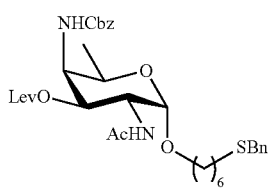

6-(Benzylthio)hexanol 21* (29 mg, 0.171 mmol) and glycosyl phosphate 2* (70 mg, 0.114 mmol) were co-evaporated with dry toluene (3×10 ml) and kept under high vacuum for 30 min. The mixture was dissolved in CH$_2$Cl$_2$ (1.8 ml) and stirred over activated molecular sieves (4 Å-AW) for 1 h at room temperature. The solution was then cooled to 0° C. and treated with TMSOTf (31 μl, 0.171 mmol in 0.2 ml dry CH$_2$Cl$_2$). The mixture was stirred for 3 h at that temperature, quenched with a 1:1 (v/v) mixture of MeOH and triethylamine (0.5 ml), diluted with CH$_2$Cl$_2$ (20 ml) and filtered through Celite. The residue was purified by flash chromatography (EtOAc/hexanes 2:3 to 3:2) to give the corresponding glycosides (57 mg) as an inseparable α/β mixture.

To a stirred solution of the glycoside mixture in dry pyridine (0.9 ml) was added at 0° C. thioacetic acid (0.9 ml). The mixture was warmed to room temperature and stirred for 24 h at that temperature. The solution was co-evaporated with toluene (2×5 ml) and the residue was purified by flash chromatography (EtOAc/hexanes 1:2 to 2:1 to 6:1) to give acetamide 23* (22 mg, 0.034 mmol, 29% over two steps) as a white solid, along with the corresponding β-isomer (21.6 mg, 0.034 mmol, 29%). HRMS (ESI) calcd for C$_{34}$H$_{46}$N$_2$O$_8$S (M+Na)$^+$ 665.2872. found 665.2865 m/z.

Example 21

6,6'-Dithiobis[2-acetamido-4-amino-2,4,6-trideoxy-α-D-galactopyranosyl-(1→1)-1-hexanol] (24*)

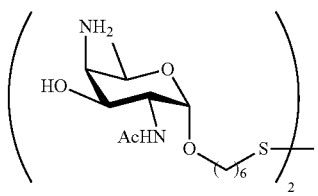

To a stirred solution of ester 23* (10 mg, 0.016 mmol) in dry CH$_2$Cl$_2$ (1.0 ml) were added at room temperature first a mixture of pyridine (38 μl, 0.467 mmol) and acetic acid (24.9 μl, 0.436 mmol), and then hydrazine hydrate (1.0 μl, 0.020 mmol). The mixture was stirred for 2 h at that temperature, quenched with acetone (0.1 ml) and purified by size exclusion chromatography (Sephadex LH-20, CH$_2$Cl$_2$/MeOH 2:1) to give the corresponding alcohol as a clear oil.

To a stirred solution of liquid ammonia (5 ml) was added at −78° C. a solution of the intermediate alcohol in THF (1.2 ml). The mixture was treated with tBuOH (0.5 ml) and lumps of freshly cut sodium (80 mg) were added until a deeply blue color persisted. The reaction was stirred at −78° C. for 45 min and quenched by addition of solid ammonium acetate (100 mg). The solution was warmed to room temperature under a stream of argon and co-evaporated with MeOH (2×10 ml) and water (2×5 ml). The residue was left under air for 16 h, purified by size exclusion chromatography (Sephadex G-25, 9:1 MeOH/5 mM aq. NH$_4$OAc) and lyophilized repeatedly to give disulfide 24* (1.7 mg, 2.7 μmol, 33% over two steps) as a white solid. HRMS (ESI) calcd. for C$_{28}$H$_{54}$N$_4$O$_8$S$_2$(M+Na)$^+$ 661.3281. found 661.3306 m/z.

Example 22

2-Acetamido-4-(benzyloxycarbonyl)amino-3-O-levulinoyl-2,4,6-trideoxy-α-D-galactopyranosyl-(1→1)-2-(benzylthio)ethanol (25*)

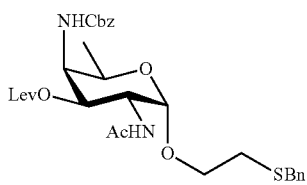

2-(benzylthio)ethanol 11* (71 mg, 0.421 mmol) and glycosyl phosphate 2* (171 mg, 0.281 mmol) were co-evaporated with dry toluene (3×10 ml) and kept under high vacuum for 30 min. The mixture was dissolved in $CH_2Cl_2$ (1.8 ml) and stirred over activated molecular sieves (4 Å-AW) for 1 h at room temperature. The solution was then cooled to −40° C. and treated with TMSOTf (56 μl, 0.309 mmol in 0.2 ml dry $CH_2Cl_2$). The mixture was slowly warmed to 0° C. (2 h), quenched with a 1:1 (v/v) mixture of MeOH and triethylamine (0.5 ml), diluted with $CH_2Cl_2$ (20 ml), filtered through Celite and concentrated. The residue was purified by flash chromatography (EtOAc/hexanes 1:3 to 1:1) to give the corresponding α-glycoside (55 mg, 0.096 mmol, 34%) along with the corresponding β-glycoside (22 mg, 0.039 mmol, 14%). To a stirred solution of the intermediate α-glycoside (40 mg, 0.070 mmol) in dry pyridine (0.4 ml) was added at 0° C. thioacetic acid (0.4 ml). The mixture was warmed to room temperature and stirred for 24 h at that temperature. The solution was co-evaporated with toluene (2×5 ml) and the residue was purified by flash chromatography (EtOAc/hexanes 1:3 to acetone/hexanes 1:2 to 2:3) to give acetamide 25* (31 mg, 0.053 mmol, 76%) as a white solid. HRMS (ESI) calcd for $C_{30}H_{38}N_2O_8S$ $(M+Na)^+$ 609.2246. found 609.2256 m/z.

Example 23

6,6'-Dithiobis[2-acetamido-4-amino-2,4,6-trideoxy-α-D-galactopyranosyl-(1→1)-1-ethanol] (26*)

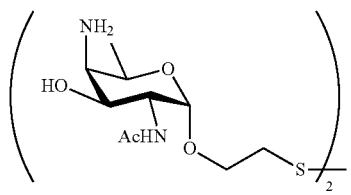

To a stirred solution of ester 25* (20.7 mg, 0.035 mmol) in dry $CH_2Cl_2$ (3.0 ml) were added at room temperature first a mixture of pyridine (86 μl, 1.058 mmol) and acetic acid (57 μl, 0.988 mmol), and then hydrazine hydrate (3.4 μl, 0.071 mmol). The mixture was stirred for 5 h at that temperature, diluted with EtOAc (2 ml), quenched with acetone (0.1 ml) and poured into water (10 ml). The aqueous phase was extracted with EtOAc (4×5 ml), the combined organic fractions were dried over $Na_2SO_4$ and concentrated. The residue was purified by flash chromatography (acetone/hexanes 1:1) to give the intermediate alcohol (17.5 mg) as a white solid.

To a stirred solution of liquid ammonia (6 ml) was added at −78° C. a solution of the intermediate alcohol in THF (1.5 ml). The mixture was treated with tBuOH (0.5 ml) and lumps of freshly cut sodium (45 mg) were added until a deeply blue color persisted. The reaction was stirred at −78° C. for 45 min and quenched by addition of solid ammonium acetate (100 mg). The solution was warmed to room temperature under a stream of argon and co-evaporated with MeOH (2×10 ml) and water (2×5 ml). The residue was left under air for 16 h, purified by size exclusion chromatography (Sephadex G-25, 1:10 MeOH/5 mM aq. $NH_4OAc$) and lyophilized repeatedly to give disulfide 26* as the diacetate salt (7.91 mg, 12.3 μmol, 70% over two steps) as a white solid. HRMS (ESI) calcd. for $C_{20}H_{38}N_4O_8S_2(M+Na)^+$ 549.2029. found 549.2086 m/z.

Example 24

2,2'-Dithiobis[α-D-galactopyranosyluronate-(1→3)-α-D-galactopyranosyluronate-(1→1)-1-ethanol] (27*)

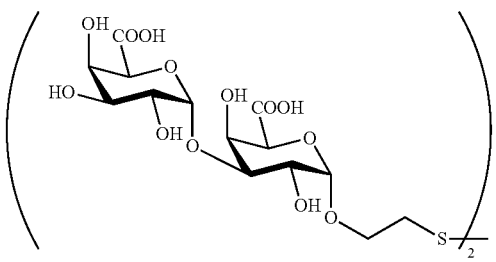

To a stirred solution of ester 13* (8.6 mg, 9.5 μmol) in THF (0.6 ml) and MeOH (0.3 ml) was added at 0° C. a 1 M solution of NaOH in water (0.5 ml). The reaction was slowly warmed to room temperature and stirred for 16 h. The reaction was diluted with EtOAc (5 ml) and water (5 ml) and acidified to pH 4 with 0.5 M aq. $NaHSO_4$. After separation, the aqueous fraction was extracted with EtOAc (8×5 ml), the combined organic fractions were dried over $Na_2SO_4$ and concentrated to give the intermediate diacid as a white solid.

To a stirred solution of liquid ammonia (6 ml) was added at −78° C. a solution of the crude diacid in THF (1.5 ml). The mixture was treated with tBuOH (0.4 ml) and lumps of freshly cut sodium (75 mg) were added until a deeply blue color persisted. The reaction was stirred at −78° C. for 45 min and quenched by addition of solid ammonium acetate (100 mg). The solution was warmed to room temperature under a stream of argon and co-evaporated with MeOH (2×10 ml) and water (2×5 ml). The residue was left under air for 16 h, purified by size exclusion chromatography (Sephadex G-25, 1:9 MeOH/5 mM aq. $NH_4OAc$) and lyophilized repeatedly to give disulfide 27* (2.5 mg, 2.9 μmol, 61% over two steps) as a white solid. HRMS (MALDI) calcd for $C_{28}H_{42}O_{26}S_2(M-H^+)$ 901.0966. found 901.0981 m/z.

Example 25

Synthesis of Glycoconjugates—Conjugation of Saccharides of General Formula (I) to $CRM_{197}$ To a stirred solution of $CRM_{197}$ (1 mg, 17.2 nmol) in 0.1 M sodium phosphate buffer (NaPi) pH 7.4 (1 ml) was added at room temperature a solution of succinimidyl-3-(bromoacetamido)propionate (SBAP) (264 μg, 863 nmol) in DMF (20 μl). The mixture was stirred for 1 h at that temperature, and concentrated using membrane filtration (Amicon Ultra centrifuge membranes, 10 kDa cut-off). The protein solution was diluted with 0.1 M NaPi pH 7.4 and concentrated again. This process was repeated three times and the solution was diluted to 1 ml using 0.1 M NaPi pH 7.4. The intermediate of general formula (II) (690 mmol) in 120 μl0.1 M NaPi pH 7.4 was treated at room temperature with tris(2-carboxyethyl)phosphine (TCEP) (690 mmol), left for 1 h at that temperature under an argon atmosphere and added to the solution of the bromoacetamido-modified $CRM_{197}$ protein at room temperature. The mixture was left at room temperature for 2 h and then at 4° C. for 16 h, and purified using membrane filtration (see above). The purified glycoconjugate in 0.1 M NaPi pH 7.4 (1 ml) was then treated at room temperature with L-cysteine (417 µg, 3.45 µmol) in 100 µl water. The mixture was left for 2 h at that temperature and purified by membrane filtration. Incorporation of the saccharide of general formula (I) into the glycoconjugate was assessed by MALDI-TOF-MS, SDS-PAGE and size exclusion chromatography with right angle light scattering detection (SEC-RALS).

Example 26

Synthesis of Glycoconiugates—in Flow Conjugation of the Saccharides of General Formula (I) to a Glycosphingolipid with Immunomodulatory Properties By using a photochemical flow reactor (*Chem. Eur. J.* 2013, 19, 3090) that was fitted with a loop of Teflon AF2400 tubing (566 µL), a solution of saccharide of general formula (I) (1.5 equiv.) in water (300 µL) was reacted with pentenyl modified (2S,3S,4R)-1-(α-D-galactopyranosyl)-2-hexacosanoylaminooctadecane-3,4-diol (1 equiv.) in water (300 µL) and AcOH (8 µL; residence time: 10 min, flow rate: 28.3 µL/min$^{-1}$ per syringe). The reactor output was lyophilized and the crude material was purified using size exclusion chromatography (Sephadex-G25, 5% EtOH in water, 10 mm×150 mm) to yield the glycoconjugate of saccharide of general formula (I) covalently linked to the modified (2S, 3S,4R)-1-(α-D-galactopyranosyl)-2-hexacosanoylaminooctadecane-3,4-diol as white solid.

Example 27

Synthesis of glycoconiugates—Conjugation of 2-acetamido-4-amino-2,4,6-trideoxy-α-D-galactopyranosyl-(1→4)-(α-D-galactopyranosyl)uronate-(1→3)-(α-D-galactopyranosyl)uronate-(1→1)-2-(thio) ethanol to BSA To a stirred solution of BSA (0.5 mg, 7.6 nmol) in 0.1 M sodium phosphate buffer (NaPi) pH 7.4 (1 mL) was added at room temperature a solution of N-succinimidyl-3-(bromoacetamido)propionate (SBAP) (89 µg, 290 nmol) in DMF (20 µL). The mixture was stirred for 1 h at room temperature, and concentrated using membrane filtration (Amicon 0.5 mL Ultra centrifuge membranes, 10 kDa cut-off). The protein solution was diluted with 0.1 M NaPi pH 7.4 and concentrated again. This process was repeated three times and the solution was diluted to 0.5 mL using water. 20 µL were taken for analysis, and the protein solution was re-buffered to 0.1 M NaPi pH 7.4 using membrane filtration. Disulfide 18* (140 µg, 228 nmol resp. to the monomer) in 120 µL 0.1 M NaPi pH 7.4 was treated at room temperature with tris(2-carboxyethyl)phosphine (TCEP) (250 nmol), left for 1 h at that temperature under an argon atmosphere and added to the solution of the activated protein at room temperature. The mixture was left at 4° C. for 16 h, and purified using membrane filtration (see above). After washing with water and diluting to 0.5 mL, another analytical sample (20 µL) was taken, and the solution was re-buffered. The purified glycoconjugate in 0.1 M NaPi pH 7.4 (0.5 mL) was then treated at room temperature with L-cysteine (417 µg, 3.45 µmol) in 100 µl water. The mixture was left for 2 h at that temperature and purified by membrane filtration. Incorporation of 2-acetamido-4-amino-2,4,6-trideoxy-α-D-galactopyranosyl-(1→4)-(α-D-galactopyranosyl)uronate-(1→3)-(α-D-galactopyranosyl)uronate-(1→1)-2-(thio)ethanol into the glycoconjugate was assessed by MALDI-TOF-MS (positive mode):

Molecular Weight Measured:
BSA: 66341 m/z.
BSA-SBAP conjugate: 68316 m/z (incorporation of approximately 10 SBAP groups).
BSA-SBAP glycoconjugate: 69101 m/z (incorporation of approximately 1.3 molecules of 2-acetamido-4-amino-2,4,6-trideoxy-α-D-galactopyranosyl-(1→4)-(α-D-galactopyranosyl)uronate-(1→3)-(α-D-galactopyranosyl)uronate-(1→1)-2-(thio)ethanol).
BSA-SBAP glycoconjugate after quenching with L-cysteine: 72074 m/z (incorporation of approximatively 24.5 L-cysteine molecules).

Example 28

Synthesis of glycoconiugates—Conjugation of 2-acetamido-4-amino-2,4,6-trideoxy-α-D-galactopyranosyl-(1→4)-(α-D-galactopyranosyl)uronate-(1→3)-(α-D-galactopyranosyl)uronate-(1→1)-2-(thio) ethanol to BSA To a stirred solution of BSA (0.5 mg, 7.6 nmol) in 0.1 M sodium phosphate buffer (NaPi) pH 7.4 (1 mL), a solution of N-Succinimidyl-3-maleimidopropionate (101 µg, 380 nmol) in DMF (20 µL) was added at room temperature. The mixture was stirred for 1 h at room temperature, and concentrated using membrane filtration (Amicon 0.5 mL Ultra centrifuge membranes, 10 kDa cut-off). The protein solution was diluted with 0.1 M NaPi pH 7.4 and concentrated again. This process was repeated three times and the solution was diluted to 0.5 mL using water. 20 µL were taken for analysis, and the protein solution was re-buffered to 0.1 M NaPi pH 7.4 using membrane filtration. Disulfide 18* (140 µg, 228 nmol resp. to the monomer) in 120 µl 0.1 M NaPi pH 7.4 was treated at room temperature with tris(2-carboxyethyl)phosphine (TCEP) (250 nmol), left for 1 h at that temperature under an argon atmosphere and added to the solution of the activated protein at room temperature. The mixture was left at 4° C. for 16 h, and purified using membrane filtration (see above). After washing with water and diluting to 0.5 mL, another analytical sample (20 µL) was taken, and the solution was re-buffered. The purified glycoconjugate in 0.1 M NaPi pH 7.4 (0.5 mL) was then treated at room temperature with L-cysteine (417 µg, 3.45 µmol) in 100 µl water. The mixture was left for 2 h at that temperature and purified by membrane filtration. Incorporation of glycan into the glycoconjugate was assessed by MALDI-TOF-MS (positive mode):

Molecular Weight Measured:
BSA: 66341 m/z;
BSA-maleimide conjugate: 69254 m/z (incorporation of approximately 19 maleimide groups);
BSA-maleimide glycoconjugate: 71340 m/z (incorporation of approximately 3.4 molecules of 2-acetamido-4-amino-2,4,6-trideoxy-α-D-galactopyranosyl-(1→4)-(α-D-galactopyranosyl)uronate-(1→3)-(α-D-galactopyranosyl) uronate-(1→1)-2-(thio)ethanol);
BSA-maleimide glycoconjugate after quenching with L-cysteine: 72106 m/z (incorporation of approx. 6.3 L-cysteine molecules).

Example 29

Conjugation to a Solid Support—Synthesis of Microarrays Using GAPSII Slides Maleimide-functionalized microarrays were produced by submerging amine-coated slides (GAPS II slides, Corning) in 6-maleimidohexanoic acid N-hydroxysuccinimide ester (2 mM) in dry DMF with diisopropylethylamine (2.5% v/v) for 24 h at room temperature. Slides were washed three times with water and three times with ethanol, centrifuged to dryness, and stored under argon until spotting. Diluted saccharides of general formula (I) were printed onto the modified microarray slides at 0.4 nL per spot by an automatic piezoelectric arraying robot (Scienion, Berlin, Germany). For completion of the immobilization reaction, printed slides were stored for 24 h in a humidified chamber.

Microarray slides were washed three times with water. Unreacted maleimide was quenched by submerging the slides in β-mercaptoethanol (0.1%, v/v) in PBS for 1 h at room temperature. Slides were washed three times with water and with ethanol, centrifuged to dryness, and blocked with BSA (1%, w/v) in PBS for 1 h at room temperature. Blocked slides were washed (2×PBS, 3×water), centrifuged, and incubated with the sera dilutions.

Example 30

Conjugation to a Solid Support—Synthesis of Microarrays Using CodeLink NHS Slides CodeLink NHS slides were incubated for 24 h (1% w/v in PBS) at 4° C. Slides were incubated in blocking buffer (100 mM ethanolamine in 50 mM NaPi pH>9) for 30 min at room temperature, washed three times each with water and ethanol, and dried. Slides were then subjected to maleimide functionalization and printing (see Example 29).

Example 31

Binding Experiments Using the Microarrays Synthesized According to the Procedure Described at Examples 29 and 30

Binding experiments were performed by incubating microarray slides coated with the saccharides of general formula (I) with either a rabbit anti-SP1 typing serum or human pneumococcal reference serum 007sp (pooled sera of 287 humans immunized with Pneumovax vaccine) in the dilutions indicated in the presence or absence of native SP1 polysaccharide, and using fluorescently labeled anti-rabbit or anti-human secondary antibodies.

Example 32

Assessment of the Immunogenicity of the Linker A and of the Interconnecting Molecule To check the immunogenicity of the linker A and of the interconnecting molecule used in preparing the glycoconjugate 1 according to the present invention i.e. a glycoconjugate containing
a saccharide of general formula I presenting a linker A connected via an interconnecting molecule 1 to immunogenic carrier 1 such as:

H—$(P)_{n3}$—$(N)_{n2}$-$(M)_{n3}$-O-A-S-rest interconnecting molecule 1-immunogenic carrier 1, three glycoconjugates need to be synthesized:

Glycoconjugate 2:
H—$(P)_{n3}$—$(N)_{n2}$-$(M)_{n3}$-O-A-S-rest interconnecting molecule 2-immunogenic carrier 2;

Glycoconjugate 3:
galactose-O-A-S-rest interconnecting molecule 1-immunogenic carrier 2;

Glycoconjugate 4:
galactose-O-A-S-rest interconnecting molecule 2-immunogenic carrier 2;

The immunogenic carrier 2 has to be non-related to immunogenic carrier 1 used in immunization. For example, if CRM197 was used to prepare glycoconjugate 1, then BSA can be used as immunogenic carrier 2.

The galactose was chosen for preparing glycoconjugate 3, as it is non related to the saccharides according to the present invention i.e. to H—$(P)_{n3}$—$(N)_{n2}$-$(M)_{n3}$-OH.

The interconnecting molecule 2 used for the preparation of glycoconjugate 2 has to be non related to interconnecting molecule 1. For example, if Sulfo-GMBS was used as interconnecting molecule 1, then a non-related interconnecting molecule 2 would be Sulfo SIAB.

The choice of immunogenic carrier 2, interconnecting molecule 2 and of non related saccharide are obvious for the person skilled in the art of synthesis of glycoconjugates.

Protocol for ELISA:

A 96-well-plate is coated with 50 µl of the respective glycoconjugates (50 µg/ml) in PBS for 1 h at 37° C. The plate is washed once with 100 µl washing buffer (PBS+0.1% (v/v) Tween-20) and blocked using 200 µl blocking solution (1% (w/v) BSA in PBS) for 1 h at 37° C. The plate is washed 3× with washing buffer and then incubated with dilutions of antiserum in blocking solution (50 µl) for 16 h at 4° C. The plate is washed 3× and incubated with 50 µl of an appropriate secondary antibody (e.g. Goat Anti-Mouse IgG H&L (HRP), abcam ab6789) diluted in blocking solution for 1 h at 37° C. The plate is washed 3× with washing buffer and incubated with ELISA substrate (e.g. ABTS from Pierce, No. 37615) according to the manufacturer's manual.

Comparison of the optical density between the glycoconjugates applied will give a quantitative comparison between anti-linker-, anti-interconnecting molecule, and anti-saccharide immune responses.

Example 33

2-Azido-4-(benzyloxycarbonyl)amino-2,4,6-trideoxy-α-D-galactopyranosyl-(1→1)-6-(benzylthio) ethanol (28*)

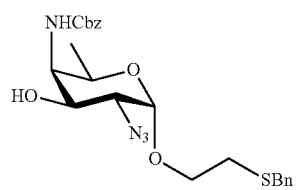

To a stirred solution of the intermediate Lev ester 25* (17 mg, 0.03 mmol) in dry CH$_2$Cl$_2$ (1 mL) were added at room temperature first a mixture of pyridine (72 µl, 0.894 mmol) and acetic acid (48 µl, 0.834 mmol), and then hydrazine hydrate (3 µl, 0.062 mmol). The mixture was stirred for 5 h at that temperature, diluted with EtOAc (2 ml), quenched with acetone (0.1 mL) and poured into water (10 mL). The aqueous phase was extracted with CH$_2$Cl$_2$ (4×5 ml), the combined organic fractions were dried over Na$_2$SO$_4$ and concentrated. The residue was purified by flash chromatography (EtOAc/hexanes 3:1) to give alcohol 28* (13 mg, 0.028 mmol, 92%) as a clear oil. HRMS (ESI) calcd. for C$_{23}$H$_{28}$N$_4$O$_5$S (M+Na)$^+$ 495.1678. found 495.1679 m/z.

Example 34

Methyl (2,3-di-O-benzyl-α-D-galactopyranosyl)uronate-(1→3)-2-azido-4-(benzyloxycarbonyl)amino-2,4,6-trideoxy-α-D-galactopyranosyl-(1→1)-2-(benzylthio)ethanol (29*)

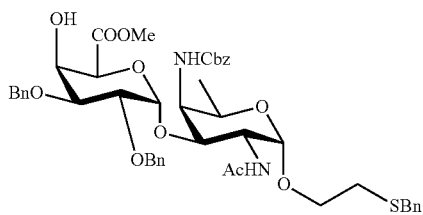

Alcohol 28*(13 mg, 0.028 mmol), TTBPy (45, 0.138 mmol) and thioglycoside 19* (37 mg, 0.069 mmol) were co-evaporated with dry toluene (3×10 mL) and kept under high vacuum for 1 h. The mixture was dissolved in dry THF (1.5 mL) and stirred over activated molecular sieves (3 Å) for 30 min at room temperature. The solution was cooled to 0° C. and treated dropwise with DMTST (17 mg, 0.069 mmol in 0.2 mL DCM) The mixture was warmed to room temperature and treated with an additional DMTST solution in DCM (2 equiv.) after 2 h. The reaction was stirred for 16 h and quenched with 1:1 (v/v) mixture of 10% aq. Na$_2$S$_2$O$_3$ and sat. aq. NaHCO$_3$ (5 mL). The mixture was extracted with CH$_2$Cl$_2$ (3×10 mL), dried over Na$_2$SO$_4$ and concentrated. The residue was purified by flash chromatography (EtOAc/hexanes 1:2) to give the intermediate disaccharide as a clear oil.

To a stirred solution of the intermediate disaccharide in dry pyridine (0.2 ml) was added at 0° C. thioacetic acid (0.2 ml). The mixture was warmed to room temperature and stirred for 24 h at that temperature. The solution was co-evaporated with toluene (2×5 ml) and the residue was purified by flash chromatography (EtOAc/hexanes 1:3 to acetone/hexanes 1:2) to give the intermediate acetamide as a white foam.

To a stirred solution of the intermediate acetamide in dry CH$_2$Cl$_2$ (0.6 mL) and MeOH (60 µL) were added at room temperature first a mixture of pyridine (12 µl, 0.16 mmol) and acetic acid (8 µl, 0.15 mmol), and then hydrazine hydrate (1 µl, 0.021 mmol). The mixture was stirred for 3 h at that temperature, diluted with CH$_2$Cl$_2$ (2 ml), quenched with acetone (0.1 mL) and poured into water (5 mL). The aqueous phase was extracted with CH$_2$Cl$_2$ (4×5 ml), the combined organic fractions were dried over Na$_2$SO$_4$ and concentrated. The residue was purified by flash chromatography (acetone/hexanes 0:1 to 1:1) to give acetamide 29* (2.7 mg, 3.14 µmol, 21% over 3 steps based on recovered 28*) as a white foam. HRMS (ESI) calcd. for C$_{46}$H$_{54}$N$_2$O$_{12}$S (M+Na)$^+$881.3295. found 881.3286 m/z.

Example 35

2,2'-Dithiobis[α-D-galactopyranosyluronate-(1→3)-2-acetamido-4-amino-2,4,6-trideoxy-α-D-galactopyranosyl-(1→1)-1-ethanol] (30*)

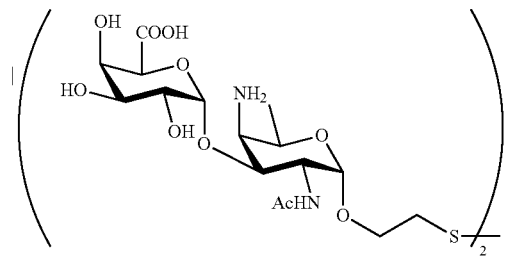

To a stirred solution of ester 29* (2.7 mg, 3.14 µmol) in THF (1 mL) and MeOH (0.25 mL) was added at 0° C. a 1 M solution of NaOH in water (0.4 mL). The reaction was slowly warmed to room temperature and stirred for 16 h. The reaction was diluted with EtOAc (5 ml) and water (5 ml) and acidified to pH 4 with 0.5 M aq. NaHSO$_4$. After separation, the aqueous fraction was extracted with EtOAc (8×5 ml), the combined organic fractions were dried over Na$_2$SO$_4$ and concentrated to give the intermediate diacid as a white solid.

To a stirred solution of liquid ammonia (10 ml) was added at −78° C. a solution of the crude diacid in THF (1.5 ml). The mixture was treated with tBuOH (0.4 ml) and lumps of freshly cut sodium (80 mg) were added until a deeply blue color persisted. The reaction was stirred at −78° C. for 45 min and quenched by addition of solid ammonium acetate (100 mg). The solution was warmed to room temperature under a stream of argon and co-evaporated with MeOH (2×10 ml) and water (2×5 ml). The residue was left under air for 16 h, purified by size exclusion chromatography (Sephadex G-25, 1:3 MeOH/5 mM aq. NH$_4$OAc) and lyophilized repeatedly to give disulfide 30* (1.15 mg, 2.61 µmol, 83% over two steps) as a white solid:

$^1$H NMR (600 MHz, D$_2$O) δ 5.16 (d, J=2.0 Hz, 1H), 5.02 (d, J=3.2 Hz, 1H), 4.49 (d, J=5.9 Hz, 1H), 4.44-4.35 (m, 1H), 4.34-4.20 (m, 2H), 4.15-4.04 (m, 1H), 4.00-3.78 (m, 5H), 3.06 (t, J=5.6 Hz, 2H), 2.09 (s, 3H), 1.41 (d, J=6.6 Hz, 3H). LRMS calcd. for C$_{32}$H$_{54}$N$_4$O$_{20}$S$_2$(M+2H)$^{2+}$ 440.4. found 440.2 m/z.

Example 36

General Procedures for Accessing the Compound of General Formula 3 According to the Present Invention

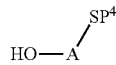

Example 36.1

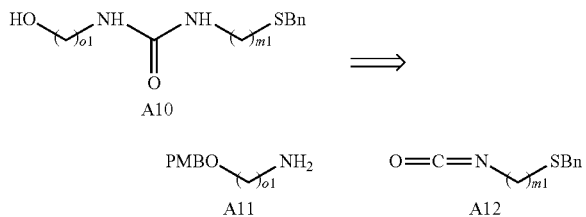

To a solution of isocyanate A12 (2.70 mmol) in 12 ml of CH$_2$Cl$_2$ was added the amine (1.05 eq, 2.83 mmol). The reaction mixture was stirred at ambient temperature for 12 hours and then concentrated in vacuo. The crude material was dissolved in Et$_2$O followed by addition of hexane. The urea was then precipitated and filtered to get product.

A mixture of p-methoxybenzyl ether protected urea compound (0.4 mmol) and 1,3,5-trimethoxybenzene (0.2 mmol) in anhydrous CH$_2$Cl$_2$ (3 mL) was added via a cannula to a solution of silver hexafluoroantimonate (20 µmol, 5 mol %) in anhydrous CH$_2$Cl$_2$ (1 mL). The reaction mixture was heated to reflux until completion and filtered through a small pad of Celite with dichloromethane as eluent. Solvents were removed in vacuum, and the crude residue was purified by flash chromatography to get A10.

Example 36.2

To a mixture of aldehyde A17 (1.0 mmol) and ketone A16 (1.0 mmol) in i-PrOH (100 iL) were added propionic acid (0.1 mmol, 10 mol %) and pyrrolidine (0.1 mmol, 10 mol %). The reaction mixture was stirred at 45° C. for 1-25 h. NaHCO$_3$ was added, and the mixture was extracted with CH$_2$Cl$_2$ (3 5 mL). The combined extracts were washed with brine, dried (Na$_2$SO$_4$), and concentrated in vacuo. The residue was purified by flash chromatography to give intermediate unsaturated ketone A15.

A 9.5×10$^{-3}$ M solution of intermediate unsaturated ketone A15 (0.05 mmol) in THF and recently prepared Stryker's reagent (0.025 mmol), were mixed together forming a homogeneous solution that was stirred at room temperature for 2 h. The reaction was quenched with saturated aq. NH$_4$Cl. The mixture was stirred for 1 h. The reaction mixture was filtered, and the residue was washed with ethyl acetate. The organic phase was separated, and the aqueous phase was extracted with ethyl acetate. The combined organic phases were dried with MgSO$_4$ and the solvent was removed under vacuum. The residue was purified by column chromatography on silica gel to give ketone A14.

Neat tris-nonyloxy methyl titanium (10.1 mmol) was placed in a two-necked round bottom flask and subjected to Ar atmosphere. Ketone A14 (4.65 mmol) in THF was added and the mixture was stirred at room temperature for 30 min. Oleic acid (17.8 mmol) was added and the mixture was heated to 110° C. The product was concentrated and purified by flash chromatography to give the intermediate tertiary alcohol.

To a solution of the PMB ether (0.1 mmol) in dichloroethane (5 mL), POCl$_3$ (0.5 mmol) was added and stirred at room temperature. After completion of the reaction, it was quenched in ice water and the organic layer was separated and the aqueous layer was extracted with dichloroethane (2×5 mL). Combined organic layer was washed with brine solution, dried (Na$_2$SO$_4$), concentrated under reduced pressure and the residue was purified by column chromatography (silica gel, EtOAc:Hexanes) to afford alcohol A13.

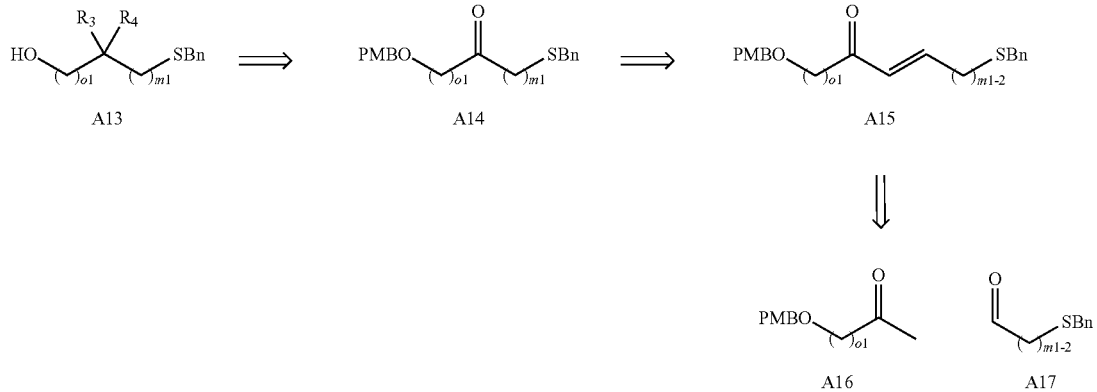

wherein: R$^3$ represents Me and R$^4$ represents OH

Example 36.3

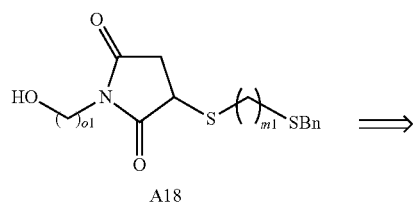

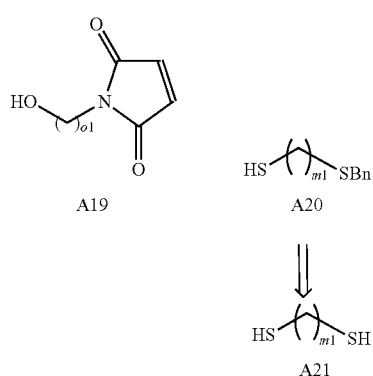

An oven-dried, 250-mL, round-bottomed flask was charged with 1,3-propanedithiol (20 mmol, 1.1 equiv) and tetrabutylammonium iodide (0.40 mmol, 2.2 mol %) in dry THF (100 mL). The mixture was stirred at room temperature and sodium hydride (60% suspension in mineral oil, 20 mmol, 1.1 equiv) was added by portions. The resulting mixture was stirred for 30 min, then benzyl bromide (18 mmol) was added dropwise. The solution was stirred for 1 h at room temperature, then filtered on a frit funnel and concentrated under vacuum. The resulting crude oil was distilled under vacuum to afford the title compound as colorless oil A20.

To a solution of A19 (0.11 mmol) in anhydrous DMF (2 mL) was added thiol A20 (0.22 mmol). The mixture was stirred at 25° C. for 18 h and then concentrated in vacuum. The residue was purified by flash chromatography to afford A18.

A variety of dithiol derivatives of general formula A20 are commercially available.

Example 36.4

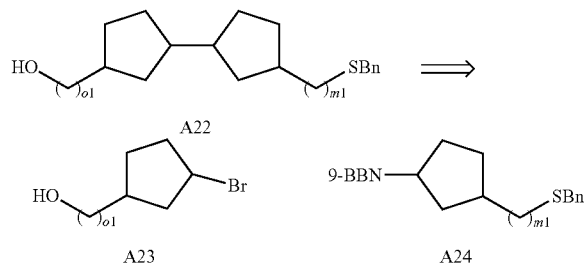

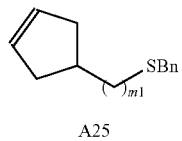

Freshly cut sodium metal (4.67 mmol) was dissolved in isopropanol (10 mL) and benzyl mercaptan (6.23 mmol) was added. A solution of 4-(bromomethyl)cyclopent-1-ene (1.55 mmol) in isopropanol (5 mL) was added and the solution was heated under reflux for 4 days. The solution was allowed to cool to room temperature, diluted with water (50 mL) and extracted with diethyl ether (3×50 mL). The combined organic extracts were washed with 0.1 M aq potassium hydroxide (2×50 mL), dried and evaporated to yield crude A25. Column chromatography on silica gel eluting with ethyl acetate/hexane afforded the title compound A25.

A dry 50-mL flask equipped with a magnetic stirring bar, a septum inlet, an oil bubbler, and a reflux condenser was flushed with nitrogen. To the flask were added an alkene A25 (5.5 mmol) and dry THF (2.5 mL) and then a solution of 9-BBN (0.5 M solution in THF, 5.5 mmol) at 0° C. The mixture was warmed up slowly to room temperature and then stirred for 4-6 h to give a solution of B-alkyl-9-BBN A24.

To the above borane solution of A24 were added DMF-THF (25 mL), PdCl$_2$(dppf) (0.15 mmol), haloalkene (5 mmol), and powdered K$_3$PO$_4$ (6 mmol). The mixture was stirred for 8 h at 50° C. and then poured into water. The product was extracted with benzene, washed with water four times, and dried over MgSO$_4$. Column chromatography on silica gel eluting with ethyl acetate/hexane afforded the title compound A22.

Example 36.5

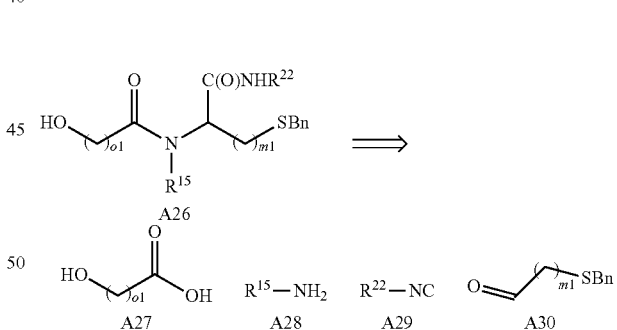

To a solution of 1.1 equiv aldehyde A30 in dry methanol was dropwise added 1.3 equiv of amine A28 in dry methanol at 0° C. under an argon atmosphere. The mixture was stirred for an additional 10 min at room temperature and followed by the sequential addition of 1.0 equiv acid A27 in dry methanol and 1.1 equiv isocyanide A29. The reaction mixture was stirred for 24-48 h at room temperature. The resulting solution was diluted with dichloromethane and washed with 1 N HCl aqueous solution followed by saturated sodium bicarbonate aqueous solution and brine. The organic layer was dried over MgSO4, concentrated and purified by silica gel column chromatography (hexanes/ethyl acetate).

Example 36.6

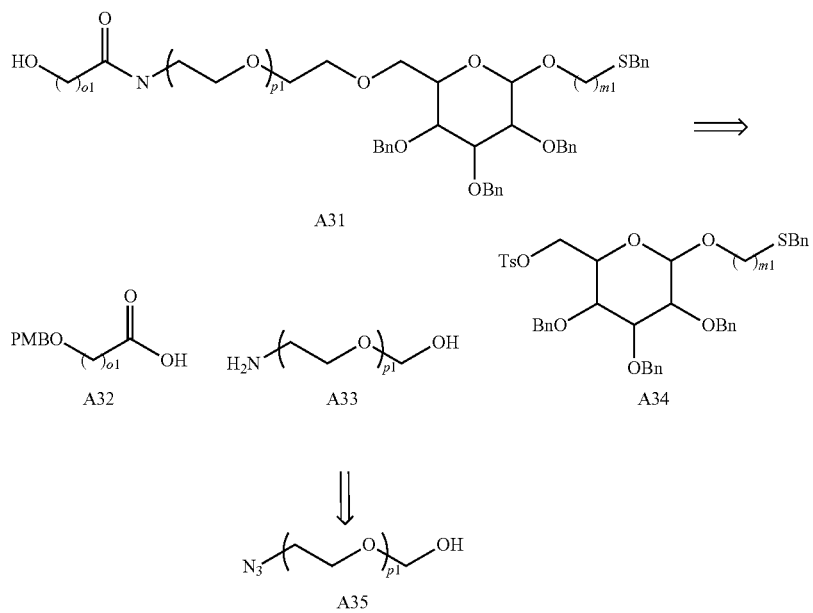

Synthesis of A33:

To the solution of azide A35 (0.03 mol) and ammonium chloride (0.07 mol) in ethyl alcohol (80 mL) and water (27 mL), zinc powder (0.04 mol) was added, the mixture was stirred vigorously at room temperature or at refluxing. After the reaction is over, ethyl acetate (200 mL) and aqueous ammonia (10 mL) was added. The mixture was filtered, and the filtrate was washed with brine, dried over anhydrous sodium sulfate and concentrated under reduced pressure.

Synthesis of A31:

Acid A32 (1 mmol) and amine A33 (1 mmol) were coupled with 1-ethyl-3-(3-dimethylaminopropyl)carbodiimide (EDC) hydrochloride (1 mmol) in 3.5 mL methanol for 3 h at room temperature. The mixture was diluted with EtOAc (20 mL) and extracted with water (10 mL), 1 M aq. HCl (10 mL) and sat. aq. NaHCO$_3$ (10 mL). The organic layer was dried over Na$_2$SO$_4$ and concentrated. The residue was purified by flash chromatography to give the intermediate alcohol.

A suspension of NaH (0.83 mmol) in THF (2 mL) was cooled to 0° C., and then to the suspension was added the intermediate alcohol (0.17 mmol) in THF (4 mL) slowly. The mixture was refluxed for 2 h and then allowed to cool to room temperature. To the mixture was added A34 (0.11 mmol) in THF (2 mL) at that temperature dropwise. The reaction mixture was refluxed for 12 h and then allowed to cool to room temperature. After removal of the solvent by a rotary evaporator, the residue was dissolved in CHCl3 and filtered. The filtrate was evaporated by a rotary evaporator and chromatographed.

To a solution of the PMB ether (0.1 mmol) in dichloroethane (5 mL), POCl$_3$ (0.5 mmol) was added and stirred at room temperature. After completion of the reaction, it was quenched in ice water and the organic layer was separated and the aqueous layer was extracted with dichloroethane (2×5 mL). Combined organic layer was washed with brine solution, dried (Na$_2$SO$_4$), concentrated under reduced pressure and the residue was purified by column chromatography (silica gel, EtOAc:Hexane) to afford the corresponding alcohol A31.

Example 36.7

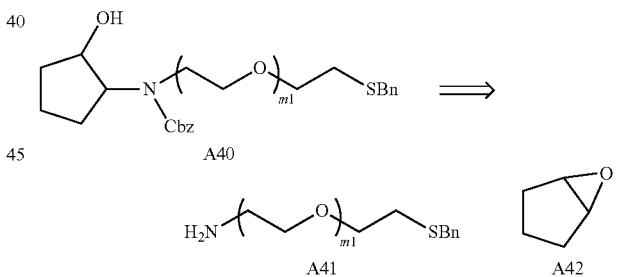

In the test tube were introduced epoxide A42 (5 mmol) and water (2 mL). Amine A41 (6 mmol) was added in one portion and the test tube was kept at 0° C. and warmed to room temperature under vigorous stirring for 24 h. Water (2 ml) was added and the aqueous mixture was extracted with 10 ml of ethyl acetate and dried over anhydrous Na$_2$SO$_4$, and solvent was removed under reduced pressure to give the intermediate β-amino alcohol. The crude amine in EtOAc (2 mL) and sat. aq. NaHCO$_3$ (1 mL) was treated with CbzCl (6 mmol) at room temperature and stirred for 5 h at that temperature. The mixture was extracted with EtOAc (3×5 mL), the organic fraction was dried over Na$_2$SO$_4$ and concentrated. The residue was purified by flash chromatography to give alcohol A40.

Example 36.8

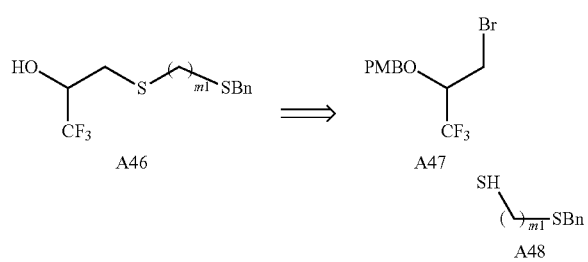

Bromide A47 (8.26 mmol) was reacted with thiol A48 in MeOH (5 mL) adjusted to pH 9 with NaOMe. The mixture was stirred for 16 h at room temperature and concentrated under reduced pressure to give the intermediate PMB ether.

To a solution of the PMB ether (0.1 mmol) in dichloroethane (5 mL), POCl₃ (0.5 mmol) was added and stirred at room temperature. After completion of the reaction, it was quenched in ice water and the organic layer was separated and the aqueous layer was extracted with dichloroethane (2×5 mL). Combined organic layer was washed with brine solution, dried (Na₂SO₄), concentrated under reduced pressure and the residue was purified by column chromatography (silica gel, EtOAc:Hexane) to afford the corresponding alcohol A46.

Example 36.9

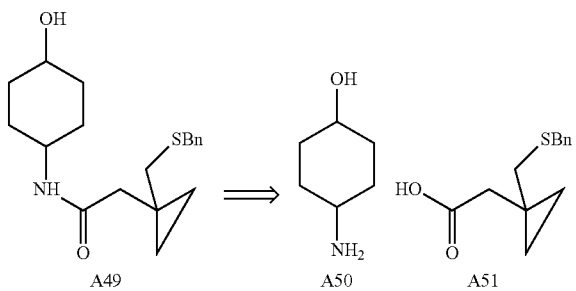

Acid A51 (1 mmol) and amine A50 (1 mmol) were coupled with 1-ethyl-3-(3-dimethylaminopropyl)carbodiimide (EDC) hydrochloride (1 mmol) in 3.5 mL methanol for 3 h at room temperature. The mixture was diluted with EtOAc (20 mL) and extracted with water (10 mL), 1 M aq. HCl (10 mL) and sat. aq. NaHCO₃ (10 mL). The organic layer was dried over Na₂SO₄ and concentrated. The residue was purified by flash chromatography to give alcohol A49.

Example 36.10

To a solution of A53 (80 mmol) in pyridine (60 mL) was added portionwise MsCl (80 mmol) with efficient stirring during 30 min at 20° C. After being stirred for 30 min, the reaction mixture was maintained for 20 h at room temperature, diluted with CH₂Cl₂ (100 mL), and washed with 2 N aq. HCl until the aqueous washings became acidic. The H₂O layer was extracted with CH₂Cl₂ (3×50 mL). The combined organic extract was dried (Na₂SO₄), concentrated, and concentrated to give the intermediate mesylate. Sodium benzylsulfide (4.1 mmol) was added portionwise to a stirred solution of the intermediate mesylate (2.7 mmol) in DMF (5 mL) at room temperature. After 3 h, the mixture was diluted with toluene (100 mL), washed with water (25 mL) and brine (25 mL), dried (MgSO₄), and concentrated in vacuo. The residue was purified by flash chromatography to give thioether A52.

Example 36.11

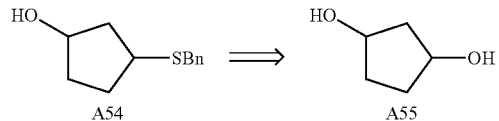

To a solution of the diol A55 (8 mmol) in pyridine (6 mL) was added portionwise TsCl (8 mmol) with efficient stirring during 30 min at 20° C. After being stirred for 30 min, the reaction mixture was maintained for 20 h at room temperature, diluted with CH₂Cl₂ (100 mL), and washed with 2 N aq. HCl until the aqueous washings became acidic. The H₂O layer was extracted with CH₂Cl₂ (3×50 mL). The combined organic extract was dried (Na₂SO₄) and concentrated to give the intermediate tosylate.

A solution of the intermediate tosylate (0.67 mmol) in 5 mL of dry HMPA was cooled in an ice bath under N₂. This mixture was added to a cold solution of NaSBn (10 mmol) in 20 mL of dry HMPA (prepared from 400 mg of sodium and excess BnSH in dry ether, which was subsequently removed and replaced with HMPA). After the addition, the solution was stored in the freezer (−15° C.) for 14 h. It was then treated with 100 mL of water and extracted three times with ether. The ether extracts were washed four times with water and dried over MgSO₄. The solvent was then removed under vacuum and the residue (140 mg) chromatographed over silica gel to give thioether A54.

Example 36.12

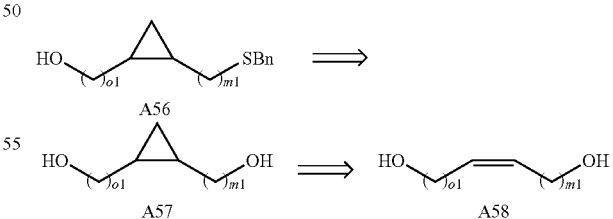

To freshly distilled CH₂Cl₂ (20 mL) was added Et₂Zn (1.0 M in hexanes) (20.0 mmol) under N₂. The solution was cooled in an ice bath and a solution of trifluoroacetic acid (20.0 mmol) in CH₂Cl₂ (10 mL) was then dripped into the reaction mixture via syringe. Upon stirring for 20 min, a solution of CH₂I₂ (20.0 mmol) in CH₂Cl₂ (10 mL) was added. After an additional 20 min of stirring, a solution of diol A58 (10.0 mmol) in CH₂Cl₂ (10 mL) was added, and the ice bath was removed. After an additional 30 min of stirring, the reaction mixture was quenched with 0.1 N HCl (50 mL) (alternatively with saturated aqueous NH$_4$Cl or Et$_3$N followed by saturated aqueous NaHCO$_3$) and hexanes (25 mL), and the layers were separated. The aqueous layer was extracted with hexanes. The combined, organic layers were washed with saturated NaHCO$_3$, H$_2$O, and brine and then dried (Na$_2$SO$_4$), filtered, concentrated, and purified by column chromatography (hexanes/ether=50/1) to give diol A57.

To a solution of the diol A57 (8 mmol) in pyridine (6 mL) was added portionwise TsCl (8 mmol) with efficient stirring during 30 min at 20° C. After being stirred for 30 min, the reaction mixture was maintained for 20 h at room temperature, diluted with CH$_2$Cl$_2$ (100 mL), and washed with 2 N aq. HCl until the aqueous washings became acidic. The H$_2$O layer was extracted with CH$_2$Cl$_2$ (3×50 mL). The combined organic extract was dried (Na$_2$SO$_4$) and concentrated to give the intermediate tosylate.

A solution of the intermediate tosylate (0.67 mmol) in 5 mL of dry HMPA was cooled in an ice bath under N$_2$. This mixture was added to a cold solution of NaSBn (10 mmol) in 20 mL of dry HMPA (prepared from 400 mg of sodium and excess BnSH in dry ether, which was subsequently removed and replaced with HMPA). After the addition, the solution was stored in the freezer (−15° C.) for 14 h. It was then treated with 100 mL of water and extracted three times with ether. The ether extracts were washed four times with water and dried over MgSO$_4$. The solvent was then removed under vacuum and the residue (140 mg) chromatographed over silica gel to give thioether A56.

Example 36.13

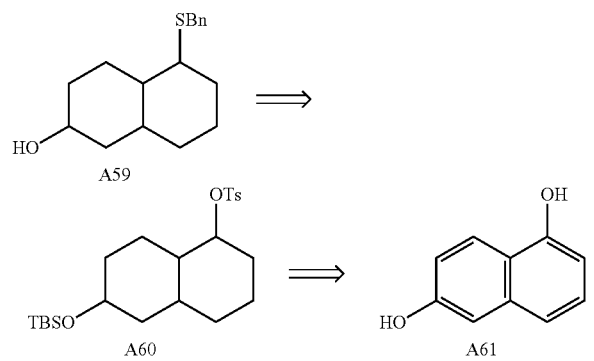

To a solution of diol A61 (16.1 mmol), triethylamine (24.1 mmol), and DMAP (0.16 mmol) in CH$_2$Cl$_2$ (120 mL) was added TBDMSCl (19.3 mmol) in 5 portions over 1 h at 0° C. The resulting heterogeneous reaction mixture was gradually warmed to rt. The mixture was stirred for 12 h before dilution with water and CH$_2$Cl$_2$. The organic layer was washed successively with solutions of saturated aq NaHCO$_3$, saturated aq NH$_4$Cl, water and brine, dried over MgSO$_4$, filtered, and concentrated in vacuo. The pale yellow oil was purified by vacuum chromatography to give the intermediate silyl ether.

A mixture of the intermediate silyl ether (1.0 mmol) and catalyst (Rh or Ru on activated carbon, N.E. Chemcat; 10 wt % of substrate) in iPrOH (1 mL) in a sealed tube was stirred at 60° C. at 5 atm H$_2$. After cooling to room temperature, the reaction mixture was diluted with MeOH (20 mL) and the catalyst was removed by filtration through a membrane filter (Millipore, Millex-LH, 0.45 mm). The filtrate was concentrated in vacuo to give the corresponding decalin.

To a solution of the intermediate decalin alcohol (8 mmol) in pyridine (6 mL) was added portionwise TsCl (8 mmol) with efficient stirring during 30 min at 20° C. After being stirred for 30 min, the reaction mixture was maintained for 20 h at room temperature, diluted with CH$_2$Cl$_2$ (100 mL), and washed with 2 N aq. HCl until the aqueous washings became acidic. The H$_2$O layer was extracted with CH$_2$Cl$_2$ (3×50 mL). The combined organic extract was dried (Na$_2$SO$_4$) and concentrated to give tosylate A60.

A solution of tosylate A60 (0.67 mmol) in 5 mL of dry HMPA was cooled in an ice bath under N$_2$. This mixture was added to a cold solution of NaSBn (10 mmol) in 20 mL of dry HMPA (prepared from 400 mg of sodium and excess BnSH in dry ether, which was subsequently removed and replaced with HMPA). After the addition, the solution was stored in the freezer (−15° C.) for 14 h. It was then treated with 100 mL of water and extracted three times with ether. The ether extracts were washed four times with water and dried over MgSO$_4$. The solvent was then removed under vacuum and the residue (140 mg) chromatographed over silica gel to give the intermediate silyl ether.

The intermediate silyl ether (0.235 mmol) was dissolved in THF (1 mL) at room temperature, followed by addition of 70% HF.pyridine (0.2 mL). After stirring for two days, the reaction mixture was carefully quenched with sat. aq. NaHCO$_3$ and the resulting solution was diluted with EtOAc. The organic layer was washed with brine, dried over Na$_2$SO$_4$, filtered and concentrated in vacuo. The residue was purified by silica gel column chromatography to give alcohol A59.

Example 36.14

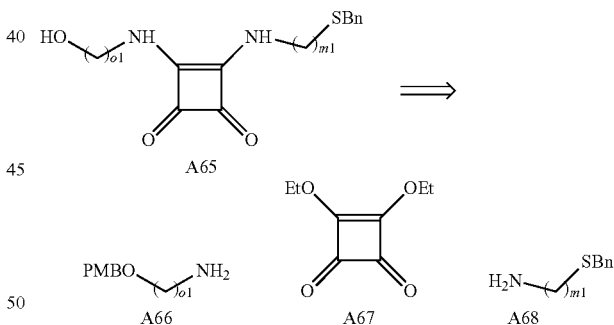

A solution of squaric ethyl ester A67 (0.5 mmol), A68 (100 mg, 0.588 mmol) and Et$_3$N (15 drops) in CH$_2$Cl$_2$ (10 mL) was stirred at room temperature overnight. Then it was concentrated under reduced pressure. The resulting crude residue, A66 (1.1 mmol) and Et$_3$N (15 drops) in CH$_2$Cl$_2$ (10 mL) was stirred at room temperature overnight. Then it was concentrated under reduced pressure and purified by column chromatography. PMB-ether (0.444 mmol) was dissolved in acetone (4.5 ml) and water (0.5 ml). CAN (0.845 mmol) was added as a solid, followed by the dropwise addition of a solution of CAN (0.845 mmol) in acetone (0.9 ml) and water (0.1 ml) over 70 minutes. After a further 15 minutes, the reaction mixture was poured into aqueous sodium bicarbonate solution, and extracted with chloroform. The product was purified on chromatography to give 65.

Example 36.15

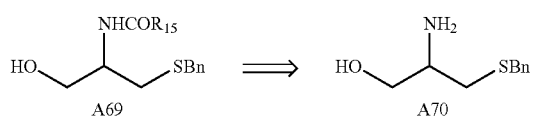

Triethylamine (0.359 mL) was added to a solution of commercially available S-benzyl-(R)-cysteinol (2.56 mmol) in THF (7.50 mL). After 10 min of stirring, di-tert-butyldicarbonate (2.56 mmol) was added at 0° C. The reaction mixture was stirred for 2 h at room temperature. The solvent was then evaporated under reduced pressure; the residue was dissolved in ethyl acetate and washed with water. The organic layer was separated, dried with $Na_2SO_4$, filtered, and evaporated under reduced pressure to yield A69 as a colorless oil.

Example 37

Further Examples of Saccharides According to the Present Invention

31*

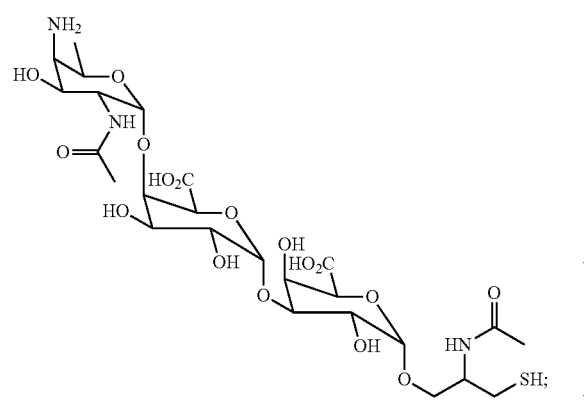

Chemical formula: $C_{25}H_{41}N_3O_{17}S$; Molecular Weight = 687.68

32*

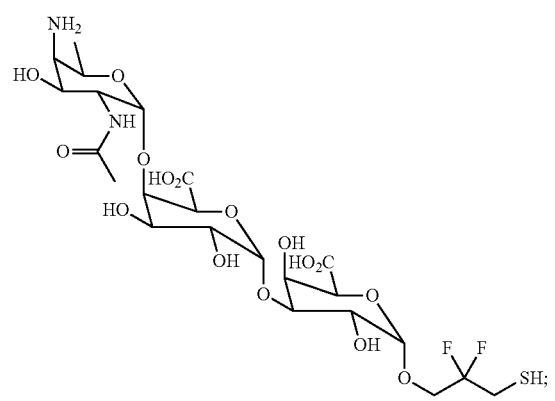

Chemical formula: $C_{23}H_{36}F_2N_2O_{16}S$; Molecular Weight = 666.61

33*

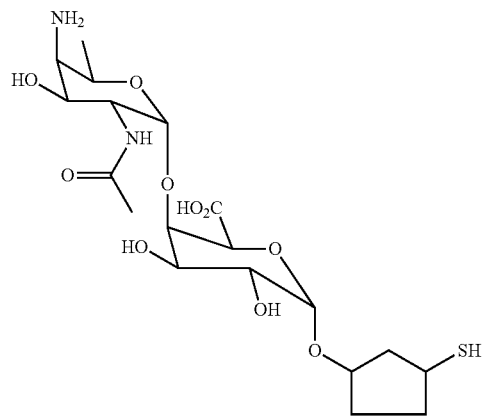

Chemical formula: $C_{19}H_{32}N_2O_{10}S$, Molecular Weight = 480.54;

34*

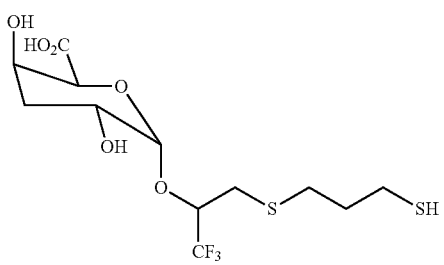

Chemical formula: $C_{12}H_{22}O_6S_2$, Molecular Weight = 326.43;

35*

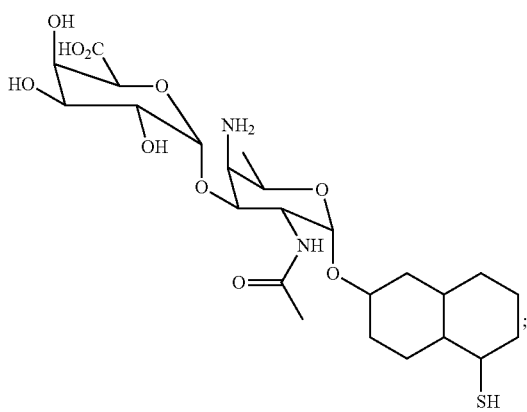

Chemical formula: $C_{24}H_{40}N_2O_{10}S$, Molecular Weight = 548.66

36*

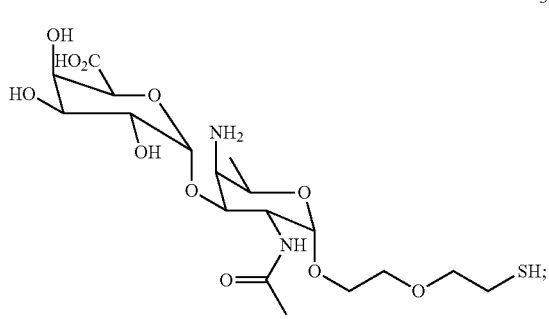

Chemical formula: $C_{18}H_{32}N_2O_{11}S$, Molecular Weight = 484.53

Example 38

Synthesis of glycoconiugates—Conjugation of 2-acetamido-4-amino-2,4,6-trideoxy-α-D-galactopyranosyl-(1→4)-(α-D-galactopyranosyl)uronate-(1→3)-(α-D-galactopyranosyl)uronate-(1→1)-2-(thio)ethanol to CRM197

To a stirred solution of CRM197 (2 mg, 34.5 nmol) in 0.1 M sodium phosphate buffer (NaPi) pH 7.4 (1.33 mL) was added at room temperature a solution of N-Succinimidyl-3-(bromoacetamido)propionate (SBAP) (1.05 mg, 3.4 µmol) in DMF (40 µL). The mixture was stirred for 1 h at that temperature, and concentrated using membrane filtration (Amicon 4 mL Ultra centrifuge membranes, 10 kDa cut-off). The protein solution was diluted to 4 mL with sterile water and concentrated again. This process was repeated three times and the solution was diluted to 0.5 mL using sterile water. 20 µL were taken for analysis, and the protein solution was re-buffered to 0.1 M NaPi pH 8.0 (0.5 mL) using membrane filtration. Disulfide 18* (1.44 mg, 2.33 µmol resp. to the monomer) in 0.1 M NaPi pH 8.0 (0.2 mL) was treated at room temperature with tris(2-carboxyethyl)phosphine (TCEP, 25 µL of a 100 mM stock solution with pH 7.4), left for 1 h at that temperature under an argon atmosphere and added to the solution of the activated protein. The mixture was stirred at room temperature for 16 h, and washed with sterile water using membrane filtration (see above). Another analytical sample was taken, and the solution was re-buffered to 0.1 M NaPi pH 7.4 (0.5 mL). The glycoconjugate was then treated at room temperature with L-cysteine (0.625 mg, 5.1 µmol) in 100 µl sterile water. The mixture was left for 2 h at that temperature and purified by membrane filtration. Incorporation of glycan into the glycoconjugate was assessed by MALDI-TOF-MS (positive mode):

Molecular Weight Measured:

CRM197: 58100 m/z

CRM197-SBAP conjugate: 61700 m/z (incorporation of approximatively 19 SBAP groups)

CRM197-SBAP-glycoconjugate: 66000 m/z (incorporation of approximatively 5.9 molecules of 2-acetamido-4-amino-2,4,6-trideoxy-α-D-galactopyranosyl-(1→4)-(α-D-galactopyranosyl)uronate-(1→3)-(α-D-galactopyranosyl)uronate-(1→1)-2-(thio)ethanol).

Example 39

Immunization Experiment

Mice (6-8 week old female NMRI mice, Charles River) were immunized s. c. with CRM197-SBAP-glycoconjugate synthesized in Example 38 (corresponding to 4 µg synthetic glycan) formulated with or without Alum (Alhydrogel, Brenntag) at a total volume of 100 µL at days 0, 14 and 28. Control groups comprised mice treated equally with Alum only or PBS. Blood was collected at days 0, 14, 28 and 35 and the immune response was assessed by glycan microarray and ELISA.

An immune response against the native Sp1 polysaccharide was found in a subset of mice immunized with glycoconjugate adjuvanted with Alum with an endpoint titer of 500 and 2500 at day 35 compared to day 0, respectively.

The invention claimed is:

1. A saccharide of general formula (I):

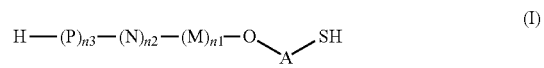

wherein A represents —$(CH_2)_{o1}$—;
o1 represents an integer selected from 1, 2, 3, 4, 5 and 6;
M, N and P represent independently of each other one of the following sugar fragments:

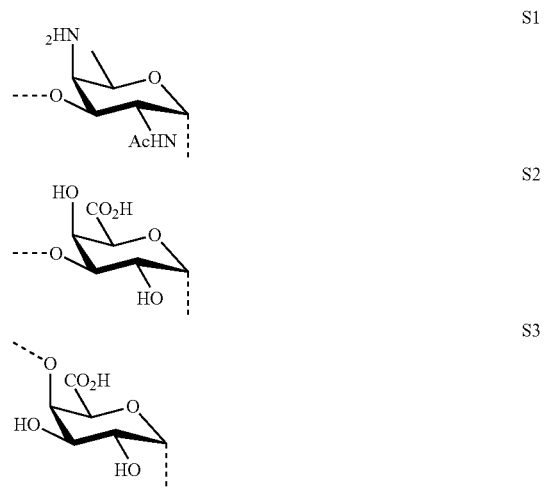

wherein the sugar fragments S1, S2, S3 are connected to each other and to —O-A-SH fragment via O-glycosidic bonds, each sugar fragment S1, S2, and S3 is not more than once present in the general formula (I), sugar fragment Si cannot be simultaneously connected to —O-A-SH and sugar fragment S3, sugar fragment S3 cannot be simultaneously connected to —O-A-SH and sugar fragment S2, and sugar fragment S2 cannot be simultaneously connected to —O-A-SH and sugar fragment S1, and n1, n2 and n3 are integers selected from 0 and 1, wherein at least one of the integers n1, n2 and n3 is 1 and pharmaceutically acceptable salts of these saccharides.

2. A synthesis of the saccharide of the general formula (I):

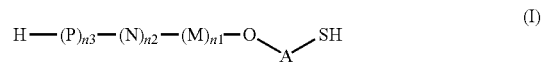

wherein A represents $(CH_2)_{o1}$;
o1 represents an integer selected from 1, 2, 3, 4, 5 and 6;
M, N and P represent independently of each other one of the following sugar fragments:

-continued

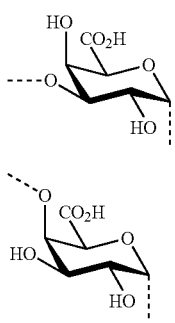

S2

S3 wherein the sugar fragments S1, S2, S3 are connected to each other and to —O-A-SH fragment via O-glycosidic bonds, each sugar fragment S1, S2, and S3 is not more than once present in the general formula (I), sugar fragment Si cannot be simultaneously connected to —O-A-SH and sugar fragment S3, sugar fragment S3 cannot be simultaneously connected to —O-A-SH and sugar fragment S2, and sugar fragment S2 cannot be simultaneously connected to —O-A-SH and sugar fragment S1, and n1, n2 and n3 are integers selected from 0 and 1, wherein at least one of the integers n1, n2 and n3 is 1 and comprising:

A1) Reacting the compound 2 of the formula:

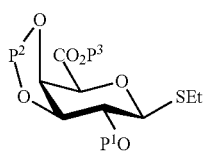

2 wherein $P^1$-$P^3$ represent protecting groups, with the compound 3 of the formula

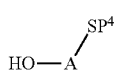

3 wherein $P^4$ represents a protecting group, in order to obtain compound 4 of general formula:

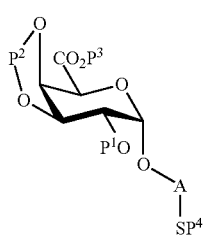

4 wherein $P^1$-$P^4$ and A are defined as above; and
performing removal of protecting groups $P^1$-$P^4$ on compound 4 to afford monosaccharide disulfide 5 of general formula:

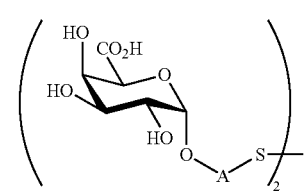

5 wherein A is defined as above, and wherein monosaccharide disulfide 5 is further treated with a reducing agent to afford monosaccharide 6 of general formula:

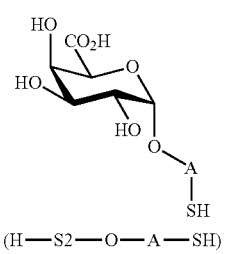

6

(H—S2—O—A—SH)

wherein A is defined as above;

or performing selective deprotection on compound 4 to afford compound 7 of general formula

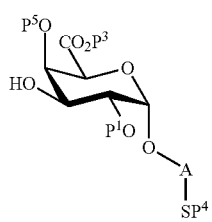

7 wherein $P^5$ is a protecting group and $P^1$, $P^3$, $P^4$ and A are defined as above;

or

A2) Reacting compound 8 of general formula

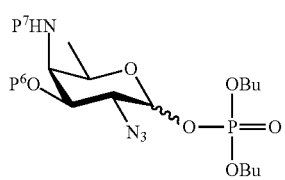

8 wherein $P^6$ and $P^7$ represent protecting groups, with compound 3 to afford compound 9 of general formula

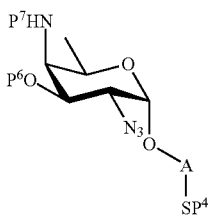

9 wherein $P^6$, $P^7$ and A are defined as above;

and performing conversion of the azido group to acetamido group and removal of the protecting groups $P^4$, $P^6$ and $P^7$ on compound 9 to afford monosaccharide disulfide 10 of general formula:

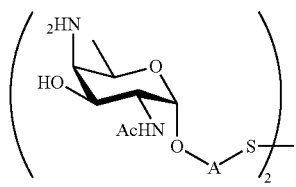

10 wherein A is defined as above, and wherein monosaccharide disulfide 10 is further treated with a reducing agent to afford monosaccharide 11 of general formula:

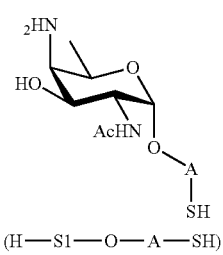

11 wherein A is defined as above;

or performing selective deprotection on compound 9 to afford compound 12 of general formula:

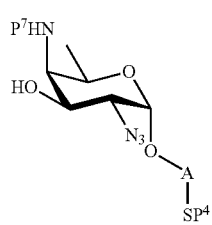

12 wherein $P^4$, $P^7$ and A are defined as above;

or

A3) Reacting compound 13 of general formula

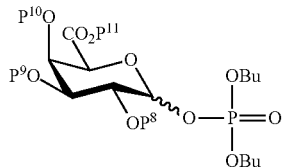

13 wherein $P^8$-$P^{11}$ represent protecting groups, with compound 3 to afford compound 14 of general formula:

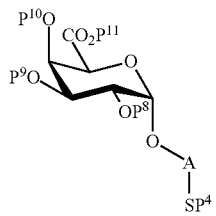

14 wherein $P^4$, $P^8$-$P^{11}$ are defined as above; and performing selective deprotection of compound 14 to afford compound 15 of general formula:

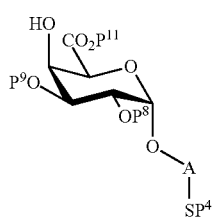

15 wherein $P^4$, $P^8$, $P^9$, $P^{11}$ and A are defined as above; and

B1) Reacting compound 7 with compound 13 to afford compound 16 of general formula:

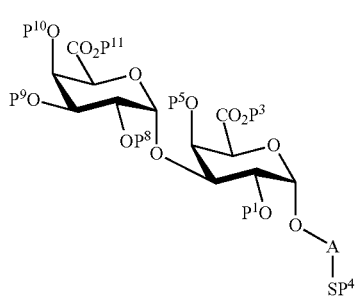

16 wherein $P^1$, $P^3$-$P^5$, $P^8$-$P^{11}$ and A are defined as above; and performing removal of protecting groups $P^1$ $P^3$-$P^5$, $P^8$-$P^{11}$ on compound 16 to afford disaccharide disulfide 17 of general formula:

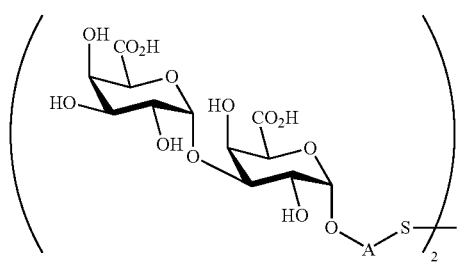

(17)

wherein A is defined as above and wherein disaccharide disulfide 17 is further treated with a reducing agent to afford disaccharide 18 of general formula:

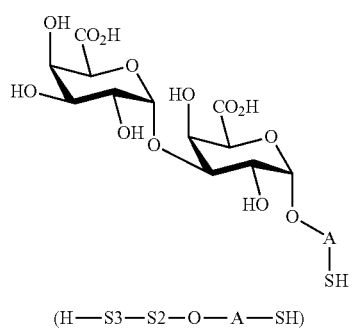

(18)

(H—S3—S2—O—A—SH)

wherein A is defined as above;
or
performing selective removal of protecting group $P^{10}$ on compound 16 to afford compound 19 of general formula:

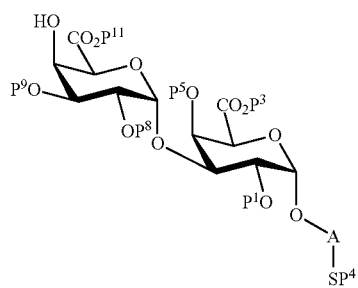

(19)

wherein $P^1$, $P^3$-$P^5$, $P^8$, $P^9$, $P^{11}$ and A are defined as above;
or
B2) Reacting compound 15 with compound 8 to afford compound 20 of general formula:

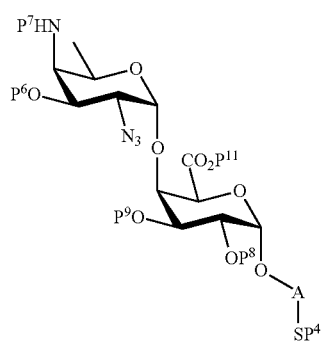

(20)

wherein $P^4$, $P^6$-$P^9$, $P^{11}$ and A are defined as above; and performing conversion of the azido group to acetamido group and removal of the protecting groups $P^4$, $P^6$-$P^9$, $P^{11}$ on compound 20 to afford disaccharide disulfide 21 of general formula:

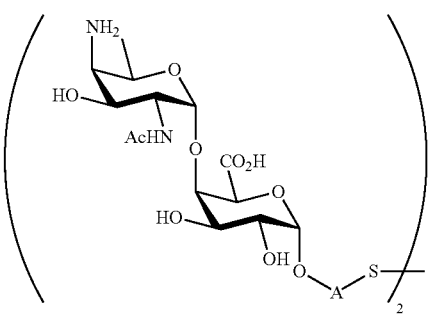

(21)

wherein A is defined as above and wherein disaccharide disulfide 21 is treated with a reducing agent to afford disaccharide 22 of general formula:

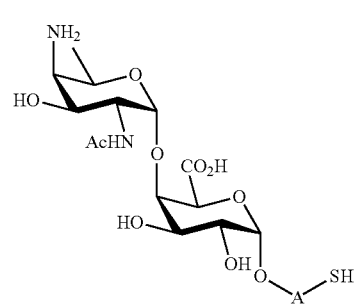

(22)

(H—S1—S3—O—A—SH)

wherein A is defined as above;
or
performing selective removal of protecting group $P^6$ on compound 20 to afford compound 23 of general formula:

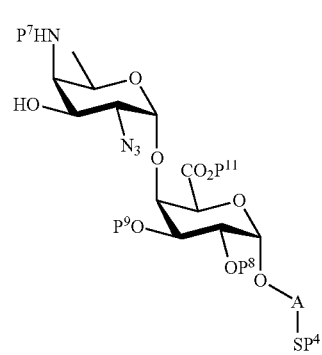

(23)

wherein $P^4$, $P^7$-$P^9$, $P^{11}$ and A are defined as above;
or
B3) Reacting compound 12 with compound 2 to afford compound 24 of general formula:

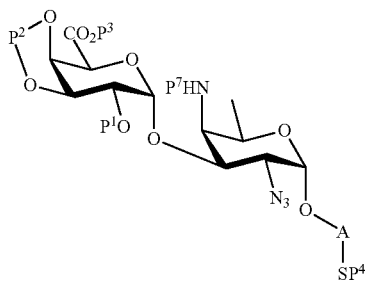

24 wherein $P^1$-$P^4$, $P^7$ and A are defined as above,
and
performing conversion of the azido group to acetamido group and removal of protecting groups $P^1$-$P^4$ and $P^7$ on compound 24 to afford disaccharide disulfide 25 of general formula:

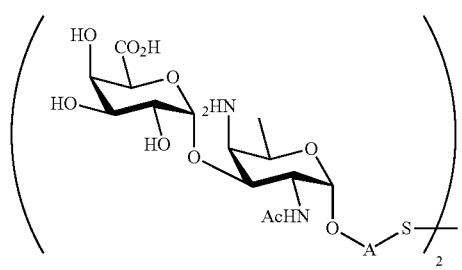

25 wherein A is defined as above, and wherein disaccharide disulfide 25 is further treated with a reducing agent to afford disaccharide 26 of general formula:

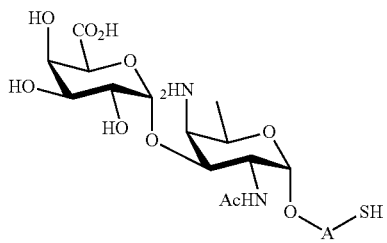

26

(H—S2—S1—O—A—SH)

wherein A is defined as above;
or
performing selective deprotection on compound 24 to afford compound 27 of general formula:

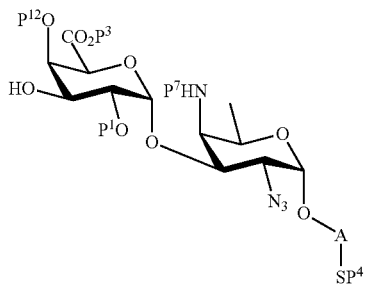

27 wherein $P^{12}$ is a protecting group and $P^1$, $P^3$, $P^4$, $P^7$ and A are defined as above;

and
C1) Reacting compound 19 with compound 8 to afford compound 28 of general formula:

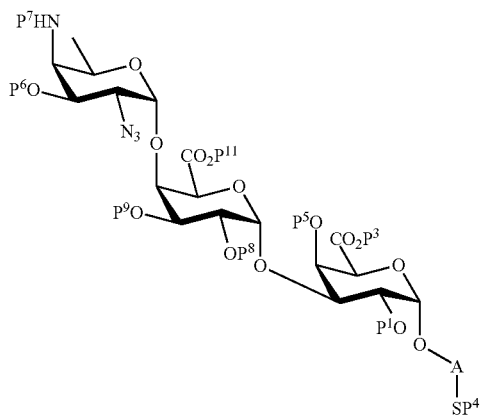

28 wherein $P^1$, $P^3$-$P^9$, $P^{11}$ and A are defined as above;
and
wherein protecting group $P^6$ is replaced with protecting group $P^{13}$ in order to obtain compound 29 of the following chemical formula:

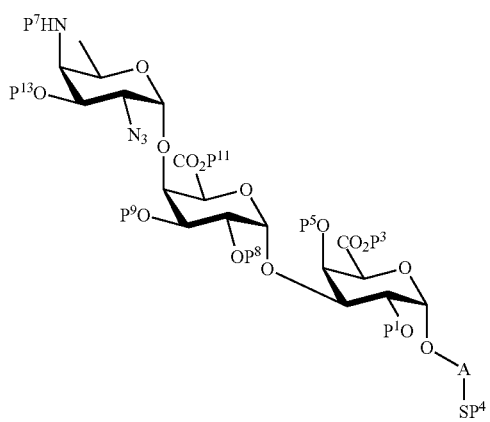

29 wherein $P^1$, $P^3$-$P^5$, $P^7$-$P^9$, $P^{11}$, $P^{13}$ and A are defined as above;
and
conversion of compound 29 to trisaccharide disulfide 30 by conversion of the azido group in the acetamido group and cleavage of the protecting group $P^1$, $P^3$-$P^5$, $P^7$-$P^9$, $P^{11}$, $^{13}$, wherein compound 30 is of general formula:

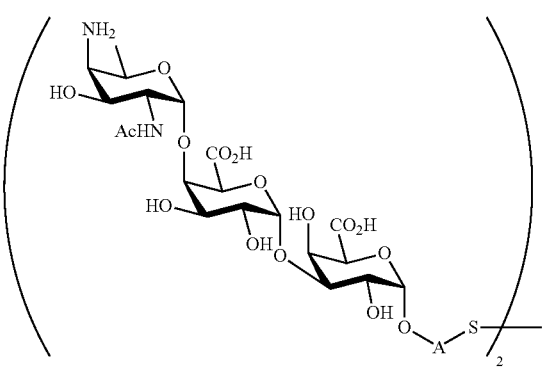

30 and wherein A is defined as above;

and
conversion of trisaccharide disulfide 30 to trisaccharide 31 by treatment with a reducing agent, wherein compound 31 is of general formula:

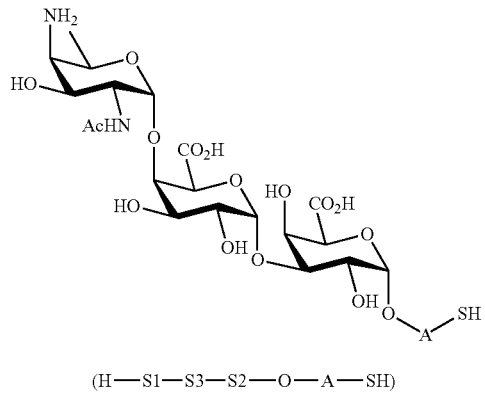

31

(H—S1—S3—S2—O—A—SH)

and wherein A is defined as above;
or
C2) Reacting compound 23 with compound 2 to afford compound 32 of general formula:

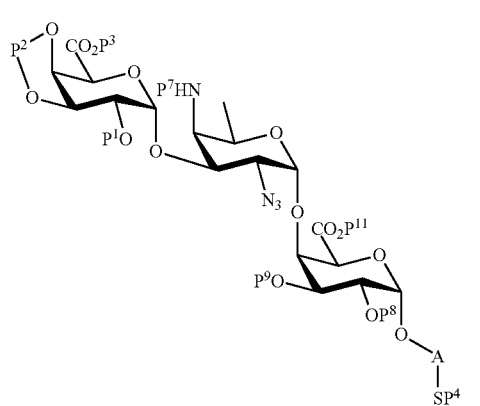

32 wherein $P^1$-$P^4$, $P^7$-$P^9$, $P^{11}$ and A are defined as above; and
conversion of compound 32 to trisaccharide disulfide 33 by conversion of the azido group in the acetamido group and cleavage of the protecting group $P^1$-$P^4$, $P^7$-$P^9$, $P^{11}$, wherein compound 33 is of general formula:

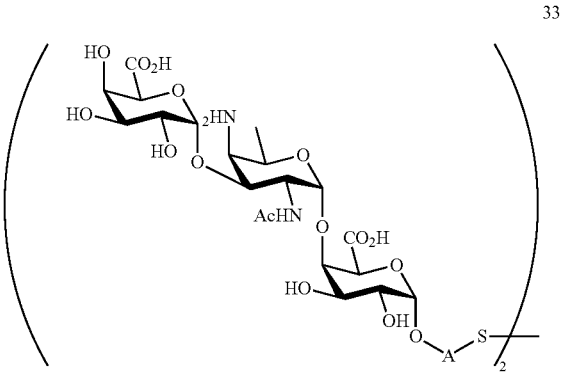

33 wherein A is defined as above;

and
conversion of trisaccharide disulfide 33 to trisaccharide 34 by treatment with a reducing agent, wherein compound 34 is of general formula:

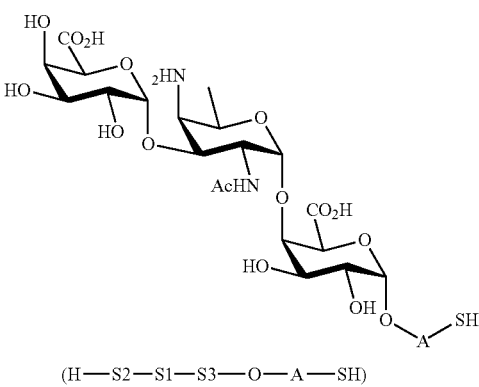

34

(H—S2—S1—S3—O—A—SH)

wherein A is defined as above;
or
C3) Reacting compound 27 with compound 13 to afford compound 35 of general formula:

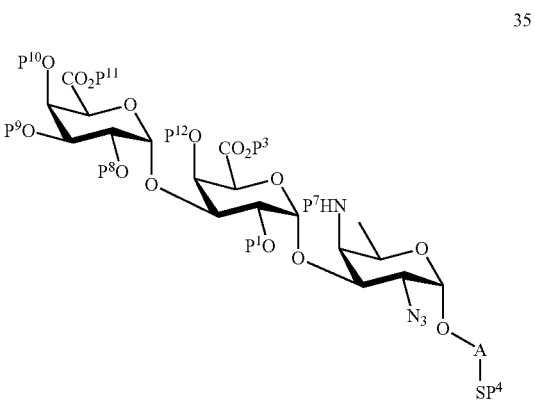

35 wherein $P^1$, $P^3$, $P^4$, $P^7$-$P^{11}$ and A are defined as above; and
conversion of compound 35 to trisaccharide disulfide 36 by conversion of the azido group in the acetamido group and cleavage of the protecting group $P^1$, $P^3$, $P^4$, $P^7$-$P^{11}$ wherein compound 36 is of general formula:

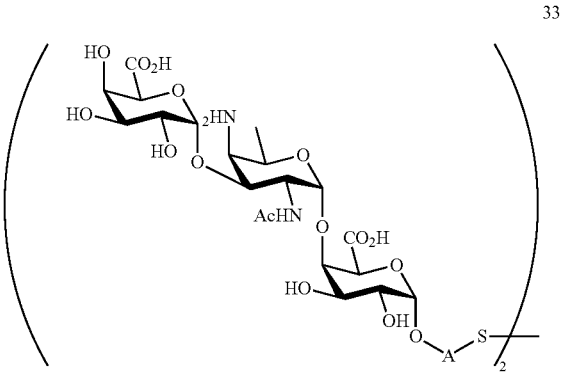

36 wherein A is defined as above;

and
conversion of trisaccharide disulfide 36 to trisaccharide 37 by treatment with a reducing agent, wherein compound 37 is of general formula:

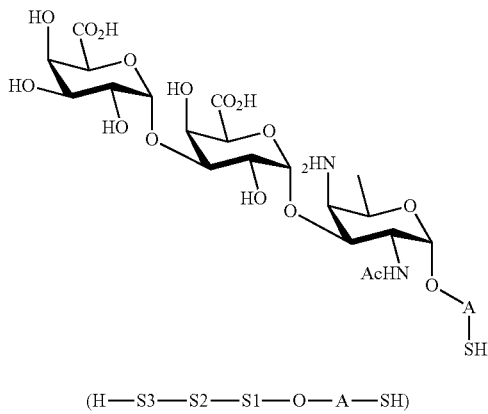

(H—S3—S2—S1—O—A—SH)

wherein A is defined as above.

3. The synthesis according to claim 2 further comprising:
preparing a salt of the compound of general formula (I) or
preparing a lyophilisate of the compound of general formula (I) or of the salt of the compound of general formula (I).

4. The synthesis according to claim 2, wherein the reactions between compounds 2 and 3, compounds 2 and 12, and compounds 2 and 23 are performed in presence of DMTST and TTBPy in a mixture of non-polar and polar aprotic solvents.

5. The synthesis according to claim 2, wherein the replacement of protecting group $P^6$ on compound 28 with protecting group $P^{13}$ to obtain compound 29 is performed in two steps, first involving the reaction of compound 28 with hydrazine or a hydrazinium salt in a solvent or a mixture of solvents, and second by treatment of the product obtained after the first step with $BnOCH_2SCy$, DMTST and TTBPy in a non-polar solvent.

6. The synthesis according to claim 2, wherein the cleavage of the protecting groups involves first cleavage of the base-labile protecting groups by treatment with a base in a mixture of polar aprotic and polar protic solvents; and second cleavage of the protecting groups sensitive to hydrogenation by exposure to sodium and ammonia in a mixture of polar protic and polar aprotic solvents.

7. A pharmaceutical composition comprising the saccharide according to claim 1 together with at least one pharmaceutically acceptable cryoprotectant, lyoprotectant, excipient and/or diluent.

* * * * *